US007253268B2

(12) United States Patent
Delong et al.

(10) Patent No.: US 7,253,268 B2
(45) Date of Patent: Aug. 7, 2007

(54) LIGHT-DRIVEN ENERGY GENERATION USING PROTEORHODOPSIN

(75) Inventors: Edward F. Delong, Monterey, CA (US); Oded Beja, Marina, CA (US)

(73) Assignee: Monterey Bay Aquarium Research Institute, Moss Landing, CA (US)

(*) Notice: Subject to any disclaimer, the term of this patent is extended or adjusted under 35 U.S.C. 154(b) by 0 days.

(21) Appl. No.: 09/847,513

(22) Filed: May 1, 2001

(65) Prior Publication Data

US 2003/0104375 A1 Jun. 5, 2003

Related U.S. Application Data

(60) Provisional application No. 60/201,602, filed on May 3, 2000.

(51) Int. Cl.
*C07M 21/02* (2006.01)
*C07M 21/04* (2006.01)
*C12N 15/00* (2006.01)
*C12N 15/09* (2006.01)
*C12N 15/63* (2006.01)

(52) U.S. Cl. .................................. 536/23.1; 435/320.1

(58) Field of Classification Search ............... 536/23.1, 536/24.3; 530/350

See application file for complete search history.

(56) References Cited

U.S. PATENT DOCUMENTS

| | | | | |
|---|---|---|---|---|
| 5,290,699 | A | 3/1994 | Oesterdhelt et al. | 435/252.3 |
| 5,470,690 | A | 11/1995 | Lewis et al. | 430/269 |
| 5,757,525 | A | 5/1998 | Rao et al. | 359/108 |
| 5,854,710 | A | 12/1998 | Rao et al. | 359/559 |

OTHER PUBLICATIONS

Kitajima, T. et al., "Novel Bacterial Rhodopsins from *Haloarcula vallismortis*", Biochem. Biophys. Res. Comm., vol. 220, pp. 341 345 (1996).*

Monaco, A. P. et al., "YACs, BACs, PACs and MACs: artificial chromosomes as research tools", Trends in Biotech., vol. 12, pp. 280-286 (1994).*

Shimono, K. et al., "Functional expression of pharaonis phoborhodopsin in *Eschericha coli*", FEBS Letters, vol. 420, pp. 54-56 (1997).*

Mollaaghababa, R. et al. "Structure and function in rhodopsin: Expression of functional mammalian opsin in *Saccharomyces cerevisiae*", PNAS, vol. 93, pp. 11482-11486 (1996).*

Zozulya, S.A. et al., "Functional expression in vitro of bovine visual rhodopsin", Protein Eng., vol. 3, pp. 453-458 (1990).*

Ihara, K. et al., "Evolution of the Archeal Rhodopsins: Evolution Rate Changes by Gene Duplication and Functional Differentiation", J. Mol. Biol., vol. 285, pp. 163-174 (1999).*

Jennifer A. Bieszke, Edward L. Braun, Laura E. Bean, Seogchan Kang, Donald O. Natvig, and Katherine A. Borkovich; "The nop-1 gene of *Neurospora crassa* encodes a seven transmembrane helix retinal-binding protein homologous to *Archaeal rhodopsins*;" Proc. Natl. Acad. Sci. USA vol. 96, pp. 8034-8039, Jul. 1999.

Jennifer A. Bieszke, Elena N. Spudich, Kenneth L. Scott, Katherine A. Borkovich, and John L. spudich; "A eukaryotic protein, NOP-1, binds retinal to form an *Archaeal rhodopsin*-like photochemically reactive pigment;" Biochemistry 1999, 38, 14138-14145.

Oded Beja et al,, "Bacterial rhodopsin: evidence for a new type of phototrophy in the sea," Sep. 15, 2000, vol. 289, Science p. 1902 to 1906.

Elizabeth Pennise, "High-tech lures hook into new marine microbes," Science vol. 289 Sep. 15, 2000, p. 1869.

AF279106 Uncultured marine . . . [gi:34112904], retrieved on Sep. 30, 2003. Retrieved from the internet: <URL:http://www.ncbi.nlm.nih.gov:80/entrez/query.fcgi?cmd=retrieve&db=nucleotide&list_uids=34112904&dopt=GenBank&term=AF279106>.

* cited by examiner

*Primary Examiner*—Teresa E. Strzelecka
(74) *Attorney, Agent, or Firm*—Lumen Intellectual Property Services, Inc.

(57) ABSTRACT

A light-driven energy generation system using proteorhodopsin is provided. Proteorhodopsin sequences were retrieved and amplified from naturally occurring members of the domain Bacteria using proteorhodopsin-specific polymerase chain reaction primers. Proteorhodopsin sequences were placed in expression vectors for production of proteorhodopsin proteins in a host, for instance, *E. coli* and other bacteria. The system also includes a light source and a source of retinal, that allows the system to convert light into biochemical energy. The generated biochemical energy could be mediated into electrical energy by a mediator.

10 Claims, 108 Drawing Sheets
(1 of 108 Drawing Sheet(s) Filed in Color)

accatgggta aattattact gatattagg

Figure 2 agcattagaa gattctttaa cagc 24

Figure 3

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta     336
Ile Asp Trp Leu Leu Thr Val Pro Leu Leu Ile Cys Glu Phe Tyr Leu
            100                 105                 110
```

Figure 4-A

```
att ctt gct gct gca act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa tta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

att atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ctg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 4-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 4-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tcg ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gag act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta     336
Ile Asp Trp Leu Leu Thr Val Pro Leu Leu Ile Cys Glu Phe Tyr Leu
            100                 105                 110
```

Figure 6-A

```
att ctt gct gct gca aca aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt      528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190
ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 6-B

```
gac ctt gct gac ttt gtt aac aag att cta ttt ggt tta att ata tgg       720
Asp Leu Ala Asp Phe Val Asn Lys Ile Leu Phe Gly Leu Ile Ile Trp
225                 230                 235                 240

aat gtt gct gtt aaa gaa tct tct aat gct                               750
Asn Val Ala Val Lys Glu Ser Ser Asn Ala
                245                 250
```

Figure 6-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gct act gct gct tta tta gca tct act gta ttt ttc     144
Ser Phe Trp Leu Ala Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta     336
Ile Asp Trp Leu Leu Thr Val Pro Leu Leu Ile Cys Glu Phe Tyr Leu
            100                 105                 110
```

Figure 7-A

```
att ctt gct gct gct act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

att atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ctg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 7-B

```
aac ctt gct gat ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 7-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga gga gta tgg att gaa act ggt gat tcg cct act gta ttt aga tac     288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta     336
Ile Asp Trp Leu Leu Thr Val Pro Leu Leu Ile Cys Glu Phe Tyr Leu
            100                 105                 110
```

Figure 8-A

```
att ctt gct gct gca act aat gtt gcc ggc tca tta ttt aag aaa ctt     384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca     432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg     480
Gly Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt     528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct     576
Asn Thr Ala Ser Pro Ser Val Gln Ser Ala Tyr Asn Thr Met Met Ala
            180                 185                 190

atc ata gtc ttc ggt tgg gca att tat cct ata ggt tat ttc aca ggt     624
Ile Ile Val Phe Gly Trp Ala Ile Tyr Pro Ile Gly Tyr Phe Thr Gly
        195                 200                 205

tac cta atg ggt gac ggt gga tca gct ctt aac tta aac ctt att tat     672
Tyr Leu Met Gly Asp Gly Gly Ser Ala Leu Asn Leu Asn Leu Ile Tyr
    210                 215                 220
```

Figure 8-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                             750
Asn Val Ala Val Lys Glu Ser Ser Asn Ala
                245                 250
```

Figure 8-C

```
EBAC31A8    1 atgggtaaat tattactgat attaggTAGT GTTATTGCAC TTCCTACATT  50
  EBAC40    1 .......... .......... .......... .......... ..........  50
  EBAC41    1 .......... .......... .......... .......... ..........  50
  EBAC64    1 .......... .......... .......... .......... ..........  50

EBAC31A8   51 TGCTGCAGGT GGTGGTGACC TTGATGCTAG TGATTACACT GGTGTTTCTT 100
  EBAC40   51 .......... .......... .......... .......... .......... 100
  EBAC41   51 .......... .......... .......... .......... .......... 100
  EBAC64   51 .......... ..C....... .......... .......... .......... 100

EBAC31A8  101 TTTGGTTAGT TACTGCTGCT TTATTAGCAT CTACTGTATT TTTCTTTGTT 150
  EBAC40  101 .......... .......... C......... .......... .......... 150
  EBAC41  101 .........C .......... .......... .......... .......... 150
  EBAC64  101 .......... ...A...... C......... .......... .......... 150

EBAC31A8  151 GAAAGAGATA GAGTTTCTGC AAAATGGAAA ACATCATTAA CTGTATCTGG 200
  EBAC40  151 .......... .......... .......... .......... .......G.. 200
  EBAC41  151 .......... .......... .......... .......... .......... 200
  EBAC64  151 .......... .......... .......... .......... .......... 200

EBAC31A8  201 TCTTGTTACT GGTATTGCTT TCTGGCATTA CATGTACATG AGAGGGGTAT 250
  EBAC40  201 .......... .......... .......... .......... .......... 250
  EBAC41  201 .......... .......... .......... .......... .......... 250
  EBAC64  201 .......... .......... .......... .......... .....A.... 250

EBAC31A8  251 GGATTGAAAC TGGTGATTCG CCAACTGTAT TTAGATACAT TGATTGGTTA 300
  EBAC40  251 .......G.. .......... .......... .......... .......... 300
  EBAC41  251 .......... .......... .......... .......... .......... 300
  EBAC64  251 .......... .......... ..T....... .......... .......... 300
```

Figure 9-A

```
EBAC31A8  301  CTAACAGTTC CTCTATTAAT ATGTGAATTC TACTTAATTC TTGCTGCTGC  350
  EBAC40  301  .......... .......G.. .......... .......... ..........  350
  EBAC41  301  .......... .......... .......... .......... ..........  350
  EBAC64  301  .......... ..T....... .......... .......... ..........  350

EBAC31A8  351  AACTAATGTT GCTGGATCAT TATTTAAGAA ATTACTAGTT GGTTCTCTTG  400
  EBAC40  351  ...A...... ....CTGGCC .G........ ....T.G... ..........  400
  EBAC41  351  T......... .......... .......... .......... ..........  400
  EBAC64  351  .......... ..C..C.... .......... .C.T...... ..........  400

EBAC31A8  401  TTATGCTTGT GTTTGGTTAC ATGGGTGAAG CAGGAATCAT GGCTGCATGG  450
  EBAC40  401  .......... .......... ........G. .......T.. .AAC..T...  450
  EBAC41  401  .......... .......... .......... .......... ..........  450
  EBAC64  401  .......... .......... .......... .......T.. ...A..T...  450

EBAC31A8  451  CCTGCATTCA TTATTGGGTG TTTAGCTTGG GTATACATGA TTTATGAATT  500
  EBAC40  451  GG.......G .......... .......... .......... ........C.  500
  EBAC41  451  .......... .......... .......... .......... ........C.  500
  EBAC64  451  .......... .......... .......... .......... ........C.  500

EBAC31A8  501  ATGGGCTGGA GAAGGAAAAT CTGCATGTAA TACTGCAAGT CCTGCTGTGC  550
  EBAC40  501  .......... .....C..GG .......... .......... ..........  550
  EBAC41  501  .......... .......... .......... .......... ..........  550
  EBAC64  501  ..AT...... .......... .......... .......... ...T.G..T.  550

EBAC31A8  551  AATCAGCTTA CAACACAATG ATGTATATTA TCATCTTTGG TTGGGCGATT  600
  EBAC40  551  .......... .......... ........A. .......... ......A...  600
  EBAC41  551  .......... .......... .......... .......... ..........  600
  EBAC64  551  .......... .......... ...GC...C. .AG....C.. ......A...  600
```

Figure 9-B

```
EBAC31A8   601   TATCCTGTAG GTTATTTCAC AGGTTACCTG ATGGGTGACG GTGGATCAGC   650
  EBAC40   601   .......... .......... .........A .......... ..........   650
  EBAC41   601   .......... .......... .......... .......... ..........   650
  EBAC64   601   ......A... .......... .........A .......... ..........   650

EBAC31A8   651   TCTTAACTTA AACCTTATCT ATAACCTTGC TGACTTTGTT AACAAGATTC   700
  EBAC40   651   .......... .......... ..G....... .......... ..........   700
  EBAC41   651   .......... .......... .......... ...T...... ..........   700
  EBAC64   651   .......... ........T. .......... .......... ..........   700

EBAC31A8   701   TATTTGGTTT AATTATATGG AATGTTgctg ttaaagaatc ttctaatgct   750
  EBAC40   701   .......... .......... .......... .......... ..........   750
  EBAC41   701   .......... .......... .......... .......... ..........   750
  EBAC64   701   .......... .......... .......... .......... ..........   750
```

Figure 9-C

```
EBAC31A8    1  MGKLLLILGS VIALPTFAAG GGDLDASDYT GVSFWLVTAA LLASTVFFFV   50
EBAC40_1    1  .......... .......... .......... .......... ..........   50
EBAC41_1    1  .......... .......... .......... ......A... ..........   50
EBAC64_1    1  .......... .......... .......... .......... ..........   50

EBAC31A8   51  ERDRVSAKWK TSLTVSGLVT GIAFWHYMYM RGVWIETGDS PTVFRYIDWL  100
EBAC40_1   51  .......... .......... .......... .......... ..........  100
EBAC41_1   51  .......... .......... .......... .......... ..........  100
EBAC64_1   51  .......... .......... .......... .......... ..........  100

EBAC31A8  101  LTVPLLICEF YLILAAATNV AGSLFKKLLV GSLVMLVFGY MGEAGIMAAW  150
EBAC40_1  101  .......... .......... .AG....... .......... .......N..  150
EBAC41_1  101  .......... .......... .......... .......... ..........  150
EBAC64_1  101  .......... .......... .......... .......... ..........  150

EBAC31A8  151  PAFIIGCLAW VYMIYELWAG EGKSACNTAS PAVQSAYNTM MYIIIFGWAI  200
EBAC40_1  151  G..V...... .......... ...A...... .......... ..........  200
EBAC41_1  151  .......... .......... .......... .......... ..........  200
EBAC64_1  151  .......... .......Y.. .......... .S........ .A..V.....  200

EBAC31A8  201  YPVGYFTGYL MGDGGSALNL NLIYNLADFV NKILFGLIIW NVAVKESSNA  250
EBAC40_1  201  .......... .......... ....D..... .......... ..........  250
EBAC41_1  201  .......... .......... .......... .......... ..........  250
EBAC64_1  201  ..I....... .......... .......... .......... ..........  250
```

Figure 10

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tcg ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gag acc ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta     336
Ile Asp Trp Leu Leu Thr Val Pro Leu Leu Ile Cys Glu Phe Tyr Leu
            100                 105                 110
```

Figure 11-A

```
att ctt gct gct gca aca aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt      528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 11-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 11-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt     144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt gct     192
Phe Val Glu Arg Asp Gln Val Ser Ala Lys Trp Lys Thr Ser Leu Ala
    50                  55                  60

gta tct ggt tta att act ggt ata gct ttt tgg cat tat ctc tat atg     240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat     288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta     336
Ile Asp Trp Leu Leu Thr Val Pro Leu Gln Met Val Glu Phe Tyr Leu
            100                 105                 110
```

Figure 12-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220
```

Figure 12-B

```
tat aac ctt gcc gac ctt gtt aac aag att cta ttt ggt ttg atc att      720
Tyr Asn Leu Ala Asp Leu Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 12-C

```
atg ggt aaa tta tta ctg ata tta ggt agt gct att gca ctt cca tca     48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt     96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gta ttc ttt    144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act    192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg    240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat    288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta    336
Ile Asp Trp Leu Leu Thr Val Pro Leu Gln Met Val Glu Phe Tyr Leu
            100                 105                 110
```

Figure 13-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

ggt tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta cat atg ggt gaa ggt aag gct gct gta      528
Leu Tyr Met Ile Tyr Glu Leu His Met Gly Glu Gly Lys Ala Ala Val
                165                 170                 175

agt act gca agt cct gct gtt aac tct gca tac aac gca atg atg aag      576
Ser Thr Ala Ser Pro Ala Val Asn Ser Ala Tyr Asn Ala Met Met Lys
            180                 185                 190

att att gtt att gga tgg gca att tat cct gct gga tat gct gct ggt      624
Ile Ile Val Ile Gly Trp Ala Ile Tyr Pro Ala Gly Tyr Ala Ala Gly
        195                 200                 205

tac cta atg agt ggt gac ggt gta tac gct tca aac tta aac ctt ata      672
Tyr Leu Met Ser Gly Asp Gly Val Tyr Ala Ser Asn Leu Asn Leu Ile
    210                 215                 220
```

Figure 13-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 13-C

```
atg ggt aaa tta tta ctg ata tta ggt agt gct att gca ctt cca tca    48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt    96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt   144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act   192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg   240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat   288
Arg Gly Val Trp Ile Asp Thr Gly Asp Thr Pro Thr Val Phe Arg Tyr
                85                  90                  95

att gat tgg tta tta act gtt cca tta caa gtg gtt gag ttc tat cta   336
Ile Asp Trp Leu Leu Thr Val Pro Leu Gln Val Val Glu Phe Tyr Leu
            100                 105                 110
```

Figure 14-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220
```

Figure 14-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 14-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt     144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act     192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg     240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat     288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta     336
Ile Asp Trp Leu Leu Thr Val Pro Leu Gln Met Val Glu Phe Tyr Leu
            100                 105                 110
```

Figure 15-A

```
att ctt gct gct tgt aca aat gtt gct gct tca tta ttt aag aag ctt      384
Ile Leu Ala Ala Cys Thr Asn Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga ttg gct cct gta tgg cct gct ttc att att ggt atg gct gga tgg      480
Gly Leu Ala Pro Val Trp Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg gtg      576
Ser Thr Ala Ser Pro Ala Val Asn Ser Ala Tyr Asn Ala Met Met Val
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220
```

Figure 15-B

```
tat aac ctt gcc gac ctt gtt aac aag att cta ttt ggt ttg atc att      720
Tyr Asn Leu Ala Asp Leu Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 15-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gag act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta     336
Ile Asp Trp Leu Leu Thr Val Pro Leu Leu Ile Cys Glu Phe Tyr Leu
            100                 105                 110
```

Figure 16-A

```
att ctt gct gct gca aca aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg cct gca ttc att att ggg tgt tta gct tgg      480
Gly Ile Met Asn Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt gga tca gct ctt aac tta aac ctt att tat      672
Tyr Leu Met Gly Asp Gly Gly Ser Ala Leu Asn Leu Asn Leu Ile Tyr
    210                 215                 220
```

Figure 16-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 16-C

```
atg ggt aaa tta tta ctg ata tta ggt agt gtt att gca ctt cct aca        48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt        96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc       144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act       192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg       240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac       288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta       336
Ile Asp Trp Leu Leu Thr Val Pro Leu Leu Ile Cys Glu Phe Tyr Leu
            100                 105                 110
```

Figure 17-A

```
att ctt gct gct gct act aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gag ctt tgg ctt gga gaa gga aaa gct gcg tgt      528
Val Tyr Met Ile Tyr Glu Leu Trp Leu Gly Glu Gly Lys Ala Ala Cys
                165                 170                 175

aat aca gca agt cct gct gtt cag tca gct tac aac aca atg atg atg      576
Asn Thr Ala Ser Pro Ala Val Gln Ser Ala Tyr Asn Thr Met Met Met
            180                 185                 190

atc atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gca ctt aac tta aac ctt atc tat      672
Tyr Leu Met Gly Asp Gly Gly Ser Ala Leu Asn Leu Asn Leu Ile Tyr
    210                 215                 220
```

Figure 17-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 17-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta     336
Ile Asp Trp Leu Leu Thr Val Pro Leu Leu Ile Cys Glu Phe Tyr Leu
            100                 105                 110
```

Figure 18-A

```
att ctt gct gct gca act aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt      528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 18-B

```
aac ctt gct gac ttt gtt aac aag att cta ttt ggt tta att ata tgg       720
Asn Leu Ala Asp Phe Val Asn Lys Ile Leu Phe Gly Leu Ile Ile Trp
225                 230                 235                 240

aat gtt gct gtt aaa gaa tct tct aat gct                               750
Asn Val Ala Val Lys Glu Ser Ser Asn Ala
                245                 250
```

Figure 18-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta     336
Ile Asp Trp Leu Leu Thr Val Pro Leu Leu Ile Cys Glu Phe Tyr Leu
            100                 105                 110
```

Figure 19-A

```
att ctt gct gct gct act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

caa att atg gct gca tgg cct gca ttc att att ggg tgt tta gct tgg      480
Gln Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt ggg tca gct ctt aac tta aac ctt att tat      672
Tyr Leu Met Gly Asp Gly Gly Ser Ala Leu Asn Leu Asn Leu Ile Tyr
    210                 215                 220
```

Figure 19-B

```
aac ctt gct gac ttt gtt aac aag att cta ctt ggt tta att ata tgg      720
Asn Leu Ala Asp Phe Val Asn Lys Ile Leu Leu Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 19-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta     336
Ile Asp Trp Leu Leu Thr Val Pro Leu Leu Ile Cys Glu Phe Tyr Leu
            100                 105                 110
```

Figure 20-A

```
att ctt gct gct gca gct aat gtt gct gga tca tta ttt aag aaa tta      384
Ile Leu Ala Ala Ala Ala Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa tta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gcc tac aac aca atg atg tat      576
Asn Thr Ala Ser Pro Ala Val Gln Ser Ala Tyr Asn Thr Met Met Tyr
            180                 185                 190

att atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ttg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 20-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 20-C

```
atg ggt aaa tta tta ctg ata ata ggt agt gtt att gca ctt cct aca      48
Met Gly Lys Leu Leu Leu Ile Ile Gly Ser Val Ile Ala Leu Pro Thr
1               5                   10                  15

ttt gct gca ggt ggc ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta     336
Ile Asp Trp Leu Leu Thr Val Pro Leu Leu Ile Cys Glu Phe Tyr Leu
            100                 105                 110
```

Figure 21-A

```
att ctt gct gct gca act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tat atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat aca gca agt cct gct gtg caa tca gct tac aac aca atg atg tat      576
Asn Thr Ala Ser Pro Ala Val Gln Ser Ala Tyr Asn Thr Met Met Tyr
            180                 185                 190

att atc gtc ttt ggt tgg gcg att tat cct gta ggt tat ttc aca ggt      624
Ile Ile Val Phe Gly Trp Ala Ile Tyr Pro Val Gly Tyr Phe Thr Gly
        195                 200                 205

tac ctg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 21-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 21-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tcg ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga ggg gta tgg att gag act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta     336
Ile Asp Trp Leu Leu Thr Val Pro Leu Leu Ile Cys Glu Phe Tyr Leu
            100                 105                 110
```

Figure 22-A

```
att ctt gct gct gca aca aat gtt gct gct ggc ctg ttt aag aaa tta     384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca     432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg     480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt     528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat     576
Asn Thr Ala Ser Pro Ala Val Gln Ser Ala Tyr Asn Thr Met Met Tyr
            180                 185                 190

ata atc atc ttt ggt tgg gca att tat cct gta ggt tat ttc aca ggt     624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat     672
Tyr Leu Met Gly Asp Gly Gly Ser Ala Leu Asn Leu Asn Leu Ile Tyr
    210                 215                 220
```

Figure 22-B

```
aac ctt gct gac ttt gtt aac aag aat cta ttt ggt tta att ata tgg      720
Asn Leu Ala Asp Phe Val Asn Lys Asn Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 22-C

```
atg ggt aaa tta tta cgg ata tta ggt agt gtt att gca ctt cct aca      48
Met Gly Lys Leu Leu Arg Ile Leu Gly Ser Val Ile Ala Leu Pro Thr
1               5                   10                  15

ttt gct gca ggt ggc ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tat atg     240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta     336
Ile Asp Trp Leu Leu Thr Val Pro Leu Leu Ile Cys Glu Phe Tyr Leu
            100                 105                 110
```

Figure 23-A

```
att ctt gct gct gca act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

atc atc atc gtt ggt tgg gcg att tat cct gta ggt tat ttc aca ggt      624
Ile Ile Ile Val Gly Trp Ala Ile Tyr Pro Val Gly Tyr Phe Thr Gly
        195                 200                 205

tac ctg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

Figure 23-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 23-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg     240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta     336
Ile Asp Trp Leu Leu Thr Val Pro Leu Leu Ile Cys Glu Phe Tyr Leu
            100                 105                 110
```

Figure 24-A

```
att ctt gct gct gca act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt gga tca gct ctt aac tta aac ctt att tat      672
Tyr Leu Met Gly Asp Gly Gly Ser Ala Leu Asn Leu Asn Leu Ile Tyr
    210                 215                 220
```

Figure 24-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 24-C

```
atg ggt aaa tta tta ctg ata tta ggt agt gtt att gca ctt cct aca        48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt        96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc       144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act       192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg       240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac       288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta       336
Ile Asp Trp Leu Leu Thr Val Pro Leu Leu Ile Cys Glu Phe Tyr Leu
            100                 105                 110
```

Figure 25-A

```
att ctt gct gct gct act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt gga tca gct ctt aac tta aac ctt att tat      672
Tyr Leu Met Gly Asp Gly Gly Ser Ala Leu Asn Leu Asn Leu Ile Tyr
    210                 215                 220
```

Figure 25-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gct gct gtt aaa gaa tct tct aat gct                              750
Asn Ala Ala Val Lys Glu Ser Ser Asn Ala
                245                 250
```

Figure 25-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tat atg     240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

ata gat tgg tta cta aca gtt cct tta tta ata tgt gaa ttc tac tta     336
Ile Asp Trp Leu Leu Thr Val Pro Leu Leu Ile Cys Glu Phe Tyr Leu
            100                 105                 110
```

Figure 26-A

```
att ctt gcc gct gca act aat gtt gct gga tca tta ttt aag aaa tta      384
Ile Leu Ala Ala Ala Thr Asn Val Ala Gly Ser Leu Phe Lys Lys Leu
        115                 120                 125

ctt gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

atc atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ctt atg ggt gac ggt gga tca gca ctt aac tta aac ctt att tat      672
Tyr Leu Met Gly Asp Gly Gly Ser Ala Leu Asn Leu Asn Leu Ile Tyr
    210                 215                 220
```

Figure 26-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 26-C

```
atg ggt aaa tta tta ctg ata tta ggt agt gtt att gca ctt cct aca      48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt      96
Phe Ala Ala Gly Gly Gly Asp Leu Asp Ala Ser Asp Tyr Thr Gly Val
            20                  25                  30

tct ttt tgg tta gtt aca gct gct cta tta gcg tct act gta ttt ttc     144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act     192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tat atg     240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac     288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta     336
Ile Asp Trp Leu Leu Thr Val Pro Leu Leu Ile Cys Glu Phe Tyr Leu
            100                 105                 110
```

Figure 27-A

```
att ctt gct gct gca act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga ata atg gcg gct tgg cct gca ttc atc gtt gga tgt tta gca tgg      480
Gly Ile Met Ala Ala Trp Pro Ala Phe Ile Val Gly Cys Leu Ala Trp
145                 150                 155                 160

gta tat atg att tat gaa cta tgg gct ggt gaa gga aaa tct gca tgt      528
Val Tyr Met Ile Tyr Glu Leu Trp Ala Gly Glu Gly Lys Ser Ala Cys
                165                 170                 175

aat act gca agt cct gct gta cag tca gct tac aac aca atg atg tat      576
Asn Thr Ala Ser Pro Ala Val Gln Ser Ala Tyr Asn Thr Met Met Tyr
            180                 185                 190

atc atc atc gtt ggt tgg gca att tat cct gta ggt tat ttc aca ggt      624
Ile Ile Ile Val Gly Trp Ala Ile Tyr Pro Val Gly Tyr Phe Thr Gly
        195                 200                 205

tac cta atg ggt gac ggt gga tca gct ctt aat cta aac ctt att tat      672
Tyr Leu Met Gly Asp Gly Gly Ser Ala Leu Asn Leu Asn Leu Ile Tyr
    210                 215                 220
```

Figure 27-B

```
aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

Figure 27-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gta ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg      240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat      288
Arg Gly Val Trp Ile Asp Thr Gly Asp Thr Pro Thr Val Phe Arg Tyr
                85                  90                  95

att gat tgg cta tta act gtt cca tta caa atg gtt gag ttc tat cta      336
Ile Asp Trp Leu Leu Thr Val Pro Leu Gln Met Val Glu Phe Tyr Leu
            100                 105                 110
```

Figure 28-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

ggt tta gct cct gta tta cct gct ttc att ctt ggt atg gct ggt tgg      480
Gly Leu Ala Pro Val Leu Pro Ala Phe Ile Leu Gly Met Ala Gly Trp
145                 150                 155                 160

tta tac atg att tat gag cta cat atg ggt gaa ggt aag gct gct gta      528
Leu Tyr Met Ile Tyr Glu Leu His Met Gly Glu Gly Lys Ala Ala Val
                165                 170                 175

agt act gca agt cct gct gtt aac tct gct tac aat gca atg atg aag      576
Ser Thr Ala Ser Pro Ala Val Asn Ser Ala Tyr Asn Ala Met Met Lys
            180                 185                 190

att att gtt att gga tgg gca att tat cct gct gga tat gct gct ggt      624
Ile Ile Val Ile Gly Trp Ala Ile Tyr Pro Ala Gly Tyr Ala Ala Gly
        195                 200                 205

tac cta atg agt ggt gac ggt gta tac gct tca aac tta aac ctt ata      672
Tyr Leu Met Ser Gly Asp Gly Val Tyr Ala Ser Asn Leu Asn Leu Ile
    210                 215                 220
```

Figure 28-B

```
tat aac ctt gct gac ttt gtt aac aag att cta ttt ggt ttg atc att       720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                           753
Trp Asn Val Ala Val Lys Glu Ser Ser Asn Ala
                245                 250
```

Figure 28-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt     144
Ser Phe Trp Leu Val Thr Ala Gly Met Leu Ala Ala Thr Val Phe Phe
        35                  40                  45

ttt gta gaa aga gac caa gtc agc gct gag tgg aaa act tca ctt act     192
Phe Val Glu Arg Asp Gln Val Ser Ala Glu Trp Lys Thr Ser Leu Thr
    50                  55                  60

gta tct ggt tta att act ggt ata gct ttt tgg cat tat ctc tat atg     240
Val Ser Gly Leu Ile Thr Gly Ile Ala Phe Trp His Tyr Leu Tyr Met
65                  70                  75                  80

aga ggt gtt tgg ata gat act ggt gat acc cca aca gta ttc aga tat     288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta     336
Ile Asp Trp Leu Leu Thr Val Pro Leu Gln Met Val Glu Phe Tyr Leu
            100                 105                 110
```

Figure 29-A

```
att ctt gct gct tgt aca agt gtt gct gct tca tta ttt aag aag ctt    384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct    432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg    480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta    528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg    576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt    624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata    672
Tyr Leu Met Gly Gly Glu Gly Val Tyr Ala Ser Asn Leu Asn Leu Ile
    210                 215                 220
```

Figure 29-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 29-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gcc ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110
```

Figure 30-A

```
att ctt gct gct tgt aca aat gtt gct gct tca tta ttt aag aag ctt      384
Ile Leu Ala Ala Cys Thr Asn Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tgg cct gct ttc att att ggt atg gct gga tgg      480
Gly Leu Ala Pro Val Trp Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac cta aac ctt ata      672
Tyr Leu Met Gly Gly Glu Gly Val Tyr Ala Ser Asn Leu Asn Leu Ile
    210                 215                 220
```

Figure 30-B

```
tat aac ctt gct gac ttt gtt aac aag att cta ttt ggt ttg atc att       720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                           753
Trp Asn Val Ala Val Lys Glu Ser Ser Asn Ala
                245                 250
```

Figure 30-C

```
atg ggt aaa tta tta ctg ata tta ggt agt gct att gcg ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt acg gct ggt atg tta gcg gca act gta ttc ttt     144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act     192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg     240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat     288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta     336
Ile Asp Trp Leu Leu Thr Val Pro Leu Gln Met Val Glu Phe Tyr Leu
            100                 105                 110
```

Figure 31-A

```
att ctt gcc gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca ttg gta atg tta ggt gct gga tct gca ggc gaa gct      432
Leu Ala Gly Ser Leu Val Met Leu Gly Ala Gly Ser Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctc ata      672
Tyr Leu Met Gly Gly Glu Gly Val Tyr Ala Ser Asn Leu Asn Leu Ile
    210                 215                 220
```

Figure 31-B

```
tat aac ctt gct gac ttt gtt aac aag att cta ttt ggt ttg atc att       720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                           753
Trp Asn Val Ala Val Lys Glu Ser Ser Asn Ala
                245                 250
```

Figure 31-C

```
atg ggt aaa tta tta ctg ata tta ggt agt gct att gca ctt cca tca     48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt     96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt    144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act    192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg    240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat    288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta    336
Ile Asp Trp Leu Leu Thr Val Pro Leu Gln Met Val Glu Phe Tyr Leu
            100                 105                 110
```

Figure 32-A

```
att ctt gct gct tgt aca aat gtt gct gct tca tta ttt aag aag ctt      384
Ile Leu Ala Ala Cys Thr Asn Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tgg cct gct ttc att att ggt atg gct gga tgg      480
Gly Leu Ala Pro Val Trp Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg gtg      576
Ser Thr Ala Ser Pro Ala Val Asn Ser Ala Tyr Asn Ala Met Met Val
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac cta aac ctt ata      672
Tyr Leu Met Gly Gly Glu Gly Val Tyr Ala Ser Asn Leu Asn Leu Ile
    210                 215                 220
```

Figure 32-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 32-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt     144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act     192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg     240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat     288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta     336
Ile Asp Trp Leu Leu Thr Val Pro Leu Gln Met Val Glu Phe Tyr Leu
            100                 105                 110
```

Figure 33-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220
```

Figure 33-B

```
tat aac ctt gct gac ctt gtt aac aag att cta ttt ggt ttg atc att      720
Tyr Asn Leu Ala Asp Leu Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 33-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt     144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act     192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg     240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat     288
Arg Gly Val Trp Ile Asp Thr Gly Asp Thr Pro Thr Val Phe Arg Tyr
                85                  90                  95

att gat tgg tta tta act gtt cca tta caa gtg gtt gag ttc tat cta     336
Ile Asp Trp Leu Leu Thr Val Pro Leu Gln Val Val Glu Phe Tyr Leu
            100                 105                 110
```

Figure 34-A

```
att ctt gct gct tgt aca agt gtt gct gct tca tta ttt aag aag ctt     384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct     432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg     480
Gly Leu Ala Pro Val Leu Pro Ala Phe Ile Ile Gly Met Ala Gly Trp
145                 150                 155                 160

tta tac atg att tat gag cta tat atg ggt gaa ggc aag gct gct gta     528
Leu Tyr Met Ile Tyr Glu Leu Tyr Met Gly Glu Gly Lys Ala Ala Val
                165                 170                 175

agt act gca agt cct gct gtt aac cct gca tac aac gca atg atg atg     576
Ser Thr Ala Ser Pro Ala Val Asn Pro Ala Tyr Asn Ala Met Met Met
            180                 185                 190

att att gtt gtt gga tgg gca att tat cct gct gga tat gct gct ggt     624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata     672
Tyr Leu Met Gly Gly Glu Gly Val Tyr Ala Ser Asn Leu Asn Leu Ile
    210                 215                 220
```

Figure 34-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 34-C

```
atg ggt aaa tta tta ctg ata tta ggt agt gct att gca ctt cca tca     48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt     96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gta ttc ttt    144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act    192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg    240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat    288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta    336
Ile Asp Trp Leu Leu Thr Val Pro Leu Gln Met Val Glu Phe Tyr Leu
            100                 105                 110
```

Figure 35-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

ggt tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta cat atg ggt gaa ggt aag gct gct gta      528
Leu Tyr Met Ile Tyr Glu Leu His Met Gly Glu Gly Lys Ala Ala Val
                165                 170                 175

agt act gca agt cct gct gtt aac tct gca tac aac gca atg atg aag      576
Ser Thr Ala Ser Pro Ala Val Asn Ser Ala Tyr Asn Ala Met Met Lys
            180                 185                 190

att att gtt att gga tgg gca att tat cct gct gga tat gct gct ggt      624
Ile Ile Val Ile Gly Trp Ala Ile Tyr Pro Ala Gly Tyr Ala Ala Gly
        195                 200                 205

tac cta atg agt ggt gac ggt gta tac gct tca aac tta aac ctt ata      672
Tyr Leu Met Ser Gly Asp Gly Val Tyr Ala Ser Asn Leu Asn Leu Ile
    210                 215                 220
```

Figure 35-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 35-C

```
atg ggt aaa tta tta ctg ata tta ggt agt gct att gca ctt cca tca      48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt      96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt     144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act     192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg     240
Val Ser Gly Leu Ile Thr Gly Ile Ala Phe Trp His Tyr Leu Tyr Met
65                  70                  75                  80

aga ggt gtt tgg ata gat act ggt gat acc cca aca gta ttc aga tat     288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta     336
Ile Asp Trp Leu Leu Thr Val Pro Leu Gln Met Val Glu Phe Tyr Leu
            100                 105                 110
```

Figure 36-A

```
att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

cta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggc gta tac gct tca aac tta aac ctt ata      672
Tyr Leu Met Gly Gly Glu Gly Val Tyr Ala Ser Asn Leu Asn Leu Ile
    210                 215                 220
```

Figure 36-B

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

Figure 36-C

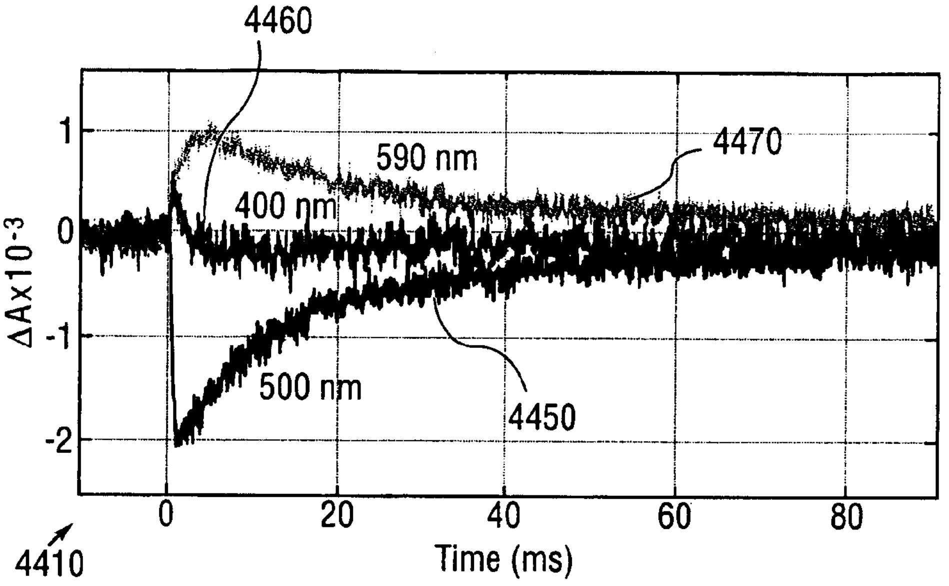
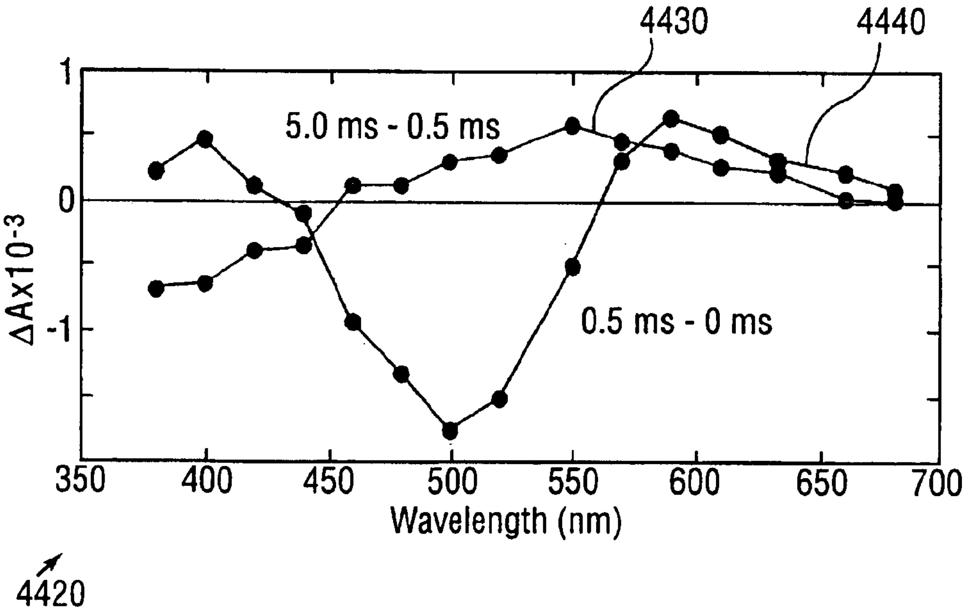
Figure 44

LIGHT-DRIVEN ENERGY GENERATION USING PROTEORHODOPSIN

CROSS-REFERENCE TO RELATED APPLICATIONS

This application is cross-referenced to and claims priority from U.S. Provisional application No. 60/201,602 filed May 3, 2000, which is hereby incorporated by reference.

STATEMENT REGARDING FEDERALLY SPONSORED RESEARCH OR DEVELOPMENT

This invention was supported in part by grant number OCE 0001619 from the National Science Foundation (NSF). The U.S. government has certain rights in the invention.

STATEMENT TO COMPUTER DISK AND SEQUENCE LISTING

This application includes a sequence listing of 65 sequences and a computer disk labeled "Sequence Listing for application entitled "Light-driven energy generation using proteorhodopsin" by Edward F. DeLong and Oded Beja" containing files "MBA101-SEQLIST.prj", dated "Apr. 23, 2001" with 174,089 bytes, which is the PatentIn project file generated using PatentIn Version 3.0 software provided by the USPTO, and "MBA101-SEQLIST.txt", dated "Apr. 23, 2001" with 323,739 bytes, which is the generated sequence listing from the PatentIn project file MBA101-SEQLIST.prj using PatentIn Version 3.0 software, all which are herein incorporated. The information recorded in computer readable format on the incorporated computer disk labeled "Sequence Listing" containing files "MBA101-SEQLIST.prj " and "MBA101-SEQLIST.txt" are identical to the incorporated written sequence listing.

FIELD OF THE INVENTION

The present invention relates generally to gene expression of functional recombinant proteins in bacteria. More particularly, the present invention relates to proteorhodopsin genes and proteins that function as a light-driven energy generator in *Escherichia coli* (*E. coli*) and other bacteria.

BACKGROUND ART

Retinal (vitamin A aldehyde) is a chromophore that binds integral membrane proteins (opsins) to form light-absorbing pigments called rhodopsins. Rhodopsins are currently known to belong to two distinct protein families. The visual rhodopsins, found in the eye throughout the animal kingdom, are photosensory pigments. Archaeal rhodopsins, found in extreme halophilic environments, function as light-driven protons pumps (bacteriorhodopsins), chloride ion pumps (halorhodopsins), or photosensory receptors (sensory rhodopsins). The two protein families show no significant sequence similarity and may have different origins. They do, however, share identical topologies characterized by seven transmembrane α-helices that form a pocket in which retinal is covalently linked, as a pronated Schiff base (helix G).

The archaeal rhodopsins are able to generate a photocycle which produces a chemiosmotic membrane potential in response to light, as such light energy is converted into biochemical energy. Recently, a protein with high sequence similarity to the archaeal rhodopsins has also been retrieved in the eukaryote Neurospora crassa (J. A. Bieszke et al., *Proceedings of National Academy of Sciences USA* 96:8034, 1999). The eucaryal rhodopsin formed a photochemically reactive pigment when bound to all-trans retinal and exhibited photocycle kinetics similar to those of archaeal sensory rhodopsins (J. A. Bieszke et al., *Biochemistry* 38:14138, 1999). To date, however, no rhodopsin-like sequences have been reported in members of the domain Bacteria, and no light-driven proton pumps based on rhodopsin have ever before been functionally expressed in *E coli.*

The phototropic conversion of light energy into biochemical energy using bacteriorhodopsin can be harnessed for a variety of processes and applications, such as bio-electronic applications and bio-materials, as has been reported in U.S. Pat. No. 5,757,525 for optical devices, U.S. Pat. No. 5,854,710 for optical Fourier processing, and U.S. Pat. No. 5,470,690 for optical information storage. Bacteriorhodopsin in bio-electronic applications is aimed to interface, integrate, or substitute the silicon based microelectronics systems as well as molecular devices. Bacteriorhodopsin as a bio-material is integrated, for instance, in optical films for light mediated computer memory applications and pattern recognition.

Previously, archaeal rhodopsins capable of generating a chemiosmotic membrane potential in response to light had only been found in halophilic archaea. Therefore, rhodopsins that originate from archaea adapted to highly saline environments cannot be functionally expressed in *E. coli*. Finally, the isolation and cultivation of halorhodopsins is an elaborate process. At present one does not foresee an economic utilization possible for this process (e.g. U.S. Pat. No. 5,290,699).

Accordingly, as one skilled in the art might readily acknowledge, there is a strong need to retrieve and provide rhodopsin-like sequences from naturally occurring members of the domain Bacteria.

OBJECTS AND ADVANTAGES

In light of the above, it is the primary objective of the present invention to provide rhodopsin-like (also referred to here as "proteorhodopsin") sequences from naturally occurring members of the domain Bacteria. More specifically, it is the objective of the present invention to provide a method to retrieve proteorhodopsin genes from DNA of naturally occurring bacteria that encodes DNA sequence for proteorhodopsin proteins.

It is another objective of the present invention to provide proteorhodopsin-specific polymerase chain reaction primers that amplify the proteorhodopsin-containing gene from a DNA sample of naturally occurring bacteria.

It is yet another objective of the present invention to produce variants of a proteorhodopsin gene using the same proteorhodopsin-specific polymerase chain reaction primers by amplifying a proteorhodopsin-containing gene from of a mixed sample of naturally occurring bacteria.

It is still another objective of the present invention to provide an expression vector that produces a proteorhodopsin protein in *E. coli* and other bacteria.

It is another objective of the present invention to provide a light-driven energy generator in which the functional properties of proteorhodopsin are utilized. These properties include the ability to integrate within a host, for instance a cell membrane of *E. coli*, making an integrated proteorhodopsin protein, and the ability to bind retinal, making a light absorbing pigment.

It is another objective of the present invention to provide a light source and illuminate the light absorbing pigment to convert light energy into biochemical energy.

It is another objective of the present invention to provide a mediator and mediate the biochemical energy into electrical energy.

It is another objective of the present invention to provide methods to manipulate the kinetics of the light-driven energy generator.

The advantage of the present invention over the prior art is that it is not restricted to operate in halophilic archaea and could therefore be functionally expressed in *E. coli* and other bacteria. Accordingly, another advantage of the present invention is that it provides for a fast and cheap production method that allows for mass production of functionally active proteorhodopsin.

SUMMARY

The present invention provides proteorhodopsin gene and protein sequences retrieved from samples of naturally occurring members of the domain Bacteria. More specifically, the present invention provides a method for the retrieval and amplification of proteorhodopsin genes from DNA samples of naturally occurring marine bacteria. In accordance with several exemplary embodiments of the present invention, DNA samples were obtained from naturally occurring bacteria such as, for instance, marine proteobacteria, SAR86 bacteria, or recombinant DNA libraries containing naturally occurring bacteria. The present invention provides proteorhodopsin-specific polymerase chain reaction (PCR) primers to amplify a proteorhodopsin gene from DNA samples of these marine bacteria. The present invention also provides a device and method for the placement of proteorhodopsin genes in an expression vector to produce functional proteorhodopsin proteins in *E. coli* and other bacteria.

Accordingly, the present invention provides a method to produce and obtain variants of proteorhodopsin genes and proteins. The same proteorhodopsin-specific polymerase chain reaction primers amplify different variants of proteorhodopsin-containing genes from a mixed sample of naturally occurring bacteria. As one skilled in the art might readily acknowledge, these variants of a proteorhodopsin gene produce functional variations in the photocycle kinetics of the proteorhodopsin protein.

Furthermore, the present invention provides a light-driven energy generator that utilizes proteorhodopsin to convert light-energy into biochemical energy. This light-driven energy generator takes advantage of the functional properties of the proteorhodopsin protein once expressed in, for example, *E. coli* or other bacteria as is described in exemplary embodiments. These properties include the ability to integrate within a host such as, for instance, a cell membrane of *E. coli* or other Bacteria, and thereby making an integrated proteorhodopsin protein or integrated cell membrane protein. These properties also include the ability to bind retinal and thereby making a light absorbing pigment. Illuminating the light absorbing pigment with a light source converts light energy into biochemical energy. Finally, the biochemical energy can be mediated into electrical energy by a mediator.

In accordance with exemplary embodiments, the present invention enables one skilled in the art to manipulate the kinetics of the proteorhodopsin protein photocycle once it is operational in the light-driven energy generator. In particular, the present invention provides examples in which the light source characteristics are manipulated. Examples are the manipulation of the delivery of fast-light pulses and/or the delivery of light at different wavelengths. The present invention also provides examples in which incremental additions of retinal influences the function of the light-driven energy generator. In addition, a proteorhodopsin gene or protein variant can be selected to determine an absorption spectra of the light absorbing pigment to change the kinetics of the light energy generator, for instance to meet a design/functional criteria of an application wherein proteorhodopsin is utilized.

BRIEF DESCRIPTION OF THE FIGURES

The patent or application file contains at least one drawing executed in color. Copies of this patent or patent application publication with color drawing(s) will be provided by the Office upon request and payment of the necessary fee.

The objectives and advantages of the present invention will be understood by reading the following detailed description in conjunction with the drawings, in which:

FIG. 2 provides a nucleotide sequence of polymerase chain reaction primer 1 (Sequence ID No:2) used to amplify a proteorhodopsin gene.

FIG. 3 provides a nucleotide sequence of polymerase chain reaction primer 2 (Sequence ID No:3) used to amplify a proteorhodopsin gene.

FIG. 4 provides the nucleotide sequence of the proteorhodopsin gene (Sequence ID No:4) amplified from clone EBAC31A8 (Sequence ID No:1) using PCR primers 1 (Sequence ID No:2) and 2 (Sequence ID No:3), and the deduced amino acid sequence (Sequence ID No:5) of the proteorhodopsin gene Sequence ID No:4 amplified from clone EBAC31A8 (Sequence ID No:1).

FIG. 6 provides the nucleotide sequence of the proteorhodopsin gene (Sequence ID No:8) amplified from clone EBAC40E8 using PCR primers 1 (Sequence ID No:2) and 2 (Sequence No:3), and the deduced amino acid sequence (Sequence ID No:9) of the proteorhodopsin gene Sequence ID No:8 amplified from clone EBAC40E8.

FIG. 7 provides the nucleotide sequence of the proteorhodopsin gene (Sequence ID No:10) amplified from clone EBAC41B4 using PCR primers 1 (Sequence ID No:2) and 2 (Sequence No:3), and the deduced amino acid sequence (Sequence ID No:11) of the proteorhodopsin gene Sequence ID No:7 amplified from clone EBAC41B4.

FIG. 8 provides the nucleotide sequence of the proteorhodopsin gene (Sequence ID No:12) amplified from clone EBAC64A5 using PCR primers 1 (Sequence ID No:2) and 2 (Sequence No:3), and the deduced amino acid sequence (Sequence ID No:13) of the proteorhodopsin gene Sequence ID No:12 amplified from clone EBAC64A5.

FIG. 9 provides a variants map of the DNA sequences of the proteorhodopsin gene with Sequence ID No:4, Sequence ID No:8, Sequence ID No:10, and Sequence ID No:12 that were amplified from clone EBAC38A8, EBAC40E8, EBAC41B4 and EBAC64A5 respectively using the proteorhodopsin-specific PCR primer 1 (Sequence ID No:2) and 2 (Sequence ID No:3). Dots represent sequences having identical sequence as those in Sequence ID No:4.

FIG. 10 provides a variant map of the deduced amino acid sequences encoded by the proteorhodopsin gene with Sequence ID No:4, Sequence ID No:8, Sequence ID No:10, and Sequence ID No:12 that were amplified from respectively EBAC38A8, EBAC40E8, EBAC41B4 and EBAC64A5 using the proteorhodopsin-specific primer 1 (Sequence ID No:2) and 2 (Sequence ID No:3). Lower case represents the PCR primer sequence region. Dots represent residues having identical sequence as those in Sequence ID No:5.

FIG. 11 provides the nucleotide sequence of the proteorhodopsin gene (Sequence ID No:14) amplified from clone HOT0m1 using PCR primers 1 (Sequence ID No:2) and 2 (Sequence No:3), and the deduced amino acid sequence (Sequence ID No:15) of the proteorhodopsin gene Sequence ID No:14 amplified from clone HOT0m1.

FIG. 12 provides the nucleotide sequence of the proteorhodopsin gene (Sequence ID No:16) amplified from clone HOT75m1 using PCR primers 1 (Sequence ID No:2) and 2 (Sequence No:3), and the deduced amino acid sequence (Sequence ID No:17) of the proteorhodopsin gene Sequence ID No:16 amplified from clone HOT75m1.

FIG. 13 provides the nucleotide sequence of the proteorhodopsin gene (Sequence ID No:18) amplified from clone HOT75m3 using PCR primers 1 (Sequence ID No:2) and 2 (Sequence No:3), and the deduced amino acid sequence (Sequence ID No:19) of the proteorhodopsin gene Sequence ID No:18 amplified from clone HOT75m3.

FIG. 14 provides the nucleotide sequence of the proteorhodopsin gene (Sequence ID No:20) amplified from clone HOT75m4 using PCR primers 1 (Sequence ID No:2) and 2 (Sequence No:3), and the deduced amino acid sequence (Sequence ID No:21) of the proteorhodopsin gene Sequence ID No:20 amplified from clone HOT75m4.

FIG. 15 provides the nucleotide sequence of the proteorhodopsin gene (Sequence ID No:22) amplified from clone HOT75m8 using PCR primers 1 (Sequence ID No:2) and 2 (Sequence No:3), and the deduced amino acid sequence (Sequence ID No:23) of the proteorhodopsin gene Sequence ID No:22 amplified from clone HOT75m8.

FIG. 16 provides the nucleotide sequence of the proteorhodopsin gene (Sequence ID No:24) amplified from clone MB0m1 using PCR primers 1 (Sequence ID No:2) and 2 (Sequence No:3), and the deduced amino acid sequence (Sequence ID No:25) of the proteorhodopsin gene Sequence ID No:24 amplified from clone MB0m1.

FIG. 17 provides the nucleotide sequence of the proteorhodopsin gene (Sequence ID No:26) amplified from clone MB0m2 using PCR primers 1 (Sequence ID No:2) and 2 (Sequence No:3), and the deduced amino acid sequence (Sequence ID No:27) of the proteorhodopsin gene Sequence ID No:26 amplified from clone MB0m2.

FIG. 18 provides the nucleotide sequence of the proteorhodopsin gene (Sequence ID No:28) amplified from clone MB20m2 using PCR primers 1 (Sequence ID No:2) and 2 (Sequence No:3), and the deduced amino acid sequence (Sequence ID No:29) of the proteorhodopsin gene Sequence ID No:28 amplified from clone MB20m2.

FIG. 19 provides the nucleotide sequence of the proteorhodopsin gene (Sequence ID No:30) amplified from clone MB20m5 using PCR primers 1 (Sequence ID No:2) and 2 (Sequence No:3), and the deduced amino acid sequence (Sequence ID No:31) of the proteorhodopsin gene Sequence ID No:30 amplified from clone MB20m5.

FIG. 20 provides the nucleotide sequence of the proteorhodopsin gene (Sequence ID No:32) amplified from clone MB20m12 using PCR primers 1 (Sequence ID No:2) and 2 (Sequence No:3), and the deduced amino acid sequence (Sequence ID No:33) of the proteorhodopsin gene Sequence ID No:32 amplified from clone MB20m12.

FIG. 21 provides the nucleotide sequence of the proteorhodopsin gene (Sequence ID No:34) amplified from clone MB40m1 using PCR primers 1 (Sequence ID No:2) and 2 (Sequence No:3), and the deduced amino acid sequence (Sequence ID No:35) of the proteorhodopsin gene Sequence ID No:34 amplified from clone MB40m1.

FIG. 22 provides the nucleotide sequence of the proteorhodopsin gene (Sequence ID No:36) amplified from clone MB40m5 using PCR primers 1 (Sequence ID No:2) and 2 (Sequence No:3), and the deduced amino acid sequence (Sequence ID No:37) of the proteorhodopsin gene Sequence ID No:36 amplified from clone MB40m5.

FIG. 23 provides the nucleotide sequence of the proteorhodopsin gene (Sequence ID No:38) amplified from clone MB40m12 using PCR primers 1 (Sequence ID No:2) and 2 (Sequence No:3), and the deduced amino acid sequence (Sequence ID No:39) of the proteorhodopsin gene Sequence ID No:38 amplified from clone MB40m12.

FIG. 24 provides the nucleotide sequence of the proteorhodopsin gene (Sequence ID No:40) amplified from clone MB100m5 using PCR primers 1 (Sequence ID No:2) and 2 (Sequence No:3), and the deduced amino acid sequence (Sequence ID No:41) of the proteorhodopsin gene Sequence ID No:40 amplified from clone MB100m5.

FIG. 25 provides the nucleotide sequence of the proteorhodopsin gene (Sequence ID No:42) amplified from clone MB100m7 using PCR primers 1 (Sequence ID No:2) and 2 (Sequence No:3), and the deduced amino acid sequence (Sequence ID No:43) of the proteorhodopsin gene Sequence ID No:42 amplified from clone MB100m7.

FIG. 26 provides the nucleotide sequence of the proteorhodopsin gene (Sequence ID No:44) amplified from clone MB100m9 using PCR primers 1 (Sequence ID No:2) and 2 (Sequence No:3), and the deduced amino acid sequence (Sequence ID No:45) of the proteorhodopsin gene Sequence ID No:44 amplified from clone MB100m9.

FIG. 27 provides the nucleotide sequence of the proteorhodopsin gene (Sequence ID No:46) amplified from clone MB100m10 using PCR primers 1 (Sequence ID No:2) and 2 (Sequence No:3), and the deduced amino acid sequence (Sequence ID No:47) of the proteorhodopsin gene Sequence ID No:46 amplified from clone MB100m10.

FIG. 28 provides the nucleotide sequence of the proteorhodopsin gene (Sequence ID No:48) amplified from clone PALB1 using PCR primers 1 (Sequence ID No:2) and 2 (Sequence No:3), and the deduced amino acid sequence (Sequence ID No:49) of the proteorhodopsin gene Sequence ID No:48 amplified from clone PALB1.

FIG. 29 provides the nucleotide sequence of the proteorhodopsin gene (Sequence ID No:50) amplified from clone PALB2 using PCR primers 1 (Sequence ID No:2) and 2 (Sequence No:3), and the deduced amino acid sequence (Sequence ID No:51) of the proteorhodopsin gene Sequence ID No:50 amplified from clone PALB2.

FIG. 30 provides the nucleotide sequence of the proteorhodopsin gene (Sequence ID No:52) amplified from clone PALB5 using PCR primers 1 (Sequence ID No:2) and 2 (Sequence No:3), and the deduced amino acid sequence (Sequence ID No:53) of the proteorhodopsin gene Sequence ID No:52 amplified from clone PALB5.

FIG. 31 provides the nucleotide sequence of the proteorhodopsin gene (Sequence ID No:54) amplified from clone PALB7 using PCR primers 1 (Sequence ID No:2) and 2 (Sequence No:3), and the deduced amino acid sequence (Sequence ID No:55) of the proteorhodopsin gene Sequence ID No:54 amplified from clone PALB7.

FIG. 32 provides the nucleotide sequence of the proteorhodopsin gene (Sequence ID No:56) amplified from clone PALB6 using PCR primers 1 (Sequence ID No:2) and 2 (Sequence No:3), and the deduced amino acid sequence (Sequence ID No:57) of the proteorhodopsin gene Sequence ID No:56 amplified from clone PALB6.

FIG. 33 provides the nucleotide sequence of the proteorhodopsin gene (Sequence ID No:58) amplified from clone PALB8 using PCR primers 1 (Sequence ID No:2) and 2 (Sequence No:3), and the deduced amino acid sequence (Sequence ID No:59) of the proteorhodopsin gene Sequence ID No:58 amplified from clone PALB8.

FIG. 34 provides the nucleotide sequence of the proteorhodopsin gene (Sequence ID No:60) amplified from clone PALE1 using PCR primers 1 (Sequence ID No:2) and 2 (Sequence No:3), and the deduced amino acid sequence (Sequence ID No:61) of the proteorhodopsin gene Sequence ID No:60 amplified from clone PALE1.

FIG. 35 provides the nucleotide sequence of the proteorhodopsin gene (Sequence ID No:62) amplified from clone PALE6 using PCR primers 1 (Sequence ID No:2) and 2 (Sequence No:3), and the deduced amino acid sequence (Sequence ID No:63) of the proteorhodopsin gene Sequence ID No:62 amplified from clone PALE6.

FIG. 36 provides the nucleotide sequence of the proteorhodopsin gene (Sequence ID No:64) amplified from clone PALE7 using PCR primers 1 (Sequence ID No:2) and 2 (Sequence No:3), and the deduced amino acid sequence (Sequence ID No:65) of the proteorhodopsin gene Sequence ID No:64 amplified from PALE7.

FIG. 44 provides an example of laser flash-induced absorbance changes in suspensions of *E. coli* membranes containing proteorhodopsin.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

Proteorhodopsin

The present invention provides rhodopsin-like gene and protein sequences retrieved from naturally occurring members of the domain Bacteria. More specifically, the present invention provides a method for the retrieval and amplification of proteorhodopsin genes from DNA samples of naturally occurring marine bacteria. In accordance with exemplary embodiments of the present invention, DNA samples were obtained from naturally occurring marine bacteria such as bacteria from the SAR86 group. Provided as an exemplary embodiment of the SAR86 group, DNA samples were obtained from a bacterioplankton Bacterial Artificial Chromosome (BAC) clone BAC31A8 (also referred to as EBAC31A08). In general, as will be appreciated by those of ordinary skill in the art, suitable DNA samples can also be obtained from other sources, e.g., from a marine environment or from a recombinant DNA library containing genomic fragments of samples of naturally occurring bacteria.

Figure 1:
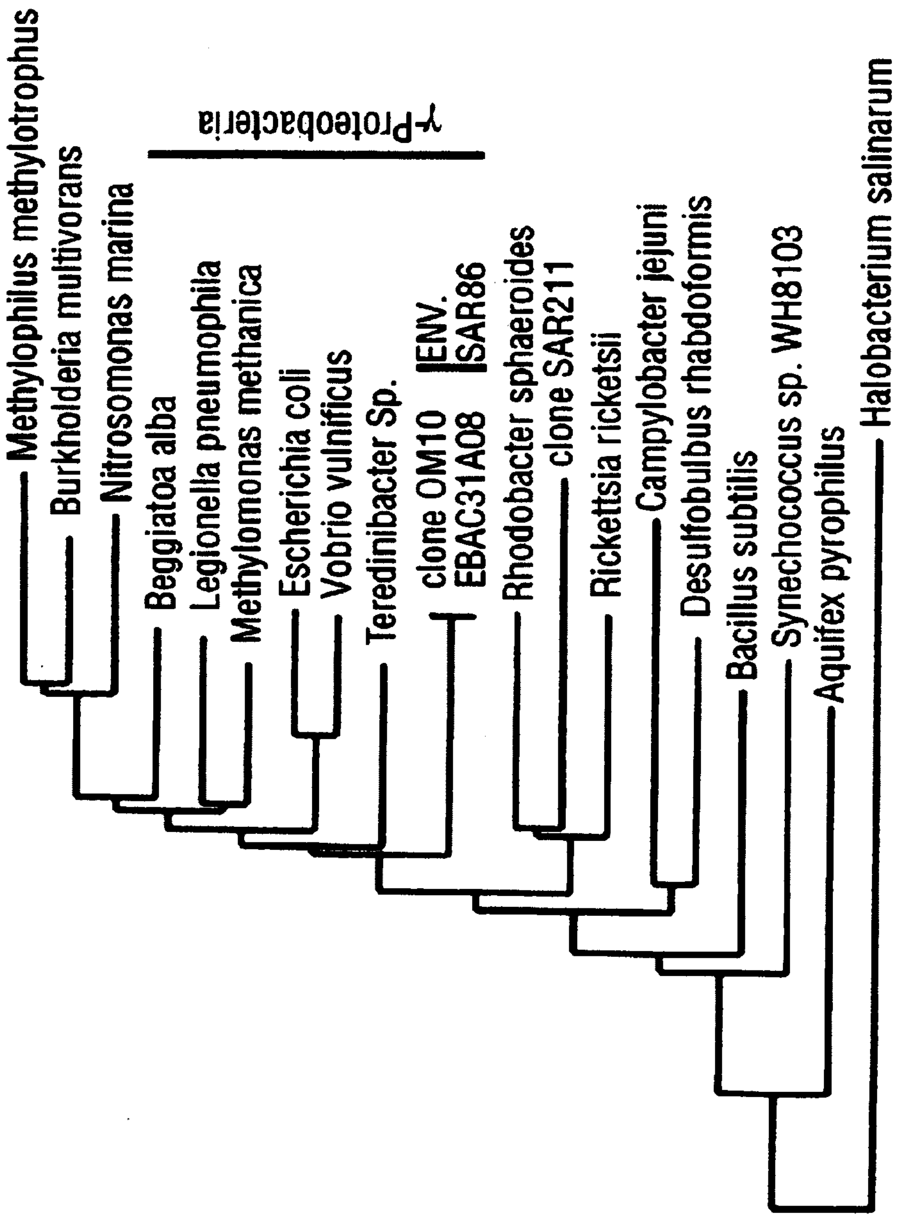
FIG. 1 illustrates the phylogenetic tree of bacterial 16S rRNA gene sequences including that encoded on the 130 kb bacterioplankton BAC clone (EBAC31A8).

FIG. 1 shows the phylogenetic tree of bacterial 16S rRNA gene sequences including that encoded on the EBAC31A8. FIG. 1 also shows the relationship of EBAC31A8 to the SAR86 bacteria group as well as to the gamma-proteobacteria group. A subclone shotgun library was constructed from BAC clone 31A8, and subclones were sequenced in both directions on the MegaBACE 1000 capillary array electrophoresis DNA sequencing instrument (Molecular Dynamics, Sunnyvale, Calif.). Sequence analysis of a 130-kb genomic DNA that encodes the ribosomal RNA operon from BAC31A8, reveals an open reading frame encoding a proteorhodopsin. In an exemplary embodiment, the contiguous sequence was assembled using SEQUENCHER 3.1.1 software (Gene Codes Co., Ann Arbor, Mich.). Other sequencing techniques can also be used, as will be recognized by those skilled in the art. The sequence of the proteorhodopsin-containing contig has been deposited in GenBank under accession #AF279106 and deposit date Oct. 23, 2000. Appendix A, hereby incorporated, shows the nucleotide sequence of the BAC clone BAC31A8 (Sequence ID No:1) which contains the 130 kilobases genomic DNA from a naturally occurring marine bacterium.

Figure 3:
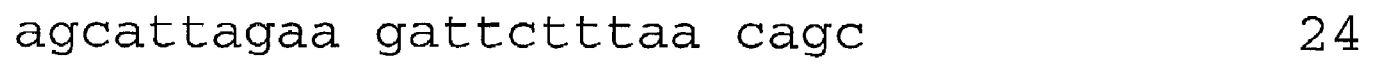

Proteorhodopsin was amplified from the 130 kilobase bacterioplankton BAC clone 31A8 (Sequence ID No:1) by polymerase chain reaction (PCR), using the proteorhodopsin-specific primers 5'-aCCATGGgtaaattattactgatattagg-3' (Sequence ID No:2 and shown in FIG. 2) and 5'-agcattagaagattctttaacagc-3' (Sequence ID No:3 and shown in FIG. 3). References for PCR are, for instance, *The Polymerase Chain Reaction*, Mullis et al., Ed. (Birkhauser, Boston, 1994) and U.S. Pat. Nos. 4,683,195 and 4,683,202 to Mullis et al. The proteorhodopsin-specific PCR primers include the addition of 3 nucleotides that encoded one amino acid not found in the native gene sequence of clone BAC31A8 (Sequence ID No:6), in the second amino acid position which is a glycine located on the $2^{nd}$ codon ("GGT"). Therefore, compare the second amino acid position in the Sequence ID No:5 using PCR primers 1 and 2 with the native Sequence ID no: 7. This addition of one non-native amino acid created a new restriction endonuclease site (NcoI site) not present in the native sequence. This allowed subcloning of the amplified fragment into the NcoI restriction site of an expression vector pBAD TOPO TA Cloning® Kit (Invitrogen, La Jolla, Calif.). The present invention is not limited to the use of this type of expression vector and other expression vectors could also be used.

FIG. 4 shows the nucleotide sequence of the proteorhodopsin gene (Sequence ID No:4) that results from amplification of the proteorhodopsin-containing DNA in BAC31A8 using proteorhodopsin-specific PCR primers Sequence ID No:2 and Sequence No:3. FIG. 4 also shows the deduced amino acid sequences (Sequence ID No:5) encoded by the proteorhodopsin gene (Sequence ID No:4).

Figure 5:
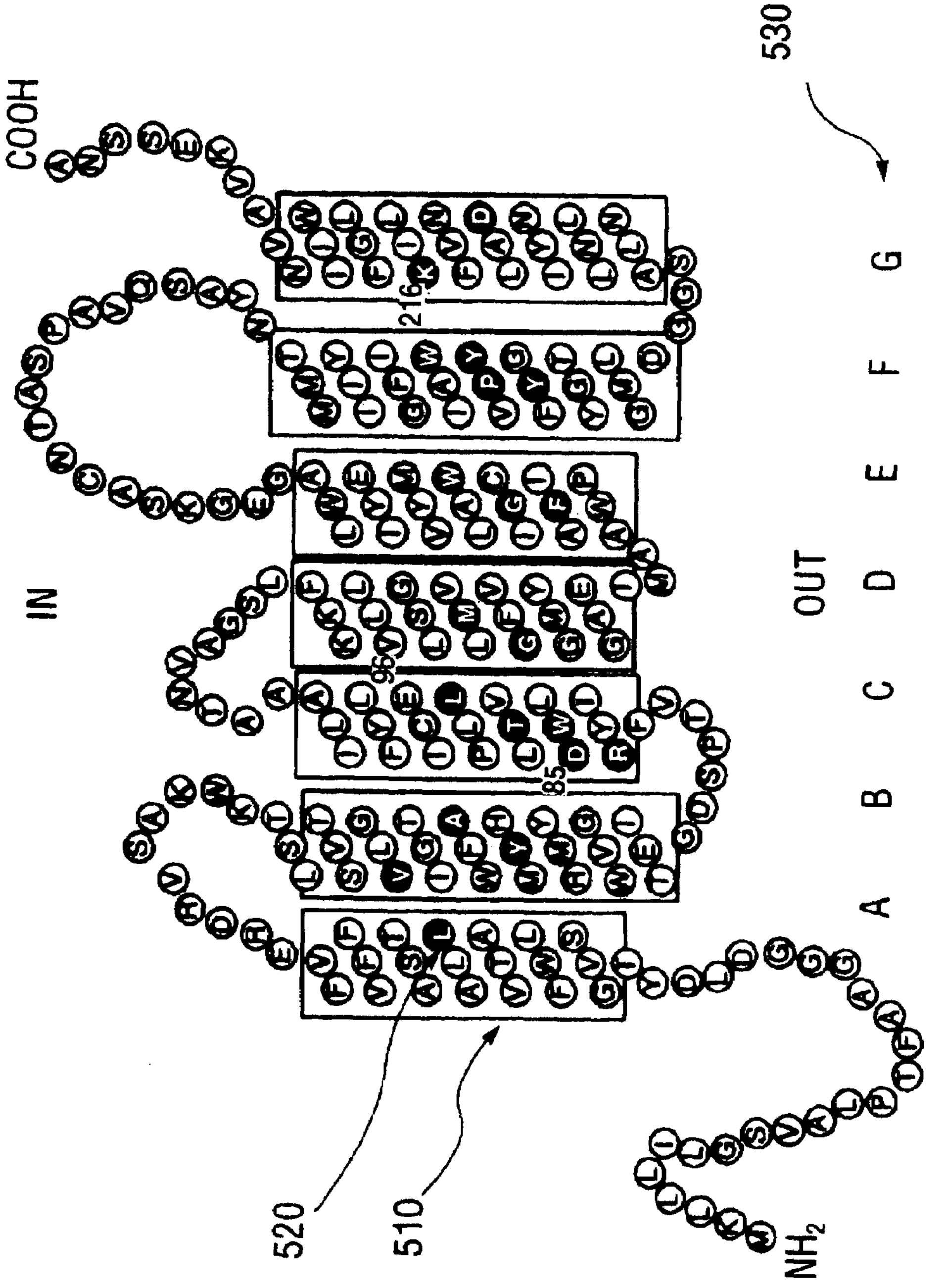
FIG. 5 provides a map of the secondary structure of the proteorhodopsin protein (Sequence ID No:7). Single letter amino acid codes are used (according to J. Sasaki and J. L. Spudich, Biophys. J. 75:2435, 1998). Predicted retinal binding pocket residues are marked in black.

FIG. 5 shows an exemplary embodiment of a secondary structure of proteorhodopsin after it has been folded in a cell membrane 510 and bonded with retinal 520. FIG. 5 shows the native proteorhodopsin gene (Sequence ID No:6) obtained from clone BAC31A8 and encodes a proteorhodopsin protein of 249 amino acids with a molecular weight of 27 kD (Sequence ID No:7). In FIG. 5, 530 indicates seven transmembrane domains, a typical feature of the rhodopsin protein family, that aligned well with the corresponding helices of the archaeal rhodopsins. FIG. 5 also shows the amino acid residues that form a retinal binding pocket indicated by 520. Although the proteorhodopsin proteins shown in FIGS. 4 and 5 both originate from BAC31A8, they differ with respect to the second amino acid position.

The reason is that the proteorhodopsin-specific PCR primers that were used to amplify the proteorhodopsin gene from BAC31A8 (which resulted in proteorhodopsin protein as in FIG. 4; Sequence ID No:5) included the addition of 3 nucleotides. These 3 nucleotides encoded one amino acid not found in the native gene sequence (Sequence ID No:6), in the second amino acid position which is a glycine located on the $2^{nd}$ codon ("GGT"). Proteorhodopsin protein (Sequence ID No:7) as shown in FIG. 5 originates from the native gene sequence without the addition of the 3 nucleotides. As mentioned above, the addition of the 3 nucleotides created a new restriction endonuclease site (NcoI site) that was not present in the native sequence and thereby allowed the amplified fragment to be subcloned into the NcoI site of the expression vector.

In the exemplary embodiment presented above, PCR primers with Sequence ID No:2 and Sequence ID No:3 were used. In general, the present invention provides a method for designing different proteorhodopsin-specific PCR primers that are all capable of amplifying a proteorhodopsin gene from DNA samples of naturally occurring microbial populations by polymerase chain reaction. In designing these primers one first needs to determine a DNA sequence of a proteorhodopsin gene. Then one can design oligodeoxynucleotide primers with a Watson-Crick base pair complementary to 5' and 3' ends of the proteorhodopsin gene.

Variants of Proteorhodopsin

In the previous section, an exemplary embodiment is provided of a proteorhodopsin gene and protein. The present invention also provides the retrieval of genetic variations of proteorhodopsin from naturally occurring genetic variations in naturally occurring bacterial populations. These genetic variations in proteorhodopsin sequences result in functional variations in the proteorhodopsin proteins as is discussed below.

The present invention enables one skilled in the art to use the same proteorhodopsin-specific PCR primers as shown in FIGS. 2 and 3 to successfully amplify different sequence variants from DNA originating from mixed naturally occurring bacterial populations when it is compared to for instance the proteorhodopsin gene as shown in FIG. 4. As mentioned above, different proteorhodopsin-specific PCR primers could be used to amplify genetic variants of proteorhodopsin.

FIGS. 6–8 show exemplary embodiments of three different and unique variants of the proteorhodopsin gene that were retrieved from a recombinant DNA library of other naturally occurring bacteria (i.e. the bacterial artificial chromosome library (BAC)). In general, genetic variants could be obtained from different DNA libraries containing naturally occurring bacteria as well as from samples of naturally occurring bacteria. FIG. 6 shows the variant of the proteorhodopsin gene sequence (Sequence ID No:8) that is amplified from the BAC clone 40 (BAC40E8) with the same proteorhodopsin-specific PCR primers as provided in Sequence ID No:2 and 3. Accordingly, FIG. 6 also shows the deduced amino acid sequence (Sequence ID No:9) of the genetic variant of proteorhodopsin shown in FIG. 6. FIG. 7 shows the variant of the proteorhodopsin gene sequence (Sequence ID No:10) that is amplified from the BAC clone 41 (BAC41B4) with the same proteorhodopsin-specific PCR primers as provided in Sequence ID No:2 and 3. Accordingly, FIG. 7 also shows the deduced amino acid sequence (Sequence ID No:11) of the genetic variant of proteorhodopsin shown in FIG. 7. FIG. 8 shows the variant of the proteorhodopsin gene sequence (Sequence ID No:12) that is amplified from the BAC clone 64 (BAC64A5) with the same proteorhodopsin-specific PCR primers as provided in Sequence ID No:2 and 3. Accordingly, FIG. 8 also shows the deduced amino acid sequence (Sequence ID No:13) of the genetic variant of proteorhodopsin shown in FIG. 8.

FIG. 9 provides a variants map of the nucleotide sequences of the proteorhodopsin gene Sequence ID No:4, Sequence ID No:8, Sequence ID No:10, and Sequence ID No:12 amplified from respectively BAC31A8, BAC40E8, BAC41B4 and BAC64A5 using the proteorhodopsin-specific PCR primers Sequence ID No:2 and Sequence ID No:3. In FIG. 9 lower case letters represent the PCR primer sequence region. Dots represent residues having identical sequence as those in Sequence ID No:4. These proteorhodopsin gene sequences differ by as much as 31 nucleotides as is shown in FIG. 10. FIG. 10 provides a variant map of the deduced amino acid sequences of the proteorhodopsin genes shown in FIG. 9.

Using the same proteorhodopsin-specific PCR primers, as for instance shown in FIGS. 2 and 3, proteorhodopsin genes were also amplified from bacterioplankton extracts. As mentioned above, any proteorhodopsin-specific PCR primer can be used. These bacterioplankton extracts include those from the Monterey Bay (referred to as MB clones), the Southern Ocean (Palmer Station, referred to as PAL clones), and waters of the central North Pacific Ocean (Hawaii Ocean Time series station, referred to as HOT clones).

FIGS. 11–36 show exemplary embodiments of different and unique variants of proteorhodopsin that were retrieved from the MB clones, PAL clones, and HOT clones. FIGS. 11–36 each show a variant of a proteorhodopsin gene sequence that is amplified with the same proteorhodopsin-specific PCR primers as provided in Sequence ID No:2 and Sequence ID No:3 from respectively clones HOT0m1, HOT75m1, HOT75m3, HOT75m4, HOT75m8, MB0m1, MB0m2, MB20m2, MB20m5, MB20m12, MB40m1, MB40m5, MB40m12, MB100m5, MB100m7, MB100m9, MB100m10, PALB1, PALB2, PALB5, PALB7, PALB6, PALB8, PALE1, PALE6 and PALE7. The proteorhodopsin gene sequences retrieved from clones HOT0m1, HOT75m1, HOT75m3, HOT75m4, HOT75m8, MB0m1, MB0m2, MB20m2, MB20m5, MB20m20m12, MB40m1, MB40m5, MB40m12, MB100m5, MB100m7, MB100m9, MB100m10, PALB1, PALB2, PALB5, PALB7, PALB6, PALB8, PALE1, PALE6 and PALE7, have respectively Sequence ID Nos: 14, 16, 18, 20, 22, 24, 26, 28, 30, 32, 34, 36, 38, 40, 42, 44, 46, 48, 50, 52, 54, 56, 58, 60, 62, and 64.

Accordingly, FIGS. 11–36 also show the deduced amino acid sequence of each genetic variant of proteorhodopsin. The deduced amino acid sequence encoded by the proteorhodopsin gene retrieved from clones HOT0m1, HOT75m1, HOT75m3, HOT75m4, HOT75m8, MB0m1, MB0m2, MB20m2, MB20m5, MB20m12, MB40m1, MB40m5, MB40m12, MB100m5, MB100m7, MB100m9, MB100m10, PALB1, PALB2, PALB5, PALB7, PALB6, PALB8, PALE 1, PALE6 and PALE7, have respectively Sequence ID Nos: 15, 17, 19, 21, 23, 25, 27, 29, 31, 33, 35, 37, 39, 41, 43, 45, 47, 49, 51, 53, 55, 57, 59, 61, 63, and 65.

Figure 37:
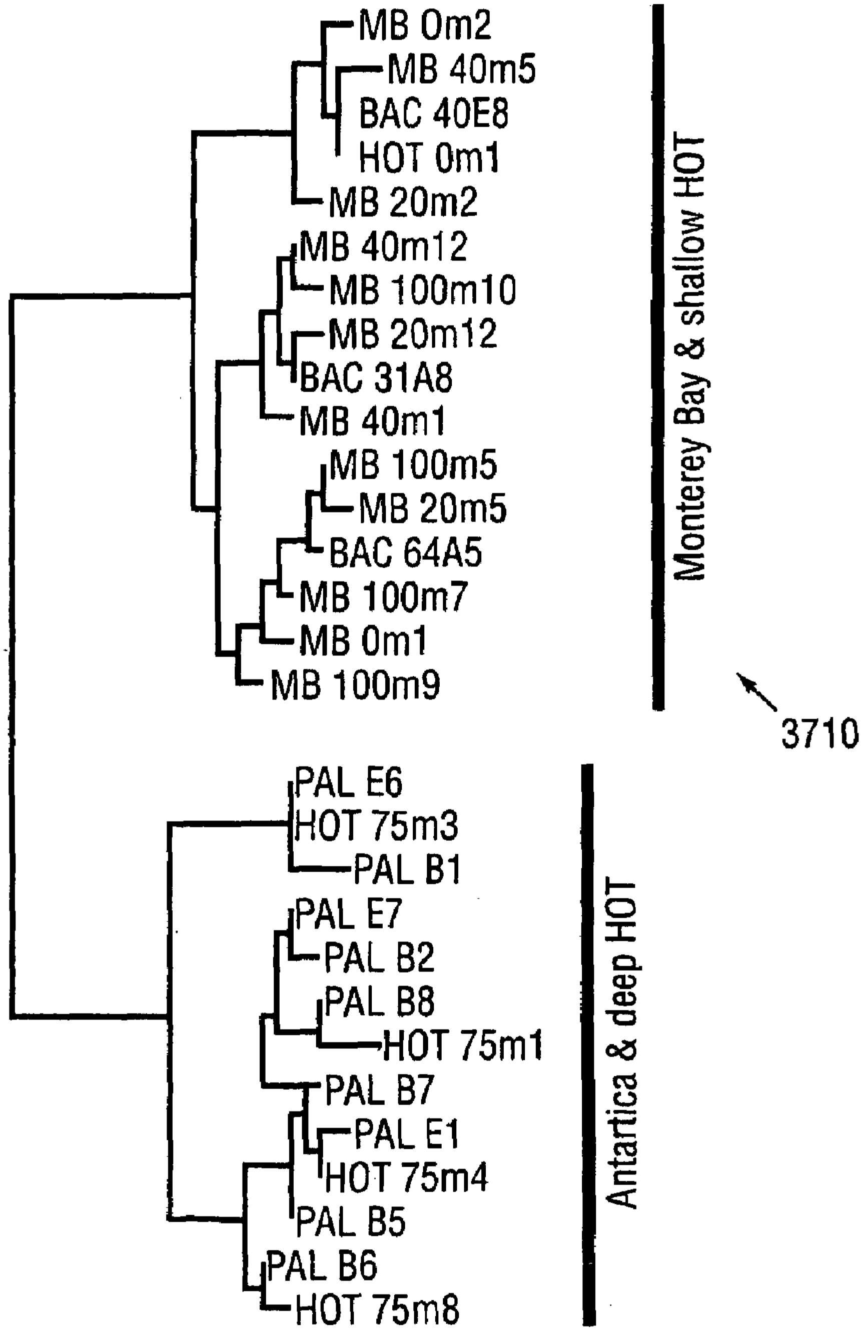
FIG. 37 illustrates a phylogenetic tree of different proteorhodopsin genes.
Figure 38A:
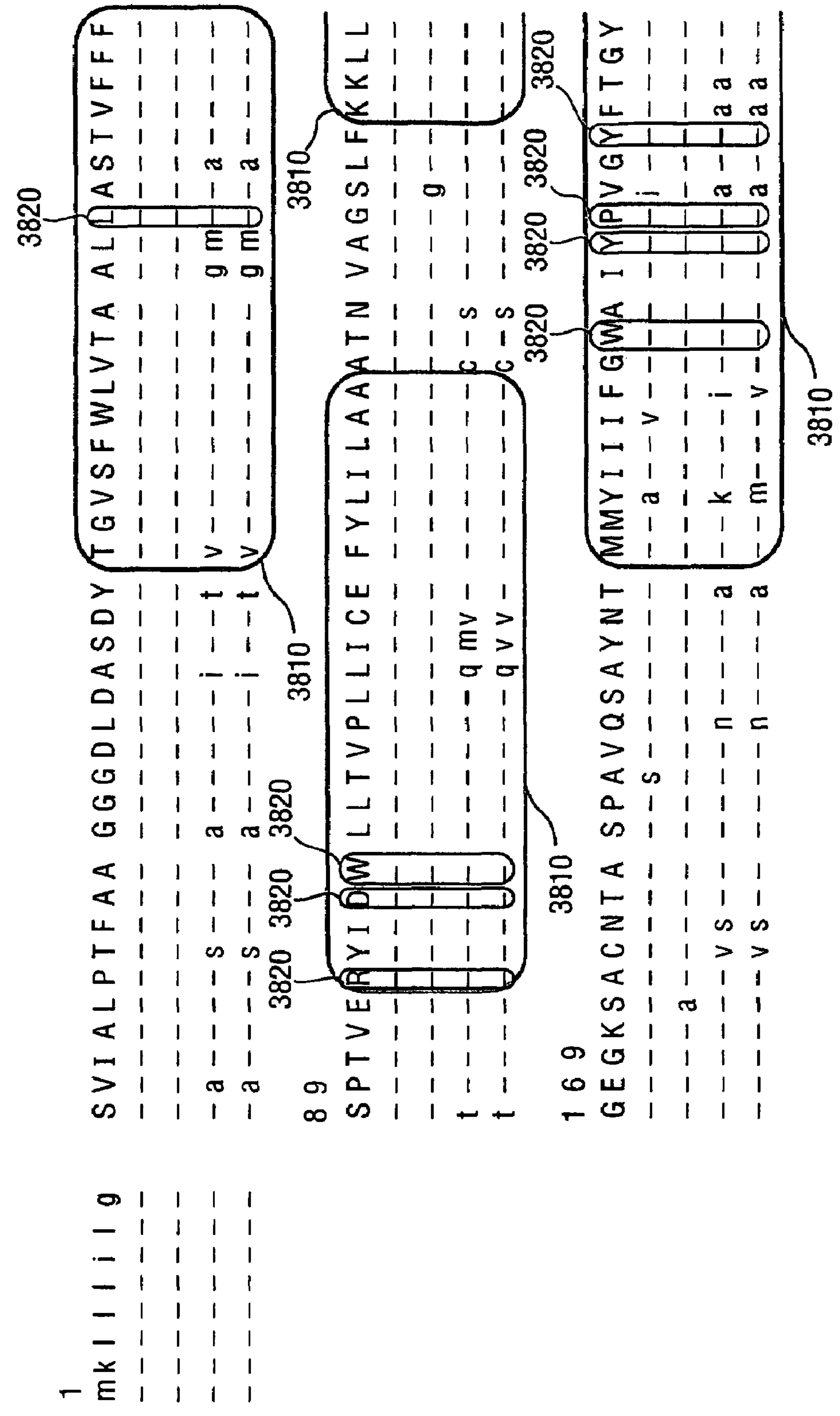
FIG. 38 provides an example of an alignment of proteorhodopsin amino acid sequences.
Figure 38B:
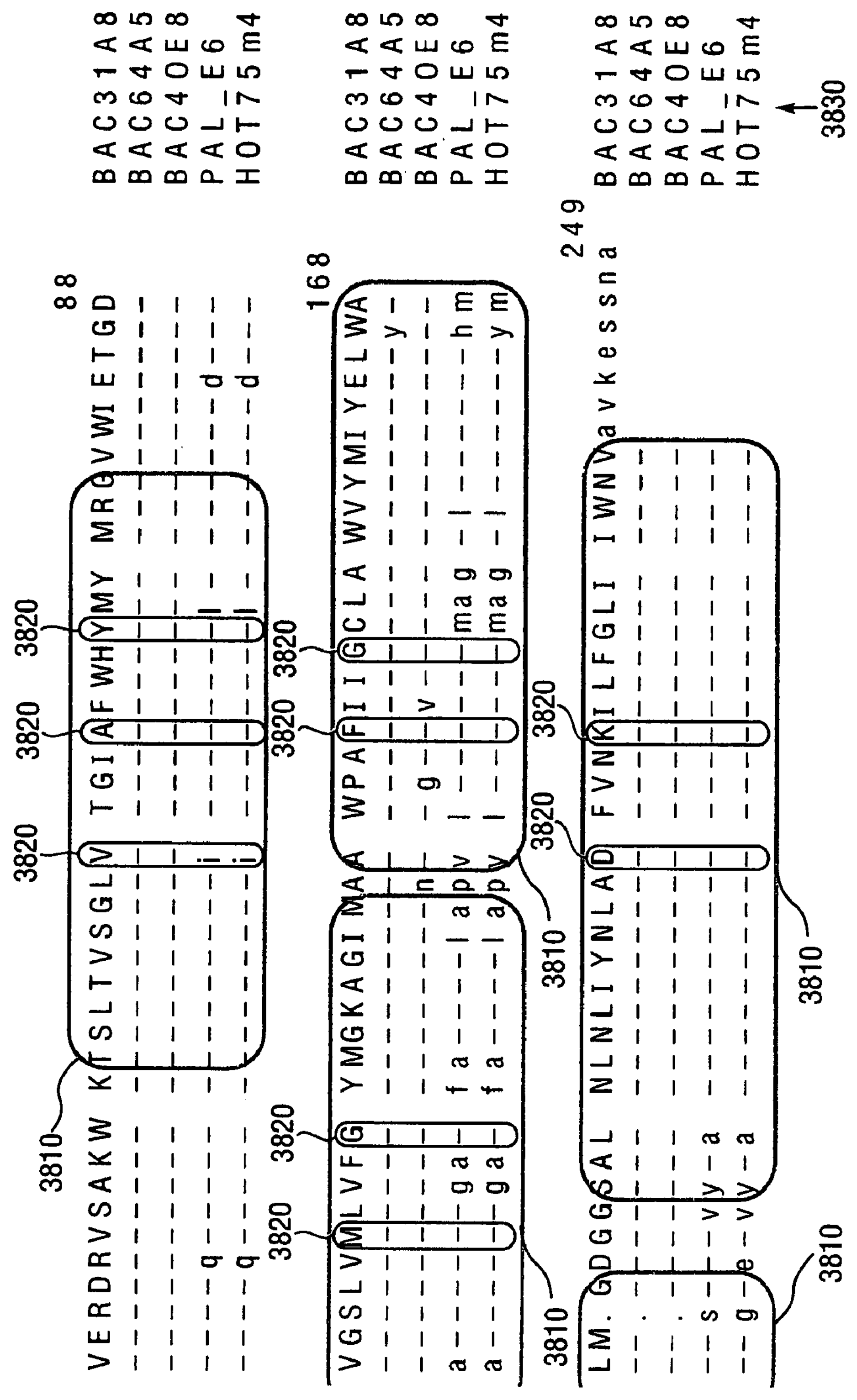

In an exemplary embodiment shown in FIG. 37, fifteen different variants of proteorhodopsin in the PCR generated MB gene library 3710 were detected, falling into three clusters. The MB gene library includes MB clones MB0m2, MB40m5, MB20m2, MB40m12, MB100m10, MB20m12, MB40m1, MB100m5, MB20m5, MB100m7, MB0m1, and MB100m9 as well as BAC clones BAC40E8, BAC31A8 and BAC64A5. FIG. 37 is based on a phylogenetic analysis of the inferred amino acids of cloned proteorhodopsin genes. Evolutionary distances calculated from 220 positions were used to infer the tree topology by the neighbor joining method using the PaupSearch program of the Wisconsin Package version 10.0 (Genetics Computer Group (GCG), Madison Wis.). Other methods could also be used. The variants of the MB library share at least 97% identity over 248 amino acids, as shown in FIG. 38, and 93% identity at the DNA level. All the PCR amplified proteorhodopsin genes from Antarctic marine bacterioplankton (e.g. the PAL clones) were different from those of Monterey Bay (e.g. the MB clones) sharing 78% identity over 248 amino acids with the Monterey clade. The changes in amino acid sequences were not restricted to the hydrophilic loops, but spread over the entire protein including changes near the retinal binding domain 3830 as shown in FIG. 38, which are predicted retinal-binding residues. FIG. 38 shows an example of a multiple alignment of proteorhodopsin amino acid sequences that were obtained from different clones 3820. The secondary structure is derived from hydropathy plots (boxes 3810 shows trans-membrane helices).

Light-Driven Energy Generator

Figure 39:
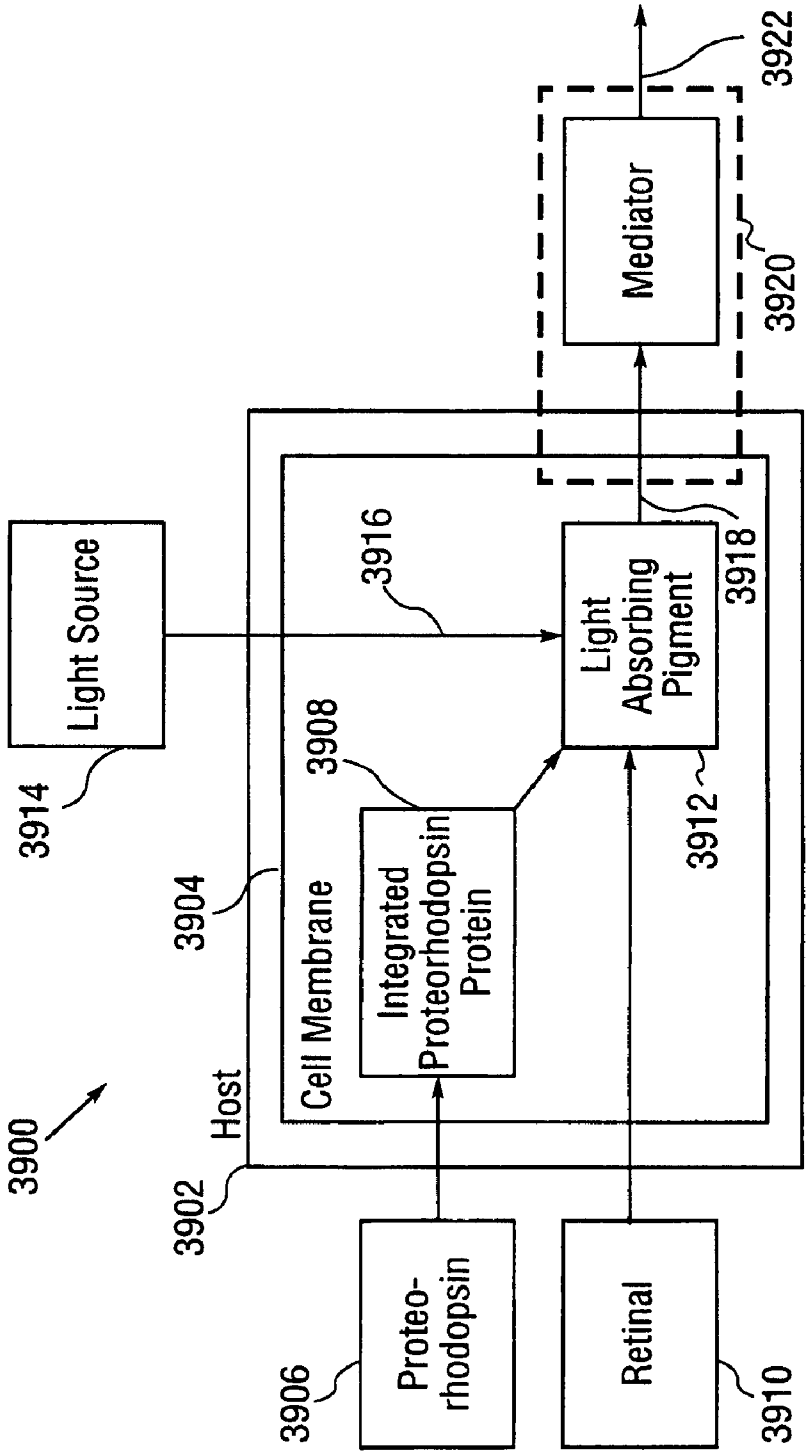
FIG. 39 provides a light-driven energy generator that utilizes proteorhodopsin.

FIG. 39 provides a light-driven energy generator 3900 that utilizes proteorhodopsin, as obtained from naturally occurring bacteria as described above, to convert light-energy into biochemical energy. Light-driven energy generator 3900 takes advantage of the functional properties of the proteorhodopsin protein once expressed in, for instance, *E. coli* and other bacteria. These properties include the ability of proteorhodopsin 3906 to integrate within the cell membrane 3904 of, for instance, *E. coli* making an integrated proteorhodopsin protein 3908 (also called an integrated cell membrane protein). These properties also include the ability of proteorhodopsin 3906 to bind retinal 3910, making a light absorbing pigment 3912. The source of retinal 3910 is not limited to chromophore retinal but could also include chemical derivatives of retinal, such as 3-methyl-5-(1-pyryl)-2E,4E-pentadienal, 3,7-dimethyl-9-(1-pyryl)-2E,4E,6E,8E-nonatetraenal, all-trans-9-(4-azido-2,3,5,6-tetrafluorophenyl)-3,7-dimethyl-2,4,6,8,-nonatetraenal and 2,3-dehydro-4-oxoretinal. Illuminating light absorbing pigment 3912 with a light source 3914 results in a chemiosmotic gradient or proton pump in which light energy 3916 is converted into biochemical energy 3918. The chemiosmotic gradient involves pumping of protons from the inside to the outside of cell membrane 3904. When the protons return to the inside of cell membrane 3904 it produces biochemical energy 3918 via a proton translocating ATP-ase. Finally, the biochemical energy 3918 is harnessed by a mediator 3920 to produce energy 3922 for a particular process. For example, since proteorhodopsin functions as a light driven proton pump, it generates energy in the form of a proton motive force across the host cell membrane upon illumination. This light-driven proton motive force can be converted to many other forms of energy, one example above being the regeneration of adenosine triphosphate (ATP), via a proton-translocating ATPase. This coupling of the proton motive force generated by proteorhodopsin, for use by proton-translocating ATPases to synthesize ATP, could be accomplished both in living cells, as well as in artificially constructed membrane systems such as liposomes. Proteorhodopsin-based systems can convert light energy to a wide variety of useful mechanical, chemical, and electrical energy forms, for many industrial and technological applications. These include, but are not limited to, use in targeted drug delivery, uses as primary or secondary energy generators for biocatalyic reactors, fuel cells and nanomachines (including molecular motors), as well as uses in molecular switching or data storage devices.

Applications that can potentially benefit from proteorhodopsin-light driven energy generation are, for instance, bio-electronics applications that are aimed to interface, integrate, or substitute the silicon based microelectronics systems as well as molecular devices. Other applications that can potentially benefit from proteorhodopsin-light driven energy generation are, for instance, in bio-materials, wherein proteorhodopsin is integrated as a bio-material in, for instance, optical films for light mediated computer memory applications, optical information storage and pattern recognition.

Alternatively, proteorhodopsin is useful for a process to enhance yield or increase the potential of recombinant protein production or converting the light induced membrane potential into cellular signals, including modulation of gene expression. The biochemical energy derived from functional proteorhodopsin exposed to light could be harnessed to support a variety of cellular processes. For instance, the energy derived from light-mediated proton pumping could be used to enhance the production of secondary metabolites, or recombinant proteins in host cells, such as *E. coli*. Often, production of specific compounds in the biotechnology industry is limited, since their optimal expression or production occurs in the late stationary phase of growth, when energy reserves of the host cells are low. Retinal-bound proteorhodopsin expressed in such cells would provide an ample source of biochemical energy, by simple illumination. Proteorhodopsin-mediated light driven proton production could enhance any variety of biosynthetic or physiological processes which require energy.

The biochemical energy derived from proteorhodopsin light driven proton pumping could also be converted to other generally useful energy forms, for example electricity. Microbial fuel cells currently use carbon-based compounds, such as glucose, as the primary energy source. Via specific mediators of reduction potential (e.g. electrons), these microbial fuel cells convert cellular biochemical energy to electrical potential. Unlike carbon-based microbial fuel cells, proteorhodopsin uses light as the energy source, that can then be converted into a chemiosmotic potential, and finally into cellular biochemical energy by membrane-bound proton ATP-ases. Therefore, the use of proteorhodopsin could be employed to derive energy from light as the primary or supplementary energy source, that could then be converted into electrical potential (analogous microbial fuel cells that derive their energy from glucose).

In addition to energy generation in vivo in living cells, membranes containing proteorhodopsin could be used to enhance or enable other specific processes in vitro. Polymers produced from proteorhodopsin-containing membranes may have specific properties that could be used similarly to those containing bacteriorhodopsin. One example includes the use of these light sensitive molecules for optical computing applications.

As shown in FIG. 39, the kinetics of proteorhodopsin as it is utilized in 3900 is influenced by various factors such as the type of light source 3914 and the manipulation of light source 3914 in terms of frequency and/or wavelength at which the light 3916 is delivered. Light source 3914 could be any type of light source that delivers light energy 3916 that would be absorbed by light absorbing pigment 3918. For example, the light source 3914 could be tuned to optimally excite rhodopsin variances with an absorbance maximum of 490 nm or alternatively those rhodopsins with an absorbance maximum of 520 nm. Manipulation of the light source 3914 or the light 3916 being emitted by the light source 3914, for example, involves changing the frequency of fast-light pulses or the delivery of light 3916 as individual pulses, a train of pulses, or a continuous source of light. Manipulation also involves changing the wavelength of the delivery of light 3916 at different wavelengths. In addition, as is clear for one skilled in the art, changing the frequency and/or amount of retinal that will bind within integrated cell membrane protein 3908 also varies the function of proteorhodopsin. Finally, as was mentioned in the previous section, genetic variants of proteorhodopsin result in variants of the proteorhodopsin proteins that changes the kinetics of 3600 due to a difference in absorption of light at different wavelengths. The functional expression of such variation in these proteorhodopsin proteins adds another source of variation to the kinetics of proteorhodopsin as it is utilized in 3900.

As shown in FIG. 39, the light-driven energy generator includes a host 3902. In the present invention, as a preferred embodiment, host 3902 is a cell membrane preparation of *E. coli*. However, the present invention is not limited to the use of *E. coli* and, alternatively, other bacteria or eukaryotes could be used to provide host 3902 as an intact cell (in vivo) and/or as a cell membrane preparation (in vitro). For example, but not limited to, bacteria and yeast with developed genetic systems such as *Bacillus* spp. Species, *Saccharomyces* spp., *Streptomyces* spp. or *Pichia* spp. could be used as host for the expression of proteorhodopsin. In addition, in case a cell membrane preparation (in vitro) is used, host 3902 becomes equivalent to cell membrane 3904.

The light-driven energy generator 3900, as shown in FIG. 39, further includes proteorhodopsin 3906. Proteorhodopsin is presented in the form of the earlier presented expression vector containing a proteorhodopsin gene or one of its variants. Once proteorhodopsin 3906 has been put into host 3902, the proteorhodopsin expression vector expresses the proteorhodopsin protein in host 3902. An integral cell membrane protein 3908 is created in which the proteorhodopsin protein inserts into and folds properly within the cell membrane 3904. This is accomplished in the *E. coli* host by virtue of the native signal sequence found in the 5' end of the proteorhodopsin gene. It could also be accomplished by replacement of native sequence with another host-specific signal sequence in non-*E. coli* host systems.

Figure 40:
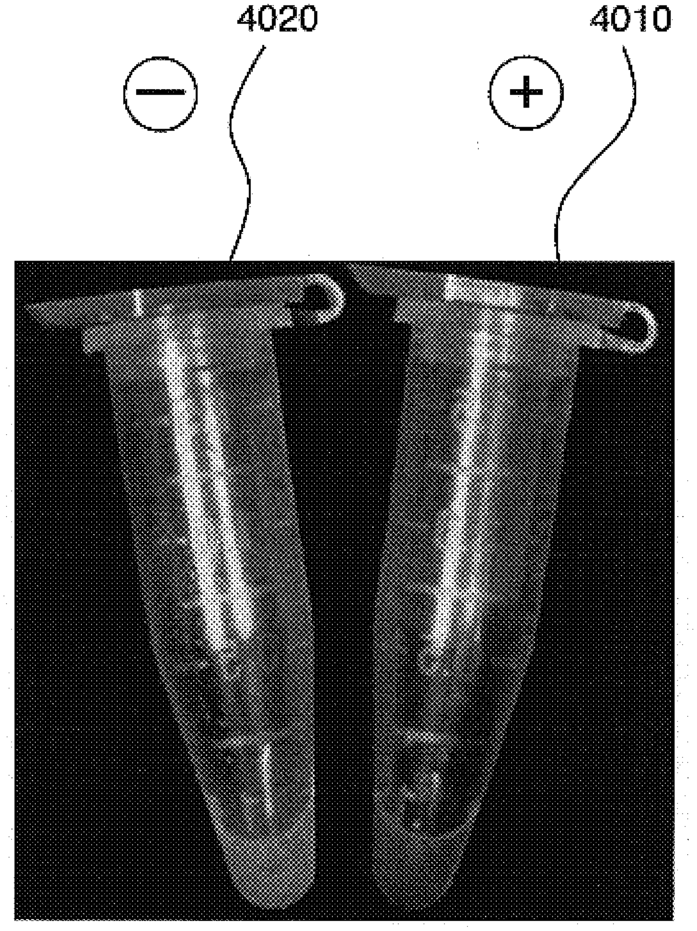
FIG. 40 provides an example of a proteorhodopsin-expressing *E. coli* cell suspension (+) compared to control cells (−), both with all-trans retinal.

As shown in FIG. 39, once retinal 3910 is added to cell membrane 3904, retinal 3910 binds within integrated cell membrane protein 3908 and forms a light absorbing pigment 3912. The particular example of FIG. 40 shows an integrated proteorhodopsin protein 3908 bound to retinal 3910 in *E. coli*. Chemical derivatives of retinal (as discussed above) could also be used as a substitute chromophore to generate functional proteorhodopsin. For the particular example of FIG. 40, the proteorhodopsin protein was cloned with its native signal sequence and included an addition of the V5 epitope, and a polyhistidine tail in the C-terminus. The proteorhodopsin protein was expressed in host 3902, i.e. *E. coli* outer-membrane protease-deficient strain UT5600, and induced with 0.2% arabinose for 3 hours. Cell membranes 3904 were prepared and resuspended in 50 mM Tris-Cl (pH 8.0) and 5 mM $MgCl_2$. FIG. 40 shows a proteorhodopsin-expressing *E.coli* cell suspension. After 3 hours of induction in the presence of 10 μM all-trans retinal, cells expressing the protein acquire a reddish pigmentation as indicated by 4010 and the + (plus) symbol. FIG. 40 also shows that a cell suspension using the same PCR primers (Sequence ID No:2 and 3) but now in opposite orientation as a negative control, did not acquire a reddish pigmentation as indicated by 4020 and the – (minus) symbol.

Figure 41:
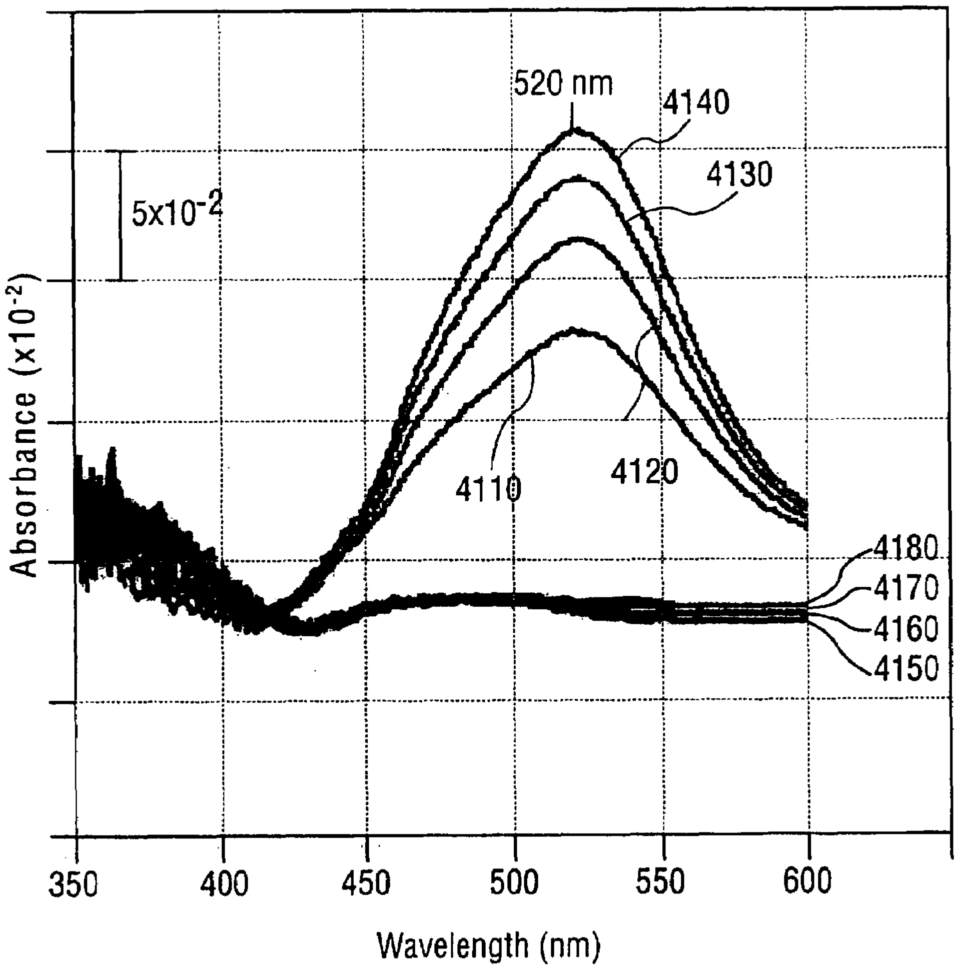
FIG. 41 provides an example of absorption spectra of retinal-constituted proteorhodopsin in *E coli* membranes and a negative control.

FIG. 41 shows an exemplary embodiment of the absorption spectra of light absorbing pigment 3912 upon illumination with light source 3914 as is shown in FIG. 39. As mentioned above, the light absorbing pigment is a retinal-reconstituted proteorhodopsin in *E. coli*. FIG. 41 shows absorption spectra of light absorbing pigment 3912 as well as a negative control. After retinal 3910 addition to integrated proteorhodopsin protein 3908, light absorbing pigment 3912 was made. The retinal 3910 addition was done at selected time points, i.e. 10, 20, 30 and 40 min, and shows a progression from low to high absorption values indicated by respectively 4110, 4120, 4130 and 4140 upon illumination with light source 3914. FIG. 41 also shows the absorption spectra of retinal 3910 addition at these similar time points but now to a negative control of retinal 3910 containing a proteorhodopsin 3906 that was created using the same PCR primers in opposite orientation. 4150, 4160, 4170 and 4180 indicate the four absorption spectra for the negative control. An absorption peak at 520 nm was observed after 10 minutes (4110) of incubation as illustrated in FIG. 41. On further addition of retinal, the peak at 520 nm increased, and had a ~100 nm half bandwidth. The 520 nm absorption peak was generated only in membranes containing proteorhodopsin 3906, and only in the presence of retinal 3910. The red shifted λmax of retinal (λmax=370 nm in the free state) is indicative of a protonated Shiff base covalent linkage of retinal to proteorhodopsin.

Figure 42:
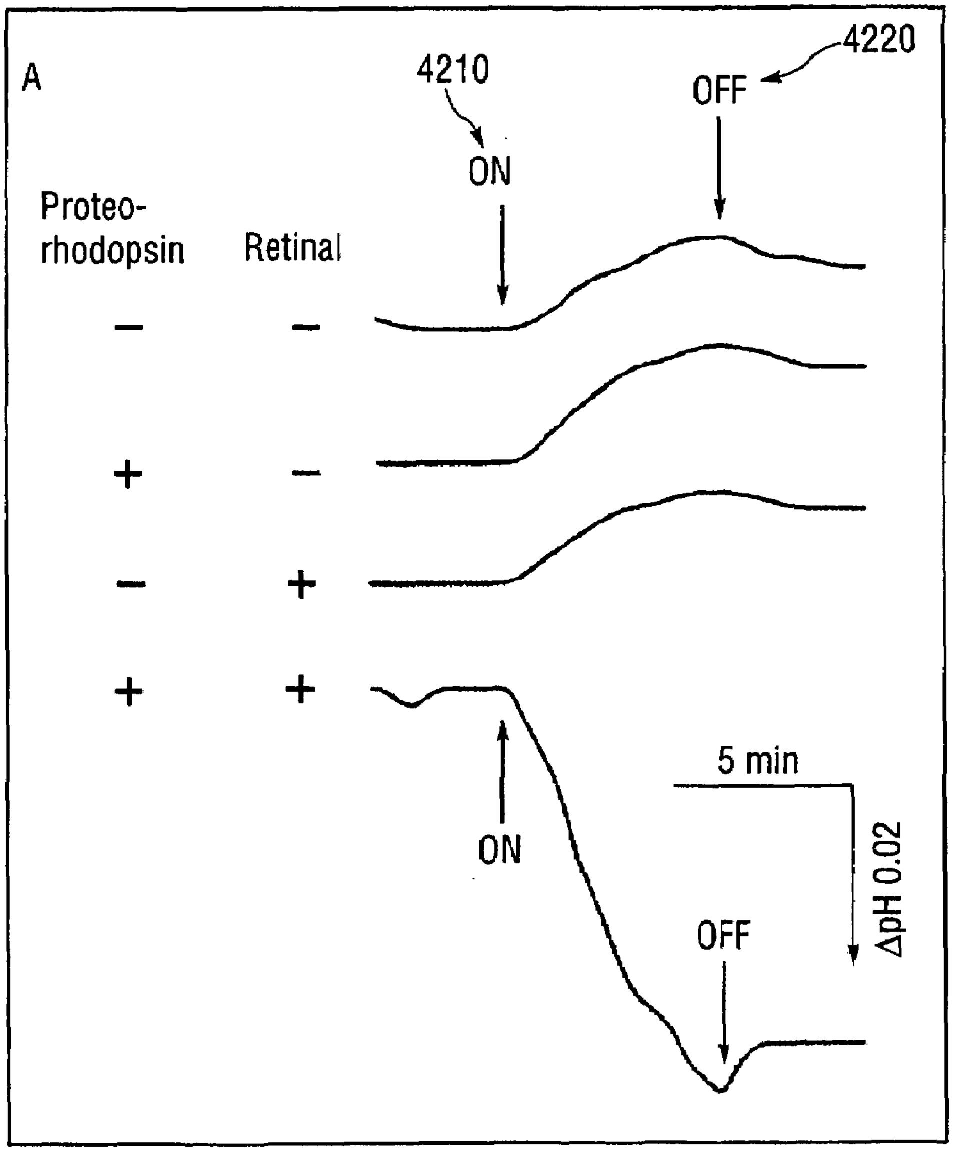
FIG. 42 provides an example of a light-driven transport of protons by a proteorhodopsin-expressing *E. coli* cell suspension.

FIG. 42 shows an exemplary embodiment of the light mediated proton pump of the light-driven energy generator 3900 indicating the conversion of light energy 3916 as shown in FIG. 39. The proton pump action is illustrated by measuring pH changes in the medium surrounding the host 3902, which in this particular example involves a cell suspension of *E. coli*, illuminated by light source 3914. The beginning and cessation of illumination (with yellow light>485 nm delivered by 3916) is indicated 4110 ("ON") and 4120 ("OFF") respectively. The cells were suspended in 10 mM NaCl, 10 mM $MgSO_4.7H_2O$ and 100 μM $CaCl_2$. Net outward transport of protons was observed solely in proteorhodopsin-containing *E. coli* cells, and only in the presence of retinal 3910 and light 3916 and is indicated by 4210 in FIG. 42. Light-induced acidification of the medium was completely abolished by the presence of 10 μM of the protonophore CCCP.

Figure 43:
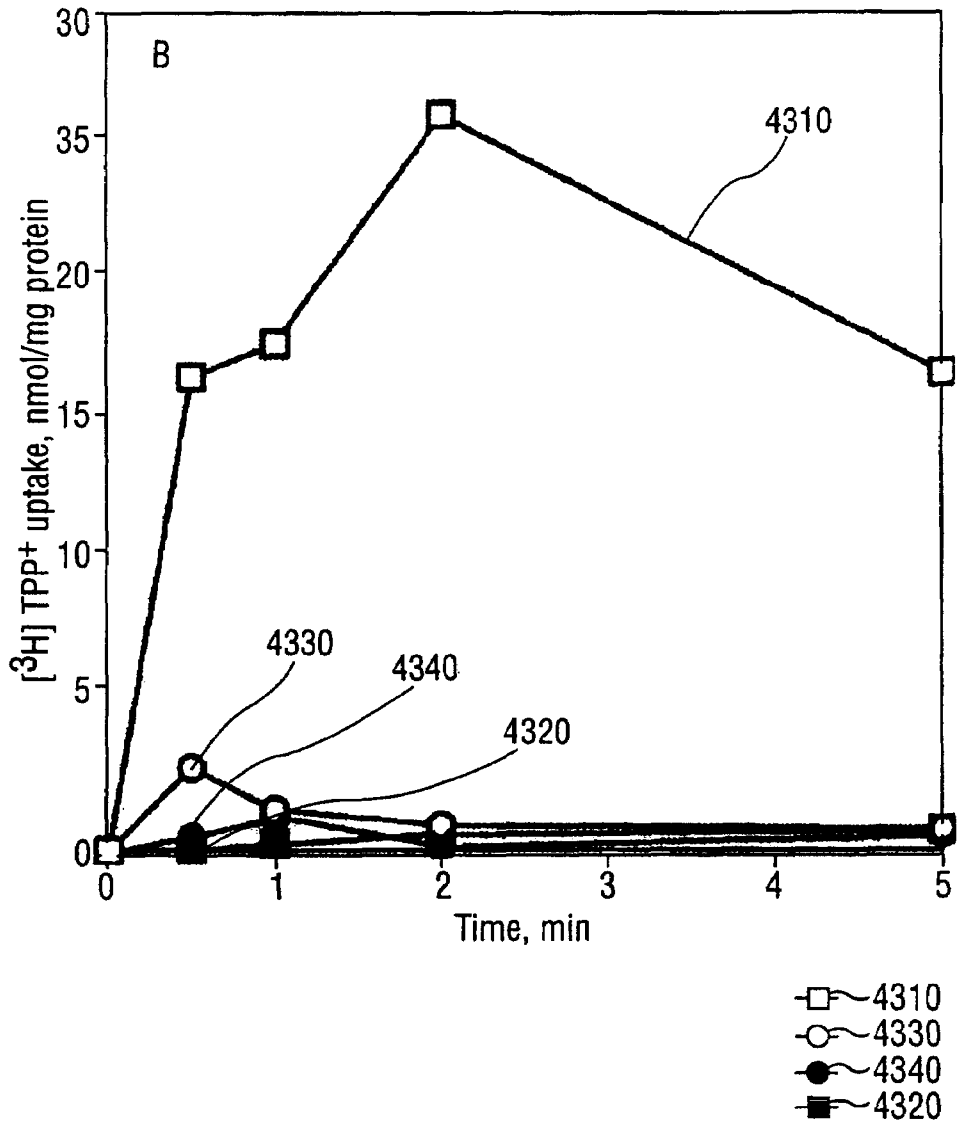
FIG. 43 provides an example of a transport of $[^3H]TPP^+$ in *E. coli* right-side-out vesicles containing expressed proteorhodopsin, reconstituted with or without 10 μM retinal in the presence of light or in the dark.

FIG. 43 is an exemplary embodiment showing that illumination by light source 3914 generates an electrical potential at the membrane 3904 in proteorhodopsin-containing right-side-out membrane vesicles, in the presence of retinal 3910, reaching −90 mV after 2 minutes from light 3916 onset. Transport of $[^3H]TPP^+$ in *E. coli* right-side-out vesicles containing expressed proteorhodopsin, reconstituted with (4310 and 4320) or without (4330 and 4340) 10 μM retinal 3910 in the presence of light (4310 and 4330) delivered by the light source 3914 or in the dark (4320 and 4340). FIG. 43 shows that proteorhodopsin, in its form of 3912 as a light absorbing pigment, pumps protons from the inside to the outside of cell membrane in a physiologically relevant range. The ability of proteorhodopsin to generate a physiologically significant membrane potential, even when heterologously expressed in nonnative membranes, is consistent with the proton pumping function for proteorhodopsin in the native gamma proteobacteria from which it is derived.

FIG. 44 is an exemplary embodiment showing that proteorhodopsin can have a fast photocycle and can therefore be characterized as a fast and therefore efficient transporter of protons. For the particular example of FIG. 44, light absorbing pigment 3912 is induced by laser pulses delivered by light source 3914. Laser pulse-induced absorption changes are shown by 3912 in host 3902, which in this case are suspensions of *E. coli* membranes containing proteorhodopsin. A 532-nm pulse (6 ns duration, 40 mJ) was delivered at time 0 and absorption changes were monitored at various wavelengths in the visible range in a lab-constructed pulse photolysis system. 64 transients were collected for each wavelength. 4410 indicates transients at 3 wavelengths exhibiting maximal amplitudes. 4420 indicates absorption difference absorption spectra calculated from amplitudes at 0.5 ms (indicated by 4430) and between 0.5 ms and 5.0 ms (indicated by 4440). In 4410, transient depletion occurred near the absorption maximum of pigment 3912 (500-nm trace indicated by 4450), and transient absorption increase was detected at 400 nm (indicated by 4460) and 590 nm (indicated by 4470), indicating a functional photocyclic reaction pathway. In 4420, the absorption difference spectrum shows that within 0.5 ms an intermediate with maximal absorption near 400 nm is produced (indicated by 4430), typical of unprotonated Schiff base forms (M intermediates) of retinylidene pigments. The 5-ms minus 0.5-ms difference spectrum 4440 shows that following M decay an intermediate species red-shifted from the unphotolyzed 520-nm state appears. The decay of proteorhodopsin final intermediate is the rate limiting step in the photocycle and is fit well by a single exponential process of 15 ms, with an upward baseline shift of 13% of the initial amplitude.

Figure 45:
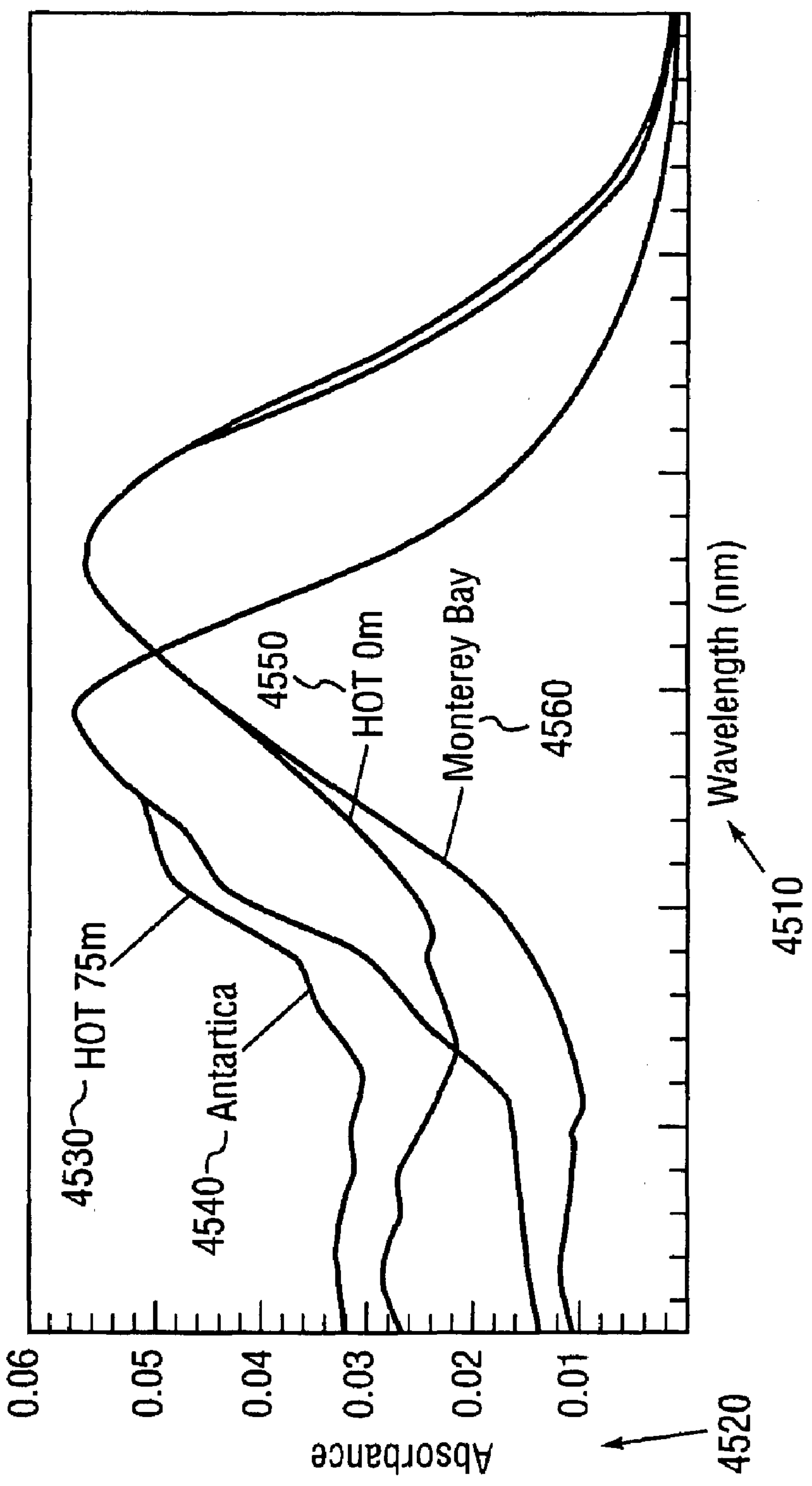
FIG. 45 provides an example of absorption spectra of retinal-constituted proteorhodopsin in *E. coli* membranes.

As mentioned above, a proteorhodopsin gene or protein variant can be selected to determine an absorption spectra of the light absorbing pigment to change the kinetics of the light energy generator 3900, for instance to meet a design/functional criteria of an application wherein proteorhodopsin is utilized. FIG. 45 shows an exemplary embodiment of different absorption spectra of retinal-reconstituted proteorhodopsins in *E. coli* as a function of wavelength 4510. As shown in FIG. 45, the absorbance 4520 is different and depends on the clone from which the proteorhodopsin was amplified. In this particular example, 5 μm all-trans retinal was added to the membranes suspensions in a 100 mM phosphate buffer, with a pH 7.0, and absorption spectra were recorded. The four spectra 4530, 4540, 4550, and 4560 are respectively for the proteorhodopsin genes retrieved from clones HOT75m4, PALE6, HOT0m1, and BAC31A8 at 1 hour after retinal addition. The proteorhodopsin gene retrieved from clone HOT75m4 4530 and PALE6 4540 produced a blue (490 nm) absorption maximum. The proteorhodopsin gene retrieved from clone HOT0m1 4550 and BAC31A8 4560 produced a green (527 nm) absorption maximum. In general, a range of wavelengths could be obtained that is not limited to the range shown in the example of FIG. 45.

It will be clear to one skilled in the art that the above embodiment may be altered in many ways without departing from the scope of the invention, such as for instance by mutagenesis to change the genetic sequence of proteorhodopsin and thereby changing the kinetics of the proteorhodopsin protein once it is expressed. Accordingly, the following claims and their legal equivalents should determine the scope of the invention.

What is claimed is:

1. An isolated DNA molecule encoding a proteorhodopsin protein, wherein said proteorhodopsin protein has the amino acid sequence shown in Sequence ID NO:5 or Sequence ID NO:7.

2. The isolated DNA molecule of claim 1, wherein said DNA molecule comprises the nucleotide sequence shown in Sequence ID NO:4 or Sequence ID No:6.

3. An expression vector comprising the isolated DNA molecule of claim 1.

4. A host comprising the expression vector of claim 3, wherein said proteorhodopsin protein is expressed in said host.

5. An artificial membrane system comprising the proteorhodopsin protein of claim 1.

6. The host of claim 4, wherein said host is a bacterium.

7. The host of claim 6, wherein said bacterium is *E. Coli.*

8. A cell membrane preparation of the bacterium of claim 6 comprising the proteorhodopsin protein of claim 1.

9. The host of claim 4, wherein said host is a eukaryote.

10. A cell membrane preparation of the eukaryote of claim 9 comprising the proteorhodopsin protein of claim 1.

* * * * *

SEQUENCE LISTING

<160> NUMBER OF SEQ ID NOS: 65

<210> SEQ ID NO 1
<211> LENGTH: 105184
<212> TYPE: DNA
<213> ORGANISM: Naturally occurring gamma proteobacterium
<220> FEATURE:
<221> NAME/KEY: gene
<222> LOCATION: (50866)..(51615)
<223> OTHER INFORMATION: Proteorhodopsin gene sequence.
<221> NAME/KEY: misc_feature
<222> LOCATION: (1593)..(2807)
<223> OTHER INFORMATION: Predicted threonine dehydratase.  Contains 'n' at position 2753.
<300> PUBLICATION INFORMATION:
<301> AUTHORS: Beja,O., Aravind,L., Koonin,E.V., Suzuki,M.T., Hadd,A.,Nguyen,L.P., Jovanovich,S.B., Gates,C.M., Feldman,R.A., DeLong,E.F
<302> TITLE: Bacterial rhodopsin: evidence for a new type of phototrophy in the sea
<303> JOURNAL: Science
<304> VOLUME: 289
<305> ISSUE: 5486
<306> PAGES: 1902-1906

-continued

<307> DATE: 2000-09-15
<308> DATABASE ACCESSION NUMBER: AF279106
<309> DATABASE ENTRY DATE: 2000-06-15
<313> RELEVANT RESIDUES: (50866)..(51615)

<400> SEQUENCE: 1

```
ttgttatatc agtaatggct attgctccaa taacttaata ctaatatata attagtttat     60

gaataaattt tatatatttg ggttattgtt ttttacacta aatgcatttt cttgctcaga    120

tcttctagat acagacatga gagttcttga ttccgctgag tcaagaaacc tttgcgagtt    180

tgaaggaaaa gctttactag ttgtgaatgt tgcaagtaga tgtggttaca cttatcaata    240

tgctggcctt caaaagttat atgaaagtta taaagatgaa gattttctag taattgggat    300

cccatctaga gatttttcttc aagaatactc tgatgaaagc gatgttgcag aattttgttc    360

tacagaatac ggtgttgaat ttcctatgtt ctcaactgct aaagtcaaag gaaaaaaagc    420

acacccattt tataaaaaac ttattgcaga atcaggtttt actccctcat ggaactttaa    480

taaatactta atctcaaaag agggcaaggt tgtatccaca tatggatcaa aggtaaagcc    540

tgattcaaaa gagcttatat cagctataga aggcttgctg taaaattatt acttagaaac    600

taatacagtt ttaggcttgt ttgctgcaaa tattccatta tctacaactc caggaatatt    660

attaatcaaa gcttccattt cagtggggtt tgaaatatcc atattagaga tatctaaaat    720

gtgattacct tggtctgtta taaatccagt tctatatgtg ggtattccac cgatcgagat    780

tatttttctt gcaacaaggc tcctactttc aggtatcacc tctataggca gtggaaaagc    840

tcccaaaaga ttaaccatct ttgactgatc aactatacat ataaactcgt tagaggcaga    900

agcaactatc ttttctctag tatgtgcgcc accaccacct ttaataagac aattttcagg    960

agacacctca tctgcaccat ctatgtaata agctatatca actacatcat taaggctaaa   1020

gacctctatc ccattttcat ttaataattt tgatgaagca tctgaactag aaacagctcc   1080

agcaaatttg tgcctatgct cctttagttc ttctataaaa aaattaactg ttgagccggt   1140

tccaatacct aaaatcatct caggatgaag attatttttg atatattcta tagcttgttt   1200

agcaacattt atctttgagc cactcataga gttataatac aagaaaatat aggtagttaa   1260

ttattttgag actaaaaatt aaaaaaacag gttcttttaa gaattcccag aagtacctaa   1320

agcttattcc taatgcatct gtttatgacg tagcattaaa atcacctata acatttgctc   1380

taaatatttc ttcaaagctg gggaataaag ttttcctaaa aagagaggat ctgcaaccta   1440

tattttcttt taaaaacaga ggagcgtata acaagattgt aaatttatcc gatgccgaaa   1500

agaagagggg ggttattgct gcatcagcag gaaatcatgc tcaaggggta gccagtgcat   1560

gtaagaaatt aaaaattaat tgcttgatag ttatgccaat aacaactcca gaaataaaaa   1620

taaaagatgt aaaaagattt ggagccaaaa tactccaaca tggggacaac gtagatgcag   1680

cattaaaaga ggcactgttt attgcaaaga aaaaaaaatt gtcttttgtt catccttttg   1740

acgaccctct aacaattgct ggccaaggga ctataggaca agaaattctt gaagataaaa   1800

ataattttga tgttgtcttt gttccggtgg gaggaggagg tattctagct ggtgtatctg   1860

cctggatagc acagaataat aagaaaataa aaattgttgg tgttgaggtt gaggattccg   1920

cttgtcttgc tgaggccgta aaagctaata aaagagttat tttaaaagaa gtgggcctct   1980

ttgctgatgg ggtggcagta tcaagggttg gaaaaaataa ttttgatgtt attaaagagt   2040

gcgtagatga agtcattaca gttagcgttg atgaggtctg caccgctgta aaagatatct   2100

ttgaagatac aagggttcta tcagaacctg ctggggcatt agcacttgca gggttaaaag   2160
```

-continued

```
cctacgcaag gaaagttaaa aataaaaaac ttattgctat aagttctggc gctaatgtaa   2220
atttccaaag acttaatttt attgttgagc gatcagagat tggtgaaaat agagaaaaaa   2280
tattaagtat caaaatccca gagatacctg gaagttttct taagctttca aggatgtttg   2340
gcagctctca agttacagag tttaactaca ggaaatctag cttaagcgat gcatatgttt   2400
tagttggtgt tagaactaaa actgaaaaat catttgaaat cttaaagtcc aaattaaaaa   2460
aagcaggctt cacctttagc gactttactc gaaatgaaat atccaatgat catctgaggc   2520
atatggttgg tggcagaaat agtgactcag gctctcataa caatgaaaga atatttaggg   2580
gagagtttcc tgagaagccg ggcgcgctgt taaattttct agagaaattt ggaaataaat   2640
ggmatatttc cttatttcat tacaggaacc taggttcagc ttttggaaag atattaattg   2700
gcatcgagag taaggataaa gacaagctaa taaatcattt aaataagtca ggnactattt   2760
ttacagaaga aacctctaac aaggcataca aagatttttt aaaatgaaag gttaatactt   2820
taatctaaat ttaattgaaa aaagctcatc gctagggttt tcccacggct ctttgaacaa   2880
ctcggattga gatctatcat cctcctcgtc gtaaattctc ccacctttag aatagaccaa   2940
aaatagatat gacaaaggag cgagctcata tttatatcta atttggaacg aagctacgcc   3000
agtattaaat tcattaacta tattatttcc tttataaagg tatccattag catctgaaaa   3060
aatactaata ggattttttg ctttcaaagc aacaaattga ctcttaagtc tgatctcatg   3120
tttattattt ttaaaccaat ttagatcaaa agataaggta tcttgtcttg aatcatatga   3180
ggcaagatta ttattatcct gccatatcag ccattcattt tcctttctta ttctatattg   3240
cgcattgatt cttaagttat catttggaaa tattgaacct gctatcttgt aaaatttttct   3300
accataccca ttcgaatccc accgattatc tttctctccc ttaaagaagc taactctcca   3360
gtcatatgtc cagaatgaat agttctttgc ctcaaagtct gctgtaatac ctattcttct   3420
ttttgatttg ataaaggggt aggcttcatt ttttcttgtg atagttgtat ttttcccaga   3480
agatctaaag ttaaaatcta attgaaattt agagttgtcc ttaaaactaa aagaattttt   3540
ttgatcgatg cctattggat ttgaattacc agctgtgtca gcatcataat ttagatcaat   3600
tccataatct atttgtttta atatcgagct attatcaaat tcatttattt ttcgatttcc   3660
tccaatacca gcatgaatcc agtctcttct ttgcagataa ccaaagtcat ttaactcgaa   3720
gtcgtcttca aaataaagaa ggcttccact tatgttagat agtttatttg gaagatatgt   3780
aaactgagtc ctatacccaa gcccattttt accatctttt tctgaggcta acagatctga   3840
atatgtaatt aattttttttg aacgaatatt gatgtaatca ataacattga ctgttgatga   3900
ttcgcctgtc atttcattct caacattcgt taccatgaag ccaagcgttt tatttccaag   3960
ctttgttcga gatcgaagag cataatagtc tcttccaact gaaaaggctt catcagcctc   4020
acttgctaca aatactccaa attcattatt attacttttt tgagtaagtc ttaatgcaaa   4080
atcaatatca gaatagtttt ttttagctgc ctcgcaacct tcttcattac tttcttctga   4140
gcaattatag ctgggggcag ctccaatcct ccgcgtattt ataaccgagt atctatcata   4200
attactaata tcaaatagtg attggttttc attgaaaaat gctctttttt ctgagtaaaa   4260
agtttcttga gcagaaaagt taataaccac atcatcactc tcagcttgtc cgaaatctgg   4320
attaatagct aaatttattt gacgaccttt tccagtgcta taaaagattt cagccccaat   4380
atctgaccct tcttggtttg taactgaatt tttatttgaa gatatatatg gaaaaaaagt   4440
aagctttgat tttgtatagt tttgtatttc taagctatct aactcttgaa agtagtcatt   4500
tctactagcc attgttccgg cactgctaac ccatgactca ttttcggcac tataacgtaa   4560
```

-continued

```
tgcggtgtaa ttaatttttc ttatatcacc atcaggctgt ttcattaacg ttacatccca   4620
aggaataaaa aactcagaga cccaataccc atcaaatttt tgtgtttttg caatccaatc   4680
tccatcccag tctgtcttaa agtctcctgc ttgcgttttt atggcatcga aaagcgagtt   4740
cccaagattt atagcaagaa tgaaagcttt gttaccatca ccatcaaagt ctatatttat   4800
agagttttta tcgctaagtg aatttatttg atctctaagc gtcttcctgg agaacataga   4860
atcattactt tgaaaattct taaatccaac atatatacca tccttatttg agaaaattaa   4920
agccgttgta agaagttcat ttttcttaag agtaaaagga gatgtttcat aaaaatctgt   4980
aatttcaaat gcattattcc actcaggctc atcaagagag ccatcaataa caattgagtt   5040
tgaccaaatc agcacagagg taagtaaaag tgataatgag gctaaagtta ttttcataga   5100
tagatttaat tcagagtatt ttaatctatg aagagtagga aatcatccga tcattctcag   5160
aaaaaacata atcatattta aggtcatgtt tttctccaaa atgcatatta caaatctggt   5220
attgataaca cagtccaacc aataaaggtc ttgatacctc ctcgtttata gagccaataa   5280
ttctatcgaa atatccagag ccatagccaa gcctgtatcc atttaaatca actcctgtca   5340
taggaataaa cattaaatca atttcattta tgttgacata atcttcactt ttaacctctt   5400
tgatcccaaa ttgatttata aagaagttag gctgctcatc cagcaaatta aaagccatca   5460
tttcgtcatc aattactttt ggaatataaa tattcttttt aagtttagta aaagcttgaa   5520
ttaacaaatt tgtattgact tcatttcgaa aaggaaaata taaggcaatg ttttgcattt   5580
catgagtatt gatttttttct aatacatttt cttggattaa aaaacttata ttgctcttag   5640
ataaatcaga aatagactgc ccctgctcaa agagtgattt tcgtatttta tttttcacca   5700
taaattgtgc cgaggctaac aaaccaaatc accgccatgt gctatacctg aaccgatggg   5760
tcaggtggtg aatttcataa caaatcaggc ttccctgtaa aggtactgcg caacaatgct   5820
agaggaatat cacctattta attgtatcgg ttcaaattta ttaacacatt agcgtatgaa   5880
ccagaatgca gttaattata aaatatatag gtattaagta aaagttaatt tttagagagc   5940
agactctatt ttttgtatta gcttttcgat atctttatta tttaaagcag agtcagtatt   6000
ctcggttggc ttggataaaa gcttactagc catagttaga ccagctatca ccaaggcatt   6060
attcttatca ctgatgccat caagctcatc atttaataat tttgcagctc taatgagttg   6120
gtctttctct tctggcggac aggctaacgt cagatctcgg ccaaaaattc ttaaagatag   6180
cgtttccatt tctgacatta ttttttgagt ttagttattt ctttatttag tatgagctta   6240
tctttttttcc agtctctttc cctttgcaca taagaatcta ttattccttt ttgctcatca   6300
aatcttttta tcaaaagatc taccttatcc tctagttcaa ataatgatga ttttttttct   6360
tctgacattg tataagttta attgtactag aatgaattgg aaagtttctt taataaaaga   6420
gtaaaataag gcatggaaaa aataattttt aaaaacagaa gagattcact tataaaacac   6480
ctacctaaga attcagcctt aattgtacct ggtgcagatt tgcaatatag aaatgctgac   6540
tcatcttata atttaagaca ggaaagtagc ttctactatc tgtctggctt ttgtgagccc   6600
tcttctctaa tggttttagt taataatgga aaaagcattg attcaataat ttttgttcct   6660
gaaaaagata aacttaaaga aatctgggat ggttatcgag ctggccctga gggcgcaata   6720
aatgattttc tttttgatca agcttttgaa aataataaat cagatgcttt aatgcctgaa   6780
atccttcaag ggctagaaaa agttttttat tcaataggga agaaaaatgg ctttgatcag   6840
aaagtaattg actggacatg cgcagcaaat tctaaagata ggcacagcaa atcaattgat   6900
```

-continued

```
attattgatg gctcttcgat ggtaggaaat ttaaggctta tcaaagataa gcatgaaatt   6960
gatattatga agagagcttg tgaaatttca gctgaatcat atattgaggt catgaaatct   7020
ataaagcctg ggacaatga gcaggaaata gaggcgctat ttttatatga attcgccaaa   7080
aggggaggaa ggtttccagc ttatacacct atagttgctg gaggtgaggg tgcttgtgta   7140
ttgcattata ttgaaaatga taaagagtta gcttcatcag atttaatttt ggtagacgca   7200
ggatgtgaat acaaaatgta tgcatctgat atcacaagaa ccttcccagt aagtggaaaa   7260
ttttcagatg aacagctaca aatttataat attgtccaca aagccaatct tgctgcaatc   7320
gatgctgtaa aaactggtaa tagcataatg gagccccaaa tggtttcaga aaaagtaatt   7380
actgaaggtc ttgtagagtt gggtattcta tctggcgatg ttaatcagct tcataaaaat   7440
ggtgcattca aggactttta tatgcataag gtgggacatt ggcttggact tgatgttcat   7500
gatgttggtg actacatgga gggagatgag tttatgaagt ttaagccagg gatgataacc   7560
acaatcgagc caggcatcta tatcagtagc gcaatggatg tagatgacaa atggaaaggc   7620
atcggcataa gaatagagga cgacatcctt gtaacagatt caggcaatat taatctaaca   7680
gagaaggtgc catctaatcc tcaagaaata gaatcattga tggcttagac tatggaggtt   7740
ccaattgtta tttctggcgg agggataata ggtaattaca tttctcttag gcttgaaaaa   7800
aataatatca aaaccgttat tgtcgaaaaa gctagtagtt tcaaagccct agataagggt   7860
ataagaacag tcactctcaa tgagcattct atgcaaatgc taaaaaatat tggtatttgc   7920
ccatcaattg ctcaaatcaa cagcatcgac gtattagatg gtgagggtac aggcaaaatt   7980
caatttctag caaaggacgt aggcagcgaa aacctttcat atgtaaccta tttcaatgaa   8040
ttacaaaaac taatttctga tccatgtaaa gaaagaacct tatttaataa tgagattgat   8100
tcagttcaga atcttaatac agaatctgat ccagagatca tgcttaaaga tggcatgacc   8160
ataaaaacga atctaattgc tggatgtgat ggaagaaatt caaatattgc aaaaattgct   8220
tcacttacaa gcagcttcga tgactactta caaacagctt taacttttgt cgttgatatt   8280
gataatgatt cacatggcaa agctcaccaa gttttttctg aaaaaggaat atttgcactt   8340
atgccactcc cagaaggcaa gggtgagatg aataaatgca cagtggtttg gtcaataaaa   8400
aatcaagttt tgggagatga gcctgtatct gagtttgtaa aaaataacat ttcttttttt   8460
gaatcaaagc ttaatgttag tctcagggtt aagtcagaaa ttttaagttt taaattatcg   8520
aaccatcatt ttgaaaacta tattagcgga cctattgttc ttcttggtga tgctgctcac   8580
tcaattcacc ccttagcagg tcaaggtatt aatctaggat ttgcagatgc agatactttt   8640
tgtgaagagg taattagttc ttataaaaaa gggattgcct ttaatgagaa atcagtttta   8700
aaaagatatg agattagaag aaaaagtatg aactttttaa tgttgaagtc tatggacttt   8760
tttgtggatt tatttggttc agaaaattta tatctaaggc tgatcagaaa tttaggtatt   8820
tcttcgttaa ataaatcaaa gtttgttaaa gcattcttta taagacatgc ctctggaatg   8880
aataagtttt aaatttgtat taaacttttt gacctttagc tctaagttct ttaagaactt   8940
cactaatgcc ttttttatca atgattctca taccttttgc agatacttta agatttacga   9000
acctgttctc agattcaacc caaaatttgt gtgtgtgaag attaggaaaa aactttcttt   9060
tagtcctatt tttagcgtga gaaacattgt ttcctgactg tggtatctta cctgttactt   9120
gacatatttt actcattgaa acgcgatttt atagaacact gaggaactta gcaatactat   9180
tgtgaaacaa atttatttat tacggcatgc acaatctgac tgggagagct ctaatcagaa   9240
agattttgat agaccattag caagaaaagg cattgaagaa gcaaataaaa tatcatgtta   9300
```

-continued

```
ctgcaaatct cattcaattt tagtagataa aatattctgt agcactgcag aaagaactaa   9360
gcagactttt gatatatgca gtgatgggct taattatcca atagctgaag cagtctatac   9420
tgatgagctt tacttttctg gccctggtga gatcgttaag cttatccaaa gtttaagtga   9480
attcatttcc tctgttttaa taataggcca caatccatca atgcaaatgt acatagatgc   9540
tatttcagaa aatcctcata ttacgtattc aacatgcggg ctggcagaaa ttctcgttga   9600
aagttcatgg aaagacttat ctttaaaaaa atgtaagtta aaatctttta ttcaaccagg   9660
agagctttaa aaattgaaaa acataaaaat taagatcatt aacccactaa tgggatccaa   9720
gataccctta cctcaatatg aaacaaaggg ctcggcagga ttggatttaa gggcatgcct   9780
agatagtaat ctcagccttc aagcaggaac atctcagttg atacctattg gttttgcaat   9840
gtacttagaa gatcccggtc ttgcagcaat ggttatacct agatcaggtt taggttctaa   9900
gcatggaatc gttcttggta atctggttgg gttgattgat tcagactatc aaggagagct   9960
aatggttcct gcctggaata gatcagatac agattttgag attaatcctg gagacaggat  10020
tgcacaaatg attatagttc cagtgattca agcagatttt gaaattgtag acgagttcaa  10080
tgagactcag aggggagaaa agggttttgg aagttcaggt ataaattgat aaatttactt  10140
tttcttgcca aatctttctt caaatttctg aactcttccg ccagtatcaa taattttttg  10200
cttaccggta taaaaaggat gagaagcaga ggatatatca agagggtagt atgggtatgt  10260
ttttccatct tcccattctt tcgtttgagt cgtatctaat gttgaacgaa tgagaaagaa  10320
cttatcagca ctagcgtcat ggaataaaac ttcacggtat tcaggatgta tatctttttt  10380
cataataaaa tcaaaatttg gatgagaact ataacaaaaa acaacttctt ttcaatcaaa  10440
acatgaaaat tttttactat gacatagctg tttcattgcc tctaaggcaa tgctttactt  10500
atagttctga gcttaaaatt acaaaaggaa cccgcgtgtc agttcctttt ggtaaaagga  10560
agattgtagg agtggttata aaaaatattc aaaagccaga tttcctaaaa aaagcgggag  10620
ctataaaaaa aattatcgct gtacttgatg aatatccttt gttcgacaag ccaatttttg  10680
attctatatt gtggtcttct gattactatc atcatcctat tggtgaggtt tttaatacct  10740
ttatacccac cgaattaaga aaaattaata ataaaaaaat tgaagcttta agagaatttt  10800
ctgaatattc agtaaatgag gatgataaga aattcgattt aaccaaggat caagaaaaag  10860
cagtcaaggc gctttctaaa tctaaaggat tttcacccac tttattatat ggagttacag  10920
ggtctggaaa aacagaagtt tacttaagag ttgccgaaac ttttattaaa aataataagt  10980
cagtattagt tttagttcca gaaataaatt taacccccca attgctctcg cgatttgaga  11040
atagatttaa tggtgaaatt ggcatatatc attctaagca aacagcagct aagagattaa  11100
agacttggct aaaagctaaa tttggttcta taaaaataat agtaggaact cgatcttcgg  11160
ctttagtgcc tttagataac attggtttaa taattatcga tgaagagcat gaccaatcat  11220
ttaggcagtc agaagggttt aaattctctg ctagagactt aagtataaaa agggcacagc  11280
ttgcagatat tccaattatt ttgggatcag caaccccttc gctgcaaact ttaaaacttg  11340
taaaagaaaa taaatttata agagttgata ttcctaatcg agttgatgga aacaagcctc  11400
ctaaattaat agccttagat atcaataaca gccctttaat aggcggagtt gctaaagaga  11460
caattgaagc aatgcaatca accatagaca gaggagaaca ggttctagtt tttattaata  11520
gacgaggatt cgctccactc tatcaatgta gtagttgtgg gtgggtagca gattgtaaat  11580
cttgtgatac aaatttagtc ttccaccagg caagaaatag attaatttgt cataggtgtg  11640
```

-continued

```
aatctgccta ctctgttaat ttgtcttgtc cggcatgcaa gtctaatgac tttaatatgt  11700
atggagctgg aacagagaga gttgaagaag ttcttaaaag cagctttgta aagactccaa  11760
taattagagt tgatcatgac tcaacaaaaa aagtgggagc tatggaggct atagttaaaa  11820
aaattcattc ctcagacgca gcaattttag ttggaactca aatgcttgca aaaggacatg  11880
attttcctaa agtcacctta agcgttattt taaatgctga taatggcctt ataagcccag  11940
aaattaatgc attagagaaa atatctcaat tgcttattca ggtctctgga agagcaggaa  12000
gaaataataa tcttgcaaaa gttattattc aaacaagata tcctgatgat ataaatctta  12060
ataaaattaa gacaggagat tatatgaaat ttgcttctca atgcctaagt accaatgagc  12120
aaatgaactt acctccattt actactttat gtctgcttag gtgctcatca ccaactcaaa  12180
agagtaatgt agatttccta gagaaagctg ttttaatttt atccaatagg actgatataa  12240
atgttattgg tcccttgcct tcattagttt cgaagtcgaa aggaaattat aggcaccaag  12300
tctatatcca tgcaccaaag aagacttttt taaataaggt attaaagttt ttgacaacag  12360
agtttgaaaa atggccggaa tctaataagg ttaagtggtc tttcgacatt gatccaatag  12420
acttaagcta aatattaatc ttaattaatt gtcctgggta tattggttta ttgtttagtt  12480
tattctctgt attaatttct tctacagtca ccccaaatct tatcgctatt tctgataaga  12540
catccccttt ttgtattttg taagtcacaa agcctggatc aatactcata aaggtatttg  12600
ctttaggttt gtccttaaaa tagttatgta ttcctaggaa aacagatctt gcaatcattc  12660
ttctccctgg cttgcccttt aatctttgtg cgtcttcagg gttggttata aaccctgact  12720
caaccaatac agaaggtata tcaatagact taagaactct gaaatcagcg tactcaacat  12780
tctttttatg aatttttgtg aaagggtctc ttttaagttg atccaatatc ttagttccta  12840
aaattttact ttcagaaatt tttttcttat atatttctgg ataggtttgt cttgccgcat  12900
cctcatcaaa atcaactggc tttagatttt ttatatcagc ctgtattctt tccctttgtt  12960
ttttagataa gttcctagca acagtacttg aagcttcatc tgaccatata aaaacagaag  13020
cacccttac ggaagataat ctaaacccat cagcatggat tgaaacaaaa atatctgctc  13080
catatttcct agcatcctgg tatctattat ttaaatctaa tgtctcatct ccatctctaa  13140
tcatcaccgg tctgtaccca taagtatctc ttaaggttct ttctaactcc ttcgcaataa  13200
gtaacgtcac atctttttct aaaatattat ttgggccaac cgcaccaggg tatttaccac  13260
cgtgacccgc atctatagca acaacaatat ctctaatact tttattgagg tttttatttc  13320
ttttcacctt aagctctaat tttatatttt ctgtatttat agtctgagtt gggttttgcc  13380
aatggactga ttcatataaa tcaacaacga ttctggtaag acttccatcc tgagatgctc  13440
ttactttttt gattggatag ttgtatggaa catttatctc ggtcggaagg ctcgattgat  13500
taatttccat gacaattcta gagggatttt taaagaataa gaccttacca atgaaacttt  13560
atctagacta aagttaatac taatttcatt gttacccatg tcttgtattt catcgaagaa  13620
aacatcattt ccgctgataa aaaaagatag aaaaccaagg attgccaatc tattcataag  13680
tttttaacca ttctttaaag ccattgtcac cagaaattaa agaaacctct cttccttcag  13740
gaagatggct gaaaattatt tttagatcaa aacttctttc atgttgaagc ctttcaggcc  13800
actcaattag cactactttc ttagagttta tttttctact tagatcaaat atatcaatat  13860
cttctgcttc gttagttcta taaagatcaa tatgcaaaaa cattaaatta ttaaaatcat  13920
attcctcgca gagagtgtaa gttggacttt ttacaagatc cttccatcca caattttttta  13980
taatagatct agatataaag gttttgcctg ctcctaagtc tccctcaaga tgtatttcaa  14040
```

-continued

```
tttcttgcga agaagattta agtatctcca tagctatttt tgaccctagt tggtttgtag  14100
cctcgtcatt tataagagta agttttttca tcgatttatt aattgtctta ttataggtat  14160
taaactagag gcatttaagc ctatttcacc aatatctacc ttaaatttta aacctgcctc  14220
cgaatgaaca gcaacagcaa taatgctcgc atttcttata tcaagacctt gggcaagaag  14280
agcagtcaaa acaccagcca gaacgtcacc agttcctcct gaagcaagtt caggtccgcc  14340
gcacgcgcat ataaaagact tgttatttgt tgagtcaaag accaccgttc ccattccttt  14400
taatatgaca atagaagccc cataagtgtc tgcaatttgc ttggcagcag aaatcctatc  14460
tctttgaact tcttcaatag atatgtttag taatatagcg gcctctcctg gatggggcgt  14520
catcaagatt gttttattgg attttttgat taaagatttt gatgatgcca cgatgtgtaa  14580
agcacctgca tctaatataa tttttgaatt atttgcagac tttaatattt tacccaatat  14640
agtttttgca aaagcagtat tagcaattcc tggtccatac aatataacgc tatgatcttt  14700
aatttttaaa tctatatcga ccccttcaac catatcaaca ccaattgcca ttacctcagg  14760
gtttcttaat aaagatgggc ttacattaga cgtgtctgtg acgagagtta ctagtccaga  14820
gccacaaaat aaacttgcct cagatgcaag tattccggcg ccacccatgc ctggggagcc  14880
agcgcatatc aaaacttttc caaaattacc tttatggcta tcctttgctc tattgggcag  14940
aagatttttt aattcttgaa aggtaaaact ttgcaatata gacatgaaat tacttaagct  15000
aaattatgtt gaatgctaaa aattcattct tcagcgaaat aaccaatcct atcggaatgg  15060
aatgatccca taaaaatttt ttcgtcatga ggcactgcaa tagtgggtag gccaaaaact  15120
gttctagaaa atgaaaactt atcttctctc ttaagtgttt tttgattaag tttatgaatg  15180
gagaagggta gagaacaatt tgttttttct gcacaattac caaaatcatt agcctgtaaa  15240
tctaaagaag ttaaccaaac cgaaccgtct tttaaaaaga tattatctgg actctgaata  15300
aaataactac ctgttttagt attttgatta atatcgtaaa cagataaatt gtcaccttga  15360
ttatagttaa cataaagaag tccagagccc tcatctagca aaattccatt aggcccactt  15420
ccatctgttc catcaacttt attaaaatta ttgtcactcc aaagtactac atgccctgaa  15480
atacttttaa ataatgaatt cattaaccat tctttcatgc tgatatctct tttatacata  15540
tgagatgcat aaaaacttcc atctttttta agggcaacat cattgaaata atattggtca  15600
gggaccctaa tacagccccg ccatatcata tcccatgaag attcattttt tataatttca  15660
aacatttcaa tcgactcaaa tggcgaatga ttaattacag ctagttgata gaagccttca  15720
tcattttcaa caagatctat tccgtgggga ttgaatatgt ctagctcgcc tcttatgcat  15780
gaagcgtcac cccaagagct ttctccaaaa gtaatttttg gtaccttttt ttcataggta  15840
tttaaatcca ttaaggcaaa gtaaccaggg gtatgttctg catatggacc gatccctcca  15900
aattcagaaa taaagaagaa tttattatca ggcgtaatca caatatcttc tgggtttgag  15960
aaattacaaa taaccttgat acggtcatcg gattcacact tactaatatc catttggggg  16020
cctatatagt cagtagatac gacagttaca gaaataaata aataaagaat agaaaccggg  16080
acggtaatct tataatagtg ctttataaaa atttctaaaa tctttgaagc atgatttgga  16140
agtgcgatca gccaaacccc ttttaaaaaa gatagagccc ccataacaac aaaaattact  16200
gaccatagcc tgtcagacca ttccggctga agaagaccag ttaaaaaaag aatcatccca  16260
aagaataaag ctaaatagcc tgagattttg actttcgatc caacaaattt cgaaaagaga  16320
tatgtataaa gaggctttat aagaactagt aaaccacagg ccaagaaaaa gaatgctaag  16380
```

-continued

```
tagtaattca taagttagtt tttatataaa tgctccttaa taatactaac aagttctaag  16440
ggcttgtcca atggaacatg gtgagcagct ccaggaaccc cctcaaaagt cataatgtca  16500
ccatatgtat ttttaatatt gtccaagata cttccggagg ttaataagct gtcttcaccg  16560
tggatgaaca aagcagggca gccaaatgaa aatgtgtaac cgaataacct ttcaagactg  16620
ctaaacatga catcatcaaa tttccatctc cacccagcct caatattttt tactgagtgc  16680
tcagcaatgt atcttaagta ccaatcattc gtacaatctt gcttaggcat taacctaaac  16740
cttttaataa tatctgtctt gtcttgatag tgcttgatca ttctgagagg agaagagtgt  16800
tgattcgggt cataatccgg tggtcttata aatgtatcaa taataataat attatttatt  16860
agatcctttc tttcagatgc aacgtaacca gcaacatgtc cgccgaggga gtgtccaaca  16920
ataaaaatat ttgaaatatt ttttttatcc ttttcctttt caattacaga gacaatacat  16980
tctccaaaat ctttaatgcc atatgaatct ctaaaagaag agtcacccat gccaggaaga  17040
tctattgcaa ctatatttgc gcagtctcta aagtggggcg caataggatc ccaccatttt  17100
ttatgagcac ctgttccgtg aataagaatt attaaatctt tgctttcatc tttggagttc  17160
cagctagaat aggatatatc cccatgagga ttcttgataa tctctgagct aggcttgtcc  17220
tcaatggcat ctttgaacca ctgtggggca tgaataatgt cttgatttag attgttagtt  17280
atttccataa acagtattct aagctataaa aaataaaaat atgaataaac ttaatttaac  17340
gccagcagca actgttttag tcctaaagga ttctcctgat gggatggaag ttttgatggt  17400
aaaaagatca agtaggcctc ccttcggaga cctttttgtt ttcccgggcg gcaagattga  17460
cgaaggtgat ttcaataata agatagaaga tttttgtgag ggcgtgactg ataaagaggc  17520
ctccataaat cttggattag attctggagg tctagcatat tgggttgcat gtattagaga  17580
atgctttgag gaggttggaa ttttacttgc taaaaaaaag agtggggaag atcttgatct  17640
agatggagtc gataaacata aatatcaaaa atatagagag atgttgttaa ataatgaaat  17700
tgatttatat aaaatctgtt tagaagaaaa tttaattcta atgcctcaac aaatagcccc  17760
tttctcgcat tggataaccc ctgaaataga aactaggaga tttgatacac gttttttat  17820
tgcccacctc cccaagcatc agaccggaga acatgatggt agtgagctca tagacagtgt  17880
ttggatttca ccaaaagaag cgctcaaaaa atctcgttcg ggtgagatgc ctatgattat  17940
gcctacaata aaaaatttgg aacaatgtgc acaatttgat tcgggctcta agcttttaga  18000
aaatcagagg aatctctcaa atgaggatat cccaccaatc ctgccaaagt tttttaaaga  18060
agatggtgag tggaggggtc tattgcctgg agataaaggg tatgaggatc attaaataat  18120
atggacttaa ttactaaaat aacagctccc aaccctggtg ttttcactgg gggtgggact  18180
aatacttatt tgattggcaa agatgatata acccttgtcg accctggtcc aaatatatct  18240
gagcatctag atgaaattat caaagcaggg gatgggaaaa taaaaagaat ctttgttact  18300
catacccata cagatcattc cccagccgca ttgcctttat caaaaactct taatgttcca  18360
atgtacggaa ggctagtaga tggtgaatcc tcatgggagg atgaaacatt tatcccagat  18420
attattttaa atgataaaga tattattgag acagacgaat atacgttaga agtaatacat  18480
actcctgggc acgcatctaa tcatttatgc tttttaataa aagatacgaa atgccttcta  18540
acaggcgatc acattatgga cgggtctacg gttgttattg ggccaccaga tggcaatatg  18600
acaagctata tcaattcatt agaaaagtta ctagattttg atattgattg ctttgcgcct  18660
gggcatggaa attatattca tgagcctgag aaaaccattc aatcaattat taggcacaga  18720
ctaacaagag aaagaaaagc tcttagaaag ctaggagagg caggaatctc atcattagat  18780
```

-continued

```
aaacttacta agcttgttta tgatgatgtg tcagagatgc tccatcctat agctaaatat  18840
agtctagaag cacatttatt aaagcttata gatgaaaaga aagttaaatt agataaagat  18900
ctattcgaaa taatttaatc ctttttattt ttatgtaaga ctttctcctc aatagcttct  18960
atatcaatat catcaattga gtcttcgtta ttatcaggta tctttttac atctttttca  19020
attttaaggt cgataggaga ggctccaaga tcaaaagtta gctcccttac attttttgaa  19080
atagtatcct caacacagtc atcttgatcg tatgcctcac gggtctctcc tttatcatta  19140
atgggaaagg gtctttgggg agggcccatt tgcatgcatt taatagtagc aactggtgag  19200
tagtaatcgt cactagaata taacttatca agttcttttg gtgatattga gcaaccaata  19260
attccaaata gaataaatgg cgctaagagt cttttcataa actttgtttg ttttctataa  19320
gagactcaac aaccgaagga tcggcaaggg ttgtcgtgtc tcctaaatta gatagatcat  19380
tctcagcaat ctttctaaga attctgcgca taatttttcc cgatcttgtt ttaggcaagc  19440
ctggagcatt ttgaattaaa tctggttttg caatagctcc aatttcttta gcaacaaatt  19500
gtttcaattc ataactaaag ttgtcatcaa atgattcatt tatcattaaa gtaacaaaag  19560
catatattcc ttgcccctta attggatgat caaaaccaac aacagctgct tcagcaattt  19620
tagggtggag cacaagagca ctttcaattt cagctgtacc tagtctgtgg ccagaaacat  19680
taagaacatc atcaactctt ccggttatcc agaagtatcc atcctcgtct cgcctggctc  19740
catcaccagt aaagtaaata tctttataca taccaaaata ggtgtcgatc attctttggt  19800
gatcaccata aatacttcta atttgactag gccaagattg ctcaataact aaattacctg  19860
cattagagcc ttctagcgta tttccatgct cgtcatagag agatggctta actccgaaga  19920
agggcagagt tgctgaccca ggttttgttg gagtaatacc cgctattgga gagataagta  19980
cagaaccagt ttcggtttgc caccaagtat caataacctc gcaattagat ttaccgacaa  20040
cactgtagta ccaatcccac gcctctggat taattggctc tccaactgta cctaaaattc  20100
ttaggctatc tctttttgtc tttttaacag gatcatcgcc ttgggccatc agagctctaa  20160
tggcagttgg agctgtataa aaaatactaa tgtcatgctt atcgcatatc tcccaacacc  20220
ttgatgctga agggtaggtt ggcactcctt caaacataag tgttgttgct ccatttgaaa  20280
gaggtccgta caagatataa gtatgtcctg ttatccatcc cacatctgca gtacaccagt  20340
atttgtcctc tggccttatt ccaaaaagat atttgaaact aatatgagcg cctaatagat  20400
aacctgcagt agtatgtaga acaccctttg gcttgcctgt agagcctgat gtatagagaa  20460
tgaaaagagg gtcttcggaa tccataggct ctggagcaca cttattagaa acatctttaa  20520
caagatcttc ataccaaaca tctttttat catcccaatt aatttcgcca ccagttcttt  20580
ttataaccag tgtattttta acatctggac agcccagaag agcctcatct acattagatt  20640
taagtggcac ttttttgccg ccccttaaac cttcatcagc agttataaca attttacaat  20700
cagcatcaag aattctatct ttgagtgatt ctggagaaaa gccaccaaag acaacagagt  20760
gcacggcacc tattcgcgtg caagcaagca ttgcgaacgc agtctcaatg atcataggca  20820
tataaataca aactctcgag ccctttgaa cacccaggtc ttttaaaaca ttagcgaact  20880
tacatacttc gtcatggagc tctttgtagg tcaattcttt agaatcagca gggtcatctc  20940
cttcccatat taatgctatt ttgtttggat cattttctaa atgcctatcg atgcagttta  21000
agctaatatt tgttttacca ccctcaaacc acttcgcatt attaaattga ttattgaatg  21060
ttgttttgaa gtcttccatc cagcttatgt tttcgtttgc tagattttta aaaaatttag  21120
```

-continued aaggatcttc tatggattgc ttgtaaagtt ctttgtattc atcaaagtct tttatataag 21180
gattacttga atgttttggg ctataaagct ttcgaggcat tcttaaataa ttgaaggttg 21240
ggggttaatg aaattctttc ctttgggatt ggacattatt tttgtaatga gcgattcgta 21300
atcgctatca ttggtttcta aattaatatc tgcagcatta attattaata aaggggcaga 21360
actatagtct aagaaaaacc ttgagtatgc atcattcagt ctttccaggt agtcaagagt 21420
tagatattgt tcgttaatat ttcctctctt agtaatcctg tcttttaaca catcaatagg 21480
tgcctgaaga tagattacta ggtcgggtgt tggcgcgtcc agggttagat ggtcatatac 21540
tttgtcatat agatccattt cctcgttaga aagagtaacc tcagcgaata atcgatcttt 21600
ttctattaaa aaatcagcaa ccctcactgt ttcaaaaagg cttctttgtt taagatcttg 21660
aatttgttgc attctttgaa acaagaagaa aagctgagtg gctagagctg attggcttgg 21720
gtttttataa aaattcttta agaagggatt ctctgccggt tgttctaaaa aagaatcata 21780
attaaatgtt tcggctatct tatttgctaa agtagttttc ccaacaccta tcggtccttc 21840
aattgcgata tattttggaa gtggtacttc tttaatagct gggttcattt ataacgtata 21900
gtttttatcc tagattatct caactcgtta tagaagccaa atatttttgc agattcttca 21960
tcactttttt cattcatctc agcaataatg gttcctctca atgagtcatc atttttttgg 22020
aaatcagtcc accacttccc aataccactc ttgtctccag aagctctctc tcttacaagg 22080
agaaaatcat atgcagctct aaaccttgga tgtcgaagag ttttatatgg ctggctacca 22140
attctgctat gaagttttaa ttgaagtacc caaatatcct taatatagct tgaaaatttt 22200
cttggtattg ctgtgatttt ttgttgttcg cgaagtacac catccataga tcggaaaaat 22260
tttctcacat taatttctcc attcttagaa cactttttca ataacgaggg ccataacaat 22320
gcagccataa gaaagcctgg tgtaattgac tgttggtttt taaccctatc atcagtattt 22380
cttagagcat gtgtcataac attgctggca aagtcattcc tacttggatc agaaaggata 22440
agatatttat ttaaatgaaa tgagcagagt ttttcaaaat tcttttcacc cattccattc 22500
aaaaatattt tgcagaactc atcaaacaat ctagcgtttg agatgcctga taaaagatgg 22560
cctttatcat agatggcatc cttaaccaga ttatctatct taaaattgag tttgttacta 22620
aatcttatag ctcttaagct tctcactgga tcttcttcga atcgtctttg gggatctcca 22680
atagatacaa taaccttctt gtgtatatgc ttaagcccat cgttatgatc ttctattttt 22740
tttgtaacag gacagtagta aagggcattc acagtaaaat ctcttctatg acaatcttgt 22800
tcaagagtgc cccaattatt atctctaaga atctttcctg tcgaatcagt aacaatattt 22860
tcaccatctt cctgatcact tcctgatctg aaagttgcta cttcaagcaa ttcactccta 22920
ttaaaaacat gaaccaattt aaatcttttg ccaattattc ttgaagcttt aaatgttttc 22980
ctgatctgct caggcgtggc attagtggct atatcgaaat cttttggctc tagtcccgtt 23040
agtgcatcgc gaacgcaccc accaaccaga taggcctgaa aattattttt ttgaaggtct 23100
tgaacgacag atatagcaaa tttacttatc ttattattat ctatcaaatc taattatgaa 23160
tttttatgat ttaagggcat tagccattta gctgcttttc tttaatttcg tcaagtgttt 23220
tgcaatgaat gcaatgagtt gcagttggtc tagcttcaag cctcttaatt ccaatttcat 23280
caccacagga ttcgcaccaa ccataatcat cttgcttaat ttgttcaata gatagaccta 23340
ttttgctgat aagttttctc tctctatctc tggttcttaa ttcaaaagca aactcttcct 23400
cttgagaagc cctgtctact gggtctgcat aggtttcacc tttagctcta agatgatcaa 23460 aagtttttttg catttcatcc ttaagatgtt ctttccaaag aagaagaacg gcaacaaaat 23520

-continued

```
gtttcttcat tgctgcactc atatattttt cacccttctt agatttataa ggtgcaattt  23580
tagatttatt attagctatt gttgcttttg cagacttctt ggctgcaact tttttaactg  23640
gagctttttt ggtaacagtt tttttaactg tagctttttt ggcaacagtt tttttaactg  23700
gagctttttt tactgtcttg gatttttttt cgaccatgta agattttata gaattttagg  23760
gtggagaaaa tatcagatac tgacaaaatt agctagtcat tttttaattt atttaatact  23820
ttcaagtacc catccgagct aagtcttggc ccaaatgtct caacaacctt ggaagatgca  23880
tagtttgcaa acttagcaca tgcttcaata ttattccctt gaaggtaggc atgcataaac  23940
gatccggcaa acatatcacc agctccattg gtatctattg gagttatttc ttctgcttga  24000
gcatgcttct caaccccttt atctataaca acacttccat cggcgccttt tgtaatagca  24060
gtcatatagg gcttttcttt ataaaagcta acagcatcat caaggctttc tttaccagaa  24120
aaagcaacag cttcatcatc attacagaag atcatatcta ttccatatga ctctattaaa  24180
tcaaattttt ctttaaaacc atgaacaata cctgcatcag aaagagacaa ggctttcttt  24240
acgtccttgt ctttaaggtg ctctaagact gaaataacag cattaaagtt atcgtcactt  24300
gttaccatgt agccttcgat ataaaaaatt tttgaatttt ctacaacatc aaaatctata  24360
tctgatttac caagatacgc actaactcca agcatgctgc tcatagttct cttagcgtca  24420
ggagtaacta aaattaagca tttcccagtt ggttgatctg tattttcaga gctgacacca  24480
atatgtttga ctccagccga cctgagacta tcaagatagt ttcttccatc ttcatcatca  24540
gaaactctgc atacatgatg gcaattcgaa ccataatttg ctgcagcaac aagagaattg  24600
gttgcagagc caccgcaatc agaaatcgat tcggctccca tttcaataag tttgctaatt  24660
ataggtgcct gttcttcaga agatgaaaga gtcatagagt cggctacaag gcctacactt  24720
gataaaaatt catggctgac tttatattga gtatctacta aagcatttcc aagggcgcta  24780
atatcatatt tcatgtgtta ttccttttttg tattatttgt tttactgttt ctaacgttct  24840
attaatttct tgatccttat gcattgctga aatgaagcct gcttcatatt tagagggggc  24900
aaagtatatt ccacttctaa tacatgaatt taaaaaattt gaaaatagta catcatcagt  24960
ttttgcaaca tcattaatat tattagggag ttcttctgaa aaaaagaatc cgaacattcc  25020
accaattctg tttatagaaa acggaatacc tgactcaatc attaaggttt tcatcccatc  25080
caaaagcaca gatgcatttc tttctaactc tttaaacgga ttttctttaa tcaacaattg  25140
caacaaagca gttcctccag ccatagctag tggattgcca gacaaagttc ctgcttgata  25200
gacaggacca gaaggagcta gatagttcat aatttcttct ttgcctccaa aagctccaac  25260
aggaagaccg ccacctatta ctttccccaa agcagttaag tcaggagtaa tattataaat  25320
ttcttgagct ccgcctagcg aaactctaaa gccgctcatg acctcatcaa atattaaaat  25380
agaattattg gctgaggtgg tttccctcaa taactttaag aaatcttcat gacctggaac  25440
aaagcccata ttccctgcta ctggttcgac tattacggcc gctaagtcat cttttatctc  25500
attaaatatt tctaaaaact gttctttatt attgtattcg caactaaatg tatattttgc  25560
caaatctgca ggaacccctg gagagtcagg taagccaaag gtggcaaccc cagaacccgc  25620
cttaattaaa agagagtcaa catgaccgtg ataacagcca tcaaatttaa taattttatt  25680
ccttcctgta aaacctctgg ccaatctaat cgttgtcatg gttgcttcag tacctgaatt  25740
aaccattctt attttttcaa ttgaaggaat gcattttttta attagcctgg ccacatcaga  25800
ttcaagactt gtcggggcgc cataactagt tccaagcgca acttgatttt taattgcacc  25860
```

-continued

```
tacaatgtct gggtgtgaat gacccattat catcggaccc caagacccaa tataatcaat  25920
atattcatta tgatcagcat cataaaggta tgcgccggat gctctttcaa aaaatatagg  25980
attgccattg atatttttga atgcccttac tggtgaattt acccctccag gcataagagt  26040
cttggcctct ttgaataagg ctatggattt atcaatttta ttatgtgtca aagctaattc  26100
ttcttaattt ttaatttcga tatgatatca acttaattct tattatgtat ttaattgttt  26160
tgaaaattca tccacagtat tccagttggt gaactcataa gtatttgtaa catctgtagg  26220
accctttgta atccacataa tcaatctaat catgtgttta tctataaatt tatattttgg  26280
ataatctatt ttgcctgcaa agactgctaa tttcattggg ttccaaggag acagctctaa  26340
aaatttttgc atatacgggt ttgtttcagg tgtatttttt tcaggctttc tcgcaactac  26400
attaactgaa aagaaggcat tttcttttgt ttcaagacaa gcaacatttt tttgaataaa  26460
ttcataaagt tctggtttgt gtttgccata cctaatgctc gcaccaataa taattttatc  26520
aaattgatat aaatctaact ctactgcttt tgcaatatgt attatttttg aagattcaga  26580
cacatctaat ttagagaaaa tttttttaca aatttccaga gtttgcccat cggttgtaga  26640
gtagattagt agagttgatt tcataaatat attttatatt gttaattaaa aaatttcatg  26700
gcacgcgcaa aatataaaca aaaatatagt atatttaaaa aatgattaaa tatttattta  26760
ttatcgcttt attcatcagc aactttgcat atgcaaatat tgatgcagct aggtgcgcag  26820
ggattagttc agatcaagaa agacttgatt gctatgattt aatttttaaa gctaatgatg  26880
agctaccttt agatagtaat attaaaactc tcatcacacc agctatcaag gctgtgaccc  26940
cagctgattc aataaaaatt gaaaataaag caacaaaaga aaaggatttc gggcttccaa  27000
aaacaaaaat caaaaactct gcaaagaact caataaaaac ctcggtagta aggattaaaa  27060
aaacaaaaag tggtaaatta atttttactt tagaaaatga gcaagaatgg actgctgaaa  27120
cttcttatag agcaaggaat atgtttaaac cagaaaccgc agtcatttta gaagaggccc  27180
tggttagtgg tttttatatg attaatataa gtaataaaca gaaaattaga ataaagaggt  27240
tgaaatagca atgaccatac agagtatagc aacgaccgag ggtgccatga aaagaataag  27300
atctgttctg ggtcccaag atggctcaag cttcagggtt tatgttaccg gaggtgggtg  27360
ctctgggttt caatatggct tcaagtttga taacgatatt gcattcgatg atgatgttat  27420
aaattgtgga gatttctcgc ttttaataga ctctatgtcg taccccctatc tttatggatc  27480
aactctggat tttgttgaag atctctcagg ggctaaattc gttattaaaa acccaaatgc  27540
caaaacaaca tgcgggtgtg gagagtcatt tacagtttag attttgtaat tgaacccaaa  27600
agtcctttta cattcttgct tgatgtctga actatcagag cctcattact gactctttta  27660
tatcccatcc aggcaaatgc catggactca atagcaaaaa catcatggcc taaatcactt  27720
gagaggacga tatcattact agccatctca gaaattcttt ttaccagata cttgttatgg  27780
gcaccaccgc cacaaatgac aatgtcacaa ttattatgac catttttatg gattgaattt  27840
attatagatt ttgctgaaaa ttcaaccagg gtacatagaa tatcttcagc tttctttttt  27900
aagaatttct tggataatat ttttatatta aagagctctt tgcctgttga ttttggacat  27960
tttcttttaa aaaaattatt ttgaagcaat cttcctaact caatgtgatc tacttttcct  28020
ttggctgcaa ttgcaccatt tttatcaaaa ggaatctgaa gaaaatcact acaatatgca  28080
tctaaaattg cattaccagg gcctacatca gttccccata tgtcatttct atttttttaca  28140
aatgagtaat ttgaaatccc ccctatattt aaaataattc gtgggtttct agctttataa  28200
aataattgat tatggaattc cggaacaaga ggggcgcctt cgccacccag agcaatatgc  28260
```

-continued

```
atatttctaa aatcacttac caccagaagg cccgtttctt ttgcaacaat atttggatca  28320
ccaatttgca tagaaaatgg aaatctctta ttaatttcat gcctaatggt ttgtccagaa  28380
atagcaacac actctataga tgatttctta attttactaa atccaatcgc ctcattaata  28440
gattttgaaa ataagaatcc tatctcttta ttgatagtgc ctaaatctga caacgagctt  28500
tcgttatttt caataagttt ttttactttt aatcttaggg attttgggaa tttaattgaa  28560
tggaaatact caagatgtat ttttgtacca atgctaagaa atgaaatatc aatagcgtca  28620
tgactagttc ctgtcattgc tccaatatag atctttttac tcattactac ttggagaaag  28680
tttattgaac tcctccattg ataatttatt attctttaat agtgtatcaa aacttgccct  28740
taaatttttt ggtactggtt cagctgatgg taattttact tttataggat ctattctttt  28800
cttacctatc ttaaactcat aatgtaaatg aggccctgtt gccagtcctg aactcccaac  28860
gaaaccaata gtatcgccct gagaaacttt tttgcctttt cttataccct tactaaattt  28920
ttctaaatga caatatctag tcgaatactc atttgtatga tttataacta tctcattacc  28980
acatccattc ctttgaccag aaaaagaaac aatcccatcg cctgtagttc tcaccggcga  29040
tcctcttttt gctgcataat cgactccatt gtgagctctt attgtatgaa gaacaggatg  29100
cattctgttt ggattaaaat gagaactaat atatgcaaaa tctaaagggg ctcttaaaaa  29160
ggccttttgc atattatttc cattttcatc aaagtactgt tttttactgg cttcagtgaa  29220
aaacctattt gcaaaatagg tattaccatt gttaataaac ttagcaatta cgatatcgcc  29280
attttttact ttctctccat cactataagg agtgtcataa attacatgaa attcgtcacc  29340
ctctctaata tcaaaaacga agtctacatc ccagccaaag atataagcaa agtccataat  29400
cacactttcg ggaatatttg catctagagc tgcctcataa aatgaggatt gaataatccc  29460
gctattgtaa gattcaatta actcaatact tttgcttata ttcttaaata ctatttctgg  29520
agtaaggcta attgaaatag aatttatttg atctttcatg atctcaattc tggttagctc  29580
ctcaccagaa tattcaaaga gcattttttc ccctggttta atgttagcaa tgatattttt  29640
ggagtctaat ctaaaaattt tataagcagt atttaaaggc actgaaaagt tttcaaaaat  29700
tattgaaaga ttttctccat cttgcacctc atgcatctga tatgttttcg tttgctcgag  29760
aggtatagag aatttttcag taatctcaat ttcttcaact ggcaaagatt catatgtttc  29820
tatatcaata taaagcatta atattaagac aatagaaaca gcaaaagaaa caagtaccgc  29880
tctttttgga actttttaa aacctatcat tagtcctctt gaatatttaa gagttcagtg  29940
ttgccaccaa atgctaccga gttctttgag acaacctttt cgttaagaaa ttgcagaagg  30000
taattaggcc caccagcctt ataaccgctg ccggatagat tttgtccacc aaaaggctga  30060
gaaccaacaa cagctcccac catatctcta tttatgtaaa tatttccaac attacacttg  30120
tcactaaata tgtcggccct tttttctact ctagtatgaa tacccattgt aaggccgaag  30180
ccactatcat taatattttc aattagtgca tccatttcat ttgatttaaa tctaacgata  30240
tgaagtattg gtccaaattg ctcgtctttt agatcagaaa tattatcaat ctcaattatt  30300
gttggagcta caaaattttc atctacatta tcagcagacc taaaaataga ataattctta  30360
tcttcaaaac ctttgacgta agcattgaga ctatcaagag atgttttgct aattattgga  30420
ccgatatctg tgtcaagatt ttgagggttt ccaattttta gttctttcat accaccctta  30480
atcattgata aaagatcgtc atatatttcg tcttgtacac agagaactct caaggcagag  30540
catcgctgtc cagagctatc aaatgctgaa cgaataatat catcggttgc ttgctcgaga  30600
```

-continued

```
agtgcgcttg aatcaacaat cattgaattt atgcctcctg tctctgcaat caaaggaata  30660
attgattcat ggttacttgc aaggctgctt tgaatttttt ttgctgtttt taaagacccg  30720
gtgaatgcaa cccctttgat gttattaacc tttgaaagca tgtcaccatg aatgccgtct  30780
cctaggatta aatttaaagc atcttttggg accccaatct catgaaattt gttcacaatg  30840
atgtagccaa gaattgaagt atgttctgag ggcttaactg ttactttatt tccacatgca  30900
agggctgcac ttatttgccc tataagtatt gcaacaggaa agttccatgg actaatacat  30960
aaaatatggc cttttggtga gtaagatagg gcattgatct cgccggtggg accctcaaga  31020
atatggtctt ctgtttggag gccaacagct tgttttgcat agtatctgag aaaatctata  31080
gcttctctaa tttcatcaat agtattttgt actgtttttc cggcttcatt cataaggtaa  31140
taaattagct cagaaggatt tgcttcaatg tcgtctgcaa ttttttctaa aatggatgct  31200
ctttttttcaa catgcatcaa agaccattca ctaatatttt gttcttcaag gctgcccttt  31260
atataatcta gatcatcata tgaggctgta ccaatatttc ttccatctgc aagagatgag  31320
atgtcatgag tattggtttt cttataatcc tttgctttat aaatcgatga agcctttatt  31380
tcttttgaat caaactttcc aagctcctct tcaagcattt ctaaattcac cctttcactt  31440
aaatcaaatc ctttagagtt cggtctgtca ttaaatatat ttcttggcat tggtatctct  31500
tttttttcat cctcaatttt taaatggggc cctctggcaa gccaagcaga atctgtttca  31560
ggatcaagta acctattaat aaatgagctg tttgctccat tttctaatag tcttcttaca  31620
agatagggta gcaagtcttt atatttgcca atcggcgcat aaattgaggt atttttttca  31680
gtatttaaga ttttgtttgc ggacttataa agcagctctc ccattccaaa tagtctttga  31740
aattcataat ccttatttga gccaagatga tggattgcag aaatggtatg tgcattatgt  31800
gtagcaaatt tagggtaaat tttttccaca ttaaaaattc tttttgcaca ggctaaataa  31860
gctaagtctg taacagattt ttttgtatag acaggataac catcatagcc atagatttga  31920
gcatgcttaa tttcataatc ccaatatgct ccttttacga gccgaacatg cataggtgct  31980
ctgttttcta gtagctcttc taaccaatct attgtggcta tagctctttt gccatatgcc  32040
tgaacagcaa taccaaatcc tttccagttt ttaatatttg gtgaaagggc catctcttta  32100
ataatctcta aactaacggc cagtctgtct tgctcctcag catcgattgt aatttctaca  32160
tctttagact ttgcatactc tgtgagctga ataagttttg gaagtagatc agactttatg  32220
tcttttagct ttttcatttc atatctagga gataaagctg atattttat tgagacacca  32280
ttaattgtat tttttgtcag atttatcttg ccgacttcat ctatagcatt cttataagac  32340
tgataataag tgtcggcttg ttcagcgttt cttgctgcct ctccaagcat gtcaaatgaa  32400
taaatttcat tttctatatt cttaattttt tttatgtcat caaaatctct gcccataaca  32460
aattcttgac tgagaatatg catggcacca actacagcat ttctaattgg aaactcgcca  32520
gattttgaga ttaaagaact taatagggcg cttgggtttt tggtccactc atcgggtgta  32580
gaaactacct tgcctgcaag aagaagaccc catgttgatg cattaacgaa aacactatcc  32640
gctttgttta aatgctctat ccacgcaccc tcagataact tctcagatat tattagatcc  32700
cttgtttttt tgtctgggat tcttagtatt gattcggcta aacacatcag agcaacacct  32760
tctttattat ctagcccata ttcgcttaga aatgcatcta gttttgttct ctcgctctta  32820
ttctctctgc aagcatcaat tattttattg agcatttttt gaaatcgaag ggtcatttaa  32880
aaaatcagaa ttactaataa gatctgaaac tatttcttgt tcaggataaa acttgttact  32940
tgttaatgtc atagctatta ttttaatctt atagtgccaa gtatcaactt actgattcta  33000
```

-continued

```
ttaatgactt aaaaacatta tgatagtcat atgagtgatg cacttaaatt aattaaacga  33060
ggaaccgacg agatcctcac agagtctgat ttaaaaaaga aattagattc tggaaaacag  33120
ctaatcatta aggcggggtt tgatccaaca gctccagacc ttcatttggg tcataccgta  33180
ttattaaata agctaagaca ttttcaagat cttgggcata aagtaatttt tctaattggt  33240
gattttactg gtcaaattgg agatccctcc ggtaaaaata aaactaggcc aacacttact  33300
tcagaagaat taatttcaaa tgcaaaaaca tatgagaaac aagtttttaa aattcttaaa  33360
aaagaattaa cagaagttaa atttaattct gagtggtgca acaagcttgg tgcagatggt  33420
ttgattggtc ttgcatcaaa atataatgtt gcaagaatgc tggagcgtga tgattttaat  33480
aaacgttata gcgcaaatca aagcatagct attcatgaat tttataccc ccttgttcaa  33540
ggatatgact ctgtagccct agaggctgat gtcgaatgcg gaggaacaga tcaaaaattt  33600
aatttgctag tagggagaga gctacaaaga tcctatggtc aagaacctca ggttgtttta  33660
actgtaccca ttctagaagg cttggacgga ataaataaaa tgtccaaatc attaaataac  33720
tttatagcaa tagatgaaga gcctaatgat atgttcggta aaataatgtc tatttcagac  33780
gagttaatgt ggagatggtt tgagttactc agctttacct cagagaaaga aataggagtt  33840
cttaagaaga aaatggaaga agggaccaac ccaagagata ttaagtttct tttagcagaa  33900
gagttagtag atagattcca ttcagagggt gatggttcga aatgcaagga agcttttctt  33960
caaagatttc aaaaaggtca aatgcctgat gacattcctt ccatgtcagt tgatgttggg  34020
gctgagggca ttccattagt aaacctttta aagaattgtg agatgacatc aagtacatct  34080
gaggcgatga gacttgttaa acaaggcgga gttaaaatcg actctgtaaa aatagaagat  34140
cctaaaatgc taatttcaaa aggccaggag tctatttatc aggttggcaa aagaaaattt  34200
ttaaaaatta aaacataatg aaaaataaat tagtccaaat atttcttctt ctttttatag  34260
ttgcgtgtaa tcaggatagc cctaatatta aacaaattag taatatgcag tattttattg  34320
ataatgaaat aagggaagga atctattctg ttgaaccagg cttgcaatac tcaattatcc  34380
aaaatggaga tcaaagttct gaatcaccat tgctgcagga tacaattaca gctcattttc  34440
acgggaccct cactgatggc tcagtttttt ggagttctgt tgaaatgggt gagcccttaa  34500
cagtcgaact atcaggtcta atagttgggt gccaaaaaat aatctctatg atgaagaaag  34560
gtgatgaatg gagagtttat atcgacccaa gtatggccta tggcgatgag ggccggcctg  34620
ggatacttc aaactcaatt cttatttttg atattgagtt attagatatc caaaaaaact  34680
aacccttatc tataacggat agagcgtatc cataaacctc agcaacctgg ttaataattt  34740
tatttttagg tgttccggct ccatgaccag ctcttccttc aattctaatt aatattggat  34800
tatcacaccc ctgggactct tgaagttttg ctgcaaactt gaatgaatga gagggtacta  34860
ctctatcatc tcttttagct gtagtaatca gagtagttgg atagcactca ccttcaacaa  34920
tattatgcag aggcgaataa gctaataagt tttcaaactc atctttctta tctggagagc  34980
catagtcact ttcccaggcc cagcctatag taaatttatg aaatctaagc atgtccaaga  35040
cgccaacttg tggaattgcg actttaaata aattaggatt ttgcaacatg gtcgcagcca  35100
ctagcaaacc tccattagag ccaccttgaa tagcggttga tgatggagaa ccaatttctt  35160
gtgcgtgtaa aaatttagca gaatatgcaa agtcatcaaa aacattttgt ttattaaaaa  35220
gcctgcctgc atcatgccag ttatcaccat attcaccacc acctcttaga ttaactacag  35280
caactattcc cccttggttc atccaagtga ggtagctttt actaaagcca ggtagtcttg  35340
```

-continued agatattaaa gccaccatat ccatataaaa gtattggagt attactgtct atttttaagg 35400
actttttgta actaagatgg atgggtattt gtgttccatc tttggatgga aagaatttaa 35460
agtcagatgt aaataaagtt gagtcgtgtc ctttaagatc ttctttccaa aaaagttctt 35520
gtgacatatc agttagatta attttgtata tttctcgagg agttacaaaa tttgtaaatg 35580
aaaaataaga tacctcatct tcaatttcac caccaaaacc acccattgtt ccttttcttt 35640
ctgttgctag cttattttta tatgctcctt ttaaatcaaa gaagtgaacc tcagtaaaag 35700
tatcaacgag ataagaaact acaatagaat tatttataaa gctaacacta ctaatagaat 35760
tagtactttc accaacgact tcattccaaa caaatgagcc attttttatt gtaagtgata 35820
ctacttttcc gttcgcagca ttttcagttg agtaaaacca aaaagtatca ttcttgcttt 35880
ctaaaaagct ataagcgcct attagctcat ctattaaagg aataaaaggc tgatcagggc 35940
ttagctgaac atagagtcta tttctttcat ctgtgccttc accaatagat agaaacttaa 36000
ttttagaatc ttttacaaca cttattcccc aactccatct tggcttttca ggattctcat 36060
aaacaatcac atcctcatct tgagcagtac caattttatg aaacattaac tttggagctg 36120
tattaatatc ttttaaaagc tcttccgatg gctcgtcgta tttttggtaa taaaatccag 36180
aatcatcatt ttcccatgaa gcaccagaaa atttagccca ttcaatccta tcatcaagag 36240
tttttcctga ttcaatatca agtactttcc aggttctcca atcagaccca ccatctgata 36300
ttgagaaagc tagaagagat gcatcattac taacgctggt acttgcaaga gagatagttc 36360
catcttctga gaactgattt ggatcaagta aaactctatc ttggcattct tcacagtcct 36420
taatcatcag cttgctttgt tgccatgacc catcattgaa ataataaaaa gtttttttgt 36480
taacctgata aggcatgctt atcgaatctg tatcccaaac ctcatctaaa ttcttagcaa 36540 tagattttttt atatttattt tggcctataa atttttgtgt gaaattattt tgtctctcga 36600
cccagtctgt tgagtcctca cttgtaaaat cctccatcca tctataagca tcttcgatta 36660
ggtatccatg gacttcttca ctaaaaggaa ctttatttga ttcagggtat tcaaaattat 36720
ctgtttgatt tgagcaacta actagaatta atagagctgc catgtatatg tatttattgc 36780
gcataaaaag cataatactt tacaattacc ttatgaatca attcaatcga gcatggcaac 36840
ttttacgcaa aaaattggaa gtttttttatt gtacttgccg cacccatcat gatgcttgaa 36900
atagcaatgg catcaatggt aaccccaata caaaacgtta ctcagcctga ggatattcta 36960
gaatttttca atgagaatat agcctttcta ggctctgtta gtctcttagg cgtagtttta 37020
agtatggctt ttatgggagc gctttttgtt tcgtatgcat ccatagaatc agaaaatgag 37080
attgagcctc taaatgcctt atttttaggc ataagaaaat tctttccact tctgggggct 37140
tatcttatag cttcagttgg tgtctttttt ggtatcttat tattaatact cccagctttt 37200
tatgtagcag caaggctttg catttttcct gcatttatta tgcttgaaga caaaggagct 37260
atagaatctc ttaaattatc ttgggaaaag acggatgagc atggcaccac tttgtttggg 37320
cttaccatta ccttcttttc tttaacaatg atttttgcat cagttgccca atccattata 37380
agtccgggat taatgcaatt agttgttctt gcaattattg aatatgtaat agtaattcca 37440
tggggctatg tatattttag tttatacaag tcattaaaaa gatattaggc agattaacta 37500
gaataaatta atacgaagct tttcgtttac aaaaaaacac accactctta taatccttcc 37560
tccgaagatt tgcactttgt taattcatgc aaacaacttt gggtctgtag ctcagcttgg 37620
ttagagcgca cccctgataa gggtgaggtc ggtggttcga gtccacccag acccaccatt 37680
ctttgaacat taacttttat ttcctttata cttattctta actaaataag gatagtatta 37740

-continued

```
tggctaaagg tttagacaag caaaaaaacg acaagaagaa aggcaaaact ctaaaagaaa  37800
aaagagcggc aaaaaaagaa aaaaagaaat agttttttgt agaagactat tattatctag  37860
tcgacctagg gccatcttta aaatctattt taaagaacaa cattattccg gtcactgagc  37920
ttactaaagc taaaatagaa aatattttta aaagaaggtt gtcgatatta tctctttctt  37980
tccaatccat aatatgaaac ccccacatca gatcccatat tttccattta ttagatctaa  38040
tggccacaac ctctgctgag taaacattaa tgtaaacatt taattcagta cctttaacat  38100
ttttactttt tactctataa attggcaatg atctgcctct atattcagat cctgattttt  38160
catttacaac ttcttcggta gcaaatggca aaagagttgt ttggcttgaa actgaatcta  38220
tagcatcttc catagaaatc tttgttaaag gctgcccaag catattcaga tacttagttg  38280
agccctttgt tgtgatgata acaatctctt gacctaatct ttttttgaat ttaacttctt  38340
tagctttctc tatttcaaaa tttaacttac ttaaatcaaa agatgtttca acatgattaa  38400
ggtattgctc gcctcttacg agctcaatct tattaaaagc aaagtatatg cctgagatag  38460
tccaaagtaa taactgaaga gagataaaaa aacttaggta cttatgaatt ttcctaacta  38520
aaaagttcat cttttcataa tcttcattat ttcatcaatt tttacatcaa attcgtcatc  38580
accttttaaa gattccttaa tgcattcacg caaatgggtt tttagaattt tgccctcaac  38640
agtaataatt gaattcttaa gtgcttttat ttgattaaga atatcaacgc agtattgacc  38700
ttcctcaacc attccttgaa cgcctcgcac ctggccctct attcttttta agcttattaa  38760
ttgctcttta tgacatggat gtttcatttt ataaaaacct cggaactata tacgtaaaaa  38820
ttgtagcgaa taaaaaaatt gctacagatg catagtacag atacctagat ttttttctag  38880
tttctgaaca tgctctgcct agttctgggt cagcagggca aggcatatga taagttttgt  38940
agttgatata tcctgcaatg acaatcatta ctaatgcaaa tagtgttatg taaagcttat  39000
attgagatag ggtaattaag aatggaaata cagttaccag gcttgcaaaa cttgccccag  39060
caccaagagc aacaaaaata gctggcaagg cacaacatat caaagtagaa gaagatgcaa  39120
ataatgaaaa aaaattcgac gccttatcat tcatagttat taaatttcta ggatttgaag  39180
atcagacata ttttggccat tagaaagaat cttcttttcg atctcagaga aggtgatttc  39240
ttttgcctta gaaaaggcaa tcactacttt tccattatca agatcaacat ctattctttt  39300
gacatcttta tcttttagaa aagtttttga aatacctctt gcacagaaat cacaaaccat  39360
tcccttcacg cttacgatcg ctatatttac atttgagagt ccttcaacaa atgcatcaaa  39420
cctctcaggg tttacatcaa gatcttttcc atcaaccatg gtttcatgta aatgaccttc  39480
atgagaatgc ccatgcatac cactatggtc attctccgcc gcaataaggc cgcttgaaag  39540
caaagtaatt aataataatt ttttcatatt tttctccttt taaaatctgt acataaaatg  39600
taaatcccag ctcgtatctg cgtcatagcc aaactcaaca agggcattac cataaaaaaa  39660
tttcaattct ggatacgtag atgatttatt tgttacagta tttttttttgg ttttaaccat  39720
aacccatgta tgtaaatcat tgtagtcagc aacgtaagga gcaaatccaa gttgaatata  39780
ttcttcttta tagtctttgc taaatttact gttaatatcc tttaacccaa agcccgcata  39840
ccacttccgg gtttcccagt ctccatggat accataaaaa ttatttttaa tacttccagg  39900
cacaattcct gattgaaaat ataaattcct ttgggatgta aaagtatttt ttctattcac  39960
caaataagta aaacgaaaat agttttctgt gttcttataa aatttatttt tagccctttc  40020
taggccaatg gaatatttgt aggttggaga gtagtggaaa taaatagaat cattaaaggt  40080
```

-continued atctgattta tacattatgg ttgttccgcc agagtaggat atcggtcttg catcagcatt 40140
aaagaccatt aaaaaaacta aaatgattat tttatatata cccatggggg gtatcttacc 40200
ataggattat aaattaattt caggcatctc tccaagcgcc cattttcaat gaaatcacca 40260
tcagaattcc aaaaataacc atagctatag cagatgcata aaaaatacta actagcccat 40320
atgagagcca gtaaacagct accaatgcta taacagaaaa tactataagc ctgatggccg 40380
tgattataat tggccatttc attgcattgg ctccctgaga tgcaaaatac agggaaagcc 40440
catatccttg aaatacataa catacaccaa ggatttgaat atactgcttt gtaactaata 40500
aggtctctgg atccgatgta aaaatactaa tccaaagatt tggtgttagt gctaaagcta 40560
gaccgataac agccgaaagc aatccagctg ttgttgcacc aaccatgcct attttttctg 40620
ctcgctctat atttttggca cctatatttg ttccaaccat ggctgtcata gcagtcccaa 40680
tgccgaacac aattgggatt aataagaact ctacccttga accaattcca taaccggcaa 40740
tagcagacgt tccaaattga ccaatgagtc ctgtcagtaa aagaactgtt gcaactgtca 40800
ttattggcga aagagatgcg ggtaaggcaa cagaaaaaat atcttcgaat aattctcttt 40860
caattgttag tcttttgagc ttaagcctta caggcgatga agggctcgaa atttttatta 40920
aagttactaa tgccataaaa cctgaagtaa ctatcattga ccaagcagat cccacaagcc 40980
caagtttagg tagaccgaat gatcctaata taaatccagc agagaaaaaa acttgtatac 41040
ctgcacaaat taccgttagg actgcaggaa attgcatatc tcccatccct cttagggcgg 41100
cggttaagct acctgatagc caaacaacta ttgctcccaa taaatagaca aaacaataag 41160
ctaaagactc ctctaataat gcacctgttc cacctaatat tcttaataga ggctctccaa 41220
aaataaaaaa gataattaaa aaagctaaag ctccaaagca agatatatac aaagaatgcc 41280
ataataattt ttcagcccta ggcttgtctg cggctccaag acttcttgca atagaagatg 41340
tgaccgctcc tccaagagca ccaaatgcca tctgctgagt cagcatgatt gcaggaaatg 41400
ccaaagtaac agcagctaat ggagttatgc caagttgact aataaaccag aattcagcaa 41460
gaacaaccac agcatttatt aaaaatgcaa cagtattagg tgctgacatt ttaatcagca 41520
aaggaaatat tggatctttt aaaaattgct ctgttctctt gtccataacc ttctcattta 41580
ttaatattta tttggttaaa gggtgaaaga gaacacgttc tcaggattca cgaatcttta 41640
aataataata acagctttta gttaatttaa tttttaaaaa caaccaaatc tattatctgc 41700
tagattttat tttttaaaca tattaatatc taatttaatt gcaaaggggt ggccatttcg 41760
gcctgagatc cttggaaact ctttgaacct gatccataca ataatggcgg aggaattgca 41820
tgaaaatcat taaaaatcat ttattttatt caataatctt actatatttt tttagtctag 41880
agacgagctc tcaagctata gaagaagtta ttatcaaagg agactggaga gaaactagtc 41940
tgtcagcaga agactcaagc attgcagtcc ttgatagtaa attaatagaa tcccaggctt 42000
taaagcactt tgaaaacctt tcgtacctag taccaaattt aaattttgct gcaagtgatt 42060
ctagagcaag acatttccag ataagaggaa ttggagaaag atctggctat gaaagaactc 42120
caaactctgc agtaggttta ctgattgatg atatagactt ttctgggcaa ggtggaattg 42180
ccacaacttt tgatgttgat caaattgaag ttcacagagg cccccaagga gcaagaatag 42240
ggtctagcgc aatggcgggg ctcatatata tttctacaaa agacccaaca gaaagctttg 42300
aagggaaggg tgaaatagtt atggggtcat atggaacttt taataccgga attgctgttg 42360
gcggtcctgt aaattttaat aaagacctca cttataggtt agctataaag aaagattatt 42420
ctgacggatt taggaagaat atttttctca acaagtctga tacttctaag aaagatgaga 42480

-continued

```
gcacatttag attaaaagtg aattgggtaa ctgataacca aaccacttat aagtttctta  42540
tatctcaaat agagttagat gatcctgcag atatatggac tatagatggg agtcttaata  42600
cattatctga taagcctgga atggactctc aaaaaagtaa tgcctatggg gtaaaaattt  42660
atcatcaatt taaaaaattt gaatttcaaa gcctatcaag cttaacgaat actgatgtca  42720
ttcttagtta tgatgctgat tggggcaacc ctgagtcgca ttcacccttt atttatgact  42780
atttttcaga aactacaaga aaaagagata cttttagtca agaatttaga cttgtatccc  42840
aatttgcaga taaaaataca gaaaaaagca tcgaatgggt cgttggggct agttttgtag  42900
atataaatga aacaaatgct aaaaaagata ctggtattta tggagatcca tcagacccat  42960
atggtcctta ttttagtaac tcttcttctt tgagtgactt ttcttcttca agctattctt  43020
tatttggaaa tattgattat ttaattaatg aaacaataaa aatttcaatt ggtggaagat  43080
gggagaattt taaatctaat tattttgatt cttatgacga atcattttca ccatcaaata  43140
aaatgtctgg tggtaagttg tcactagtta aaactcttaa taataattct aatatttatt  43200
ttaatattgc taagggctat aaccagggtg gatttaattt aggtcttggt cttgataaaa  43260
attcatcaaa tagaaattta tattatgatc cagaattttt aactaattac gaagttggaa  43320
ttaatagtaa atttttccag tcaaaattaa atcttggagc agtcctgttt tattctgatc  43380
gaaaagatca acaggtctta atttcaaccc aggttgatcc ttcagatccc aacacttttt  43440
tatacttaac ccaaaatgct gcagaaggaa ttaataatgg cttagagtta aatatagatt  43500
atgcactgaa taaatctcta ggtatatttg ctaattttgg attgctaaat acagaaataa  43560
aaaattggat ttcaagacca gatatagaag gtagagaaca ggcgcatgct ccaaaaaata  43620
gtttttcaat aggcatcaat tggaagccaa caaaccaatc ttatttatca ttgaatgttg  43680
ttggtaaaag tgagttctat tactctgatt cccataacaa tacttctgag tcatacaact  43740
taacaaacat taattatgga tatgaacatg gacaatggac ttattcatta tgggcaagaa  43800
atatttttga taagtactat tcagtaagag gtttttactt tggtaacgag gcacctgatt  43860
ttatagatac gctctacaga agacatggag atccaaggca tataggagtc atggtccaat  43920
atgatttcta actttataag tgaattttgg atggaaatag cagctgttgt atttgctatt  43980
atttatttat tacttgctgt aaaacaagac gtaaagtgtt ggtttgcggc tataattagc  44040
tcaatattat atttctttat tatgtatgac gcaggcttat atatggaagc ttacctgcaa  44100
attttttata tcatgatggc cttttatggg cttcaacagt ggagaagtgt cgatactgat  44160
gctcctcaat ttattgttag aacatgggat aaaaggatgc atattaagat cattacatta  44220
atagttatca tgactttaat ctctggattt ttattagaaa aatataccaa tgctatcttg  44280
cctttcatag atggactaac aacatgggga gcaatagttg cgacatatat ggttgccaaa  44340
agacttcttg aaaattggat atattggttt gttatagatt ttatttctat ctttttattc  44400
atgtccagag gacttttatt aacctcagga ttattcttta tttatcttgt aataatatat  44460
tttggttaca tgtcatgggt aaaaataaga gacgatatta gtgcagaatc ttcataacaa  44520
tctagatata aaaaatcata atctagagat tattaaaaca attaaatcag gccctgtatc  44580
tgaaatatct atttgtaatt ttgataacat caaagcaatc ttaagagttg atcatccatg  44640
cgcacacaaa ataaatgtag atcgagaaaa tgaaattttt atactcagcc aactaaaaat  44700
tttagatttt agtccagagg ttttatttag tgatttgtct tatggaattt tagtatggag  44760
atatatcgag ggtattgaat tttcacttgg taaggattcc aatgaagttt ttttaaaaac  44820
```

-continued

```
acttggaacc gaattaaaaa aaattcatga tattgatctc cccaaaagta agaaaaaata  44880
ttttagcaat gacataaatt tttacagaaa tttactaaag gaggttcctg aaaatataat  44940
tcttcataga ggatttgatt tatacgacaa actcaataac tctgataatt atgttctctc  45000
tcataatgac ttgaataaga caaaccttct ttggagggat aggttatttt ttttagactg  45060
ggagtactcg agttttaaca atcctttttt tgatattgcc tcgttatcga atgcttataa  45120
cttatcaaaa gttgataggg caattttatg gaaagcttat acaaataatg aatattcagt  45180
attaaatgat acaaatctta gagaatggat gcatttttgt cattatttag agtacatgtg  45240
gagtatttcg ctcatacaaa atggaaaaat tgatcagaac accctaaatt taaaaaaatt  45300
agagaaaaaa ttaaaaaata ttatttaaac aacaagtatt gcgcattctt tagttgttgt  45360
tttactatta tgtaagaaat ttacatttaa atgggggttt gatatgaaaa ttttatgtgt  45420
cttatatgat gatccaaaaa caggtatgcc agaaaggtat gcaagagatg atttaccaaa  45480
gttagataag tatcctgatg gaatgacact tccatcccca aaatctatag attttactcc  45540
tggtgagtta cttggttgtg tatctggaga actagggctt cgaaagtttc ttgaagatgc  45600
tggccataca ctagttgtta cttctgataa ggatggagat ggatgtgagg ctgataaaga  45660
attagtagat gctgatattg ttatatcaca acctttcttc ccatattatt taacaagaga  45720
caagatgaaa acagcgccta atttaaaaat ggcaattaca gctggcattg ggtctgatca  45780
tgttgatctt caggcagcca tggataatag cgtggatgtt gttgaagtta cttactgtaa  45840
ttctcgttca gtcgccgaac acattgtgat gatgatccta tcgatggttc gtgattatca  45900
tacccaacat agaattgtaa aagagggagg atggaatata gctgatgctg tacaaaggtc  45960
atatgatgta gagggcatgc atgttggtac tgtagctgca ggtagaattg gtattgatat  46020
gctaagaaaa atgaaaccct ttgatgtgca tttgcattac tttgatattc ataaactctc  46080
tgatgaaata gaagcagaac taaacctcac ctatcatgat tctgtagagt cattagttgc  46140
tgtgtgtgat gtagttaata ttagttgccc attgcatcct aaaactgagc acttattcga  46200
tgatgaaatg attagtaaaa tgaaaagagg tgcatatatc atcaatactg ctcgtggcaa  46260
gatttgtgat aaagatgcta ttgcaagagg cttagagtca ggccagctaa gtggttatgc  46320
tggtgatgtt tggttcccac aaccagctcc aaatgatcac gtatggagaa caatgcctaa  46380
ccacggcatg actcctcata cttcaggtac ttcgctatct gctcaaacaa gatatgccgc  46440
tggggttaga gaaattctag aatgttattt tgcaggcgaa ccaattagag acccatattt  46500
gattgttcaa aatggtgatc ttgcaggtat gggtgcgcac tcgtacacaa agggtacagc  46560
cacagatggc tcagaagagg ccgctaagta taaaaaataa gttttagaac ttacttagcc  46620
tttccttaat aatagagtct gcctctgcca taatgctatg cattaattct tccactgtcg  46680
ggatgtcatt aaccagtcca gcaaccattc cacatgacca ggctccaacc tccatagttc  46740
cttcatgcat aatttttgga tagactcctg caacctcatc cacaatatca gcaaaagtta  46800
attcatcacc aagagctttt tctttttcaa tcaatctctc aacagcttca ttattaagaa  46860
ccctttctgt atttgttaat gatctcatga tgagtctagt atctaactca gaagcattta  46920
cgatagcctc tttcacattt tgatgaacag gtgcatcttg agtagcaata aacctagttc  46980
ccatattcat tccctcagca cctagtgaca tggcagcaac caaacttctt ccatctgcca  47040
ttccacccga ggcaacaaat ggtatttcaa gctcatctgc tgctctaggt aagagtatga  47100
aattaggaat gtcatcttct cctgggtgtc cgccacactc aaaaccatct acagaaaccg  47160
catcgcaacc tattgcttgt gcttttaatg agtgccttac agaggtgcat ttatgaataa  47220
```

-continued

```
cttttattcc tgcttctttt aaagctggga ggtattctgc aggatttctt ccagcagtct  47280
ctacaacagg aacccctgca tcaataatta cttttatcaa accaggatag tctgggggtg  47340
ttagtgatgg taaaaatgtt aaattaacag caaatggctt attggtcatt tctttgcatc  47400
tggcaatttc atttgctaat ttctcaggcg taccctgtgt tagaccagta attgttccaa  47460
gtccacccgc atttgatact gccgctgcaa gctcggcaaa accaacatgg tgcattccac  47520
cttgaatgat tggatgttct ataccaaata attcagttat tttagttttc ataatactct  47580
cctatttatc ttccattggg gttaaaaaat cttcatattg agtttgaagt ctttgcatgc  47640
cacttatcca tctatctctg tcattacctt ttcttttaac atattctaga acctcactat  47700
gaggggttac taaaaacctc tcctcctcta tggcgttaag aacatccttt gcaacaatat  47760
cagcttccat cattccatca actcctgcta caccaggacc atttgcagtc atagcagttc  47820
taactgcttg agggcataaa caggaaacgc cgataccttt atttccatat gtaattttta  47880
tccattcagc aaaactcaca gctgcagctt ttgtaactgc atatccagcc gcacctagtt  47940
gagttaaaag accggctgct gaggatgtat tcataagata gccttcacct tgttctatca  48000
tttgaggaag cacatgtttt gcagcatgaa tatgagactg aacatttaca ccccatatca  48060
tgtcccaatc cgaagtatct gcttcaaaaa atcctggctt tccaccgata cctgcatttg  48120
aacaaaatat atcaatacca ccagaaaatt cattagcctt ttgtataaca tttataatgt  48180
cgttttcttt ggaaacatca gcacttactg caagcccatt aacactcttg gctgtttcct  48240
ccgccccatt taaattcata tcaacacata ctatagaact tgccccagat gcatagaact  48300
cttcacataa agccttacca attccactgg cagcccctgt aaccacaact cttttattat  48360
taattttcat aaattgacca ctttttttaat tttttattta actttattgc ttagatagtt  48420
tattacaaaa caacaatact taatattgca aaatcgcata cccatcttta taaatttatt  48480
gctattatta gtgctagaaa atgaaatact gagatttaat atgaagaatg ttgttgttat  48540
tggctcgtcc ggggcaatag gaaaagcctt tattgatagc tatatcaaag atgatgatgt  48600
tgaaaatata ttttcatttt caagaacagg cctttccatt gaggataaaa aactccatag  48660
ttttttttatt gatattgagg atgaaactag tatttgtgat gccgcagaga agatagacaa  48720
gtcctcaata gatgaaatta tcgtcgcaag tggaatactt cataataaag attttgggcc  48780
agaaaaaagt attagagatt taaatgcaga taacctttta aaggtcatta aggttaatac  48840
tatcggccca acaattgttg gaaagtattt cattccattg ctaaataaaa aagaaaaaag  48900
cgtcttagca tttttaagtg caagagtcgg cagcatttct gataataaaa caggtggttg  48960
gtatgcctat agagcgagta aaactgcact taatcaaatc attaaaagtt ttagtattga  49020
attacgaaga accaatccaa atgccattat ttttggtcta cagccaggaa cagtagatag  49080
tgaattaagc gaacctttta aaagaaatgt aaaagaaggt aatttattta ctccagaata  49140
tagtgtattg cagctaaaaa atattattga tacagcaagt ccatctgatt caggcaaact  49200
aatttcttgg gatggggaag agattcagcc atagttggtt atgaatatat tttcatatta  49260
gaataaattt ttaggggaaa aaatgagtat taaatattat gactggtcta aatttcaggc  49320
caacactagg ccaaataaag ttgccataag agagctagat aataacaaga tctatactta  49380
cggagaattg gataaaagat catcaaggct tgcatcacat ctccaaagtt caggaataaa  49440
aaaaggagat cgtattgcga tactatcgct aaattgttca gaattttttg agctagaatt  49500
tgcttgcgga aagattgggg caatagagat accattaaat tggagattaa caaaacccga  49560
```

-continued

```
gctcagttat attcttaatg atagtgagcc aaaaactcta atttatgaca atcagtttga  49620
agaaatggtg aaagagctaa aagaagaatg taatatttct gaaatcatag ctcttgatca  49680
atttgaccaa gaaagtgatt atgaaaaagt tttgagtaat gcttcaggca tttattatca  49740
ggaagaagtt gatctagaag ataacattat gattatgtat acctctggaa caaccggtca  49800
ccctaagggc gccatgatca cgcacaaaat gcagcttttt aatgttatta atttaggtat  49860
ttcagcagct gtttcccctg aatcagtcca tttagttgtc cttcctttat ttcatacagg  49920
cggaatgaat tgttattcaa atccaattct tcatgcaggt ggcgagttaa tattacttaa  49980
agagtttgag cctgggaaag ttctatcaat tatcggcagc tctgactatg gagttactca  50040
tctgtttgca gttccagccc cttatcaatt tatgatgaat catccagatt ttgaatcaac  50100
aaatttatca ggagttaagt atgctggagt tgggggcgca ccttgtgcag aggctatttt  50160
gaagacttat ataagcaagg gtgtttcgat gcagcaagga tggggtatga cagaaactag  50220
tccaggtgct actggtcttg aatcgtccga ggctgaaaga aaaataggat ctgctggaaa  50280
accgcttctt catactgagg tcaaggtggt tggagatgat gggaatgaac tgcctgctgg  50340
agaagtaggc gagatttata ttaaaggccc aaatattaca cctggctatt ggaagaaaga  50400
agaggctact agagattctt ttgaagacgg gtggttaaaa acaggtgatg ctgcttactt  50460
tgatgacgag ggtttttat acatagttga tcgatggaag gatatgtata tctcaggtgg  50520
agaaaatgtt tatccagctg aagttsaaaa tgttatctat cagttaccac aaatcgcaga  50580
agttggagtt attggtattg atagccctaa gtggggtgag actggtaaag cctttgttgc  50640
tttaaagccc gatcatgaat tgacggcaga agaagtcata gatcattgtt taaaaaatct  50700
agcaaagtac aaaattccag agaaagttga gtttattgca gctcttccaa gaaatgctac  50760
aggtaaagtt ttaaaaagaa cattaagaga tatgtaatat ttttaagcca aaaaaaaccc  50820
agcctaagct gggtttttta tttaactatt taaagttatc taatgttaag cattagaaga  50880
ttctttaaca gcaacattcc atataattaa accaaataga atcttgttaa caaagtcagc  50940
aaggttatag ataaggttta agttaagagc tgatccaccg tcacccatca ggtaacctgt  51000
gaaataacct acaggataaa tcgcccaacc aaagatgata atatacatca ttgtgttgta  51060
agctgattgc acagcaggac ttgcagtatt acatgcagat tttccttctc cagcccataa  51120
ttcataaatc atgtataccc aagctaaaca cccaataatg aatgcaggcc atgcagccat  51180
gattcctgct tcacccatgt aaccaaacac aagcataaca agagaaccaa ctagtaattt  51240
cttaaataat gatccagcaa cattagttgc agcagcaaga attaagtaga attcacatat  51300
taatagagga actgttagta accaatcaat gtatctaaat acagttggcg aatcaccagt  51360
ttcaatccat acccctctca tgtacatgta atgccagaaa gcaataccag taacaagacc  51420
agatacagtt aatgatgttt tccattttgc agaaactcta tctctttcaa caaagaaaaa  51480
tacagtagat gctaataaag cagcagtaac taaccaaaaa gaaacaccag tgtaatcact  51540
agcatcaagg tcaccaccac ctgcagcaaa tgtaggaagt gcaataacac tacctaatat  51600
cagtaataat ttcatatata actcctatat taatgacaaa gaagcataat tgcctccccc  51660
ctaattaaat atgaaattta atagtaacca atattaatag aggttacaaa taaaaagcat  51720
ctattttttt aatagaaaat atgtgtaata aaacaccata ctttaaatta atatttattt  51780
tgcataagta gacttgttta gtatcatatt taacatgaaa gttgcaattt atcctggttc  51840
ctttgacccc atcacaaatg gtcacacgga tattattgat aggggttgcg gactctttga  51900
caaggttgtt gttgcaatag ctaagagtga atcgaaaaac cctcttttta gcctagagga  51960
```

-continued tagaattaat ttagcccaat ctatttttaa aggaaatgaa aaagtagagg ttgttggttt 52020
tccaagaaag ttaacagttg atcttgcaaa agactatgga gcttgtgcaa ttataagagg 52080
cctacgagca gtttctgatt ttgaatatga atttcagtta gcaacaatga ataggtcgct 52140
ggctcccaat attgaaagca tttttttaac accaaaagaa agtctcattt atgtatcttc 52200
tagcttaatt aaagaaatat cagacttaaa aggcgatata tcgaagtttg ttcatcctat 52260
agtagagcag gcacttcgag cgagtagaca cttagctctg acaagcttca caaaaaaaag 52320
tagctctttg attgacgatc gttttacaaa tagtgccttt gcatttattg cagggctcgc 52380
cttctcttcc atatacattt aatttaaatt taaaatatcc tggactacca tcagctgagt 52440
agaagtcttt taatgtagtt cctccaacct ctattgcttg ctctagtatc ttttttccag 52500
cagctactaa tcttttacaa gcatctaaat ctaactcatt ggcatttttt agcggatgaa 52560
ttttagctaa gaaaaggctt tcagacgcat aaatattgcc gataccgact acattttttt 52620
gattcattaa atagctttta atatttgttt tagagtgact gcatcctgaa aaaaaatcct 52680
ttgcattaaa atttttagaa agaggttcag gcccaaggtt ttttattaac ttatgtttat 52740
cgatatcaga agtaagatgc attgatccaa accttctggg atcattataa ataattcttt 52800
cctcatcaaa aattaattca atatgatcat gtttgataaa gaagttttca ttattttttg 52860
caattctaag actcccagac attcctaaat gaagaataat ttttttatca ttagatagtt 52920
taaaaattat atattttgct cttctttcta agctttcgac aacttgatct tttactgagg 52980
tttcaaagct atccaccact ttccatctaa ggtttctgtt gtgtatcctt gcttctttca 53040
gcaaagagcc tttaaatttt ttaattgctc tcagggttgt ttcaacctct ggaagttcag 53100
gcatttttaa ctgagtaaat tattaatttt tactatgtca gctggagtaa ttgttcccga 53160
tgcgagccct agtcttagat tggcaagtat gtaatcatat tttgcattag caagattttt 53220
ttccgcgctg tataagtttt tttctgcctg caagagatca acaacgtttc ttgttccaac 53280
tctgtagcca acttgagtcg cttccagggc actagtggcc gaaatcactg cttgtttttg 53340
agcatttaca tttgcaacta atgttaaaac atttgaaaac tgggatctga cttcttgaat 53400
aatccttctt tctgtaaata gagtattttc atttgctctt tcatactgtg aatatgcttg 53460
cttccttctt gagttaacgg cgccgccttg aaagagtggc atacttagct gaattgcata 53520
attccttctt cctgttactg atggaactgg aataccttgg ccattgatat taaaaccttc 53580
atagttaaat tggtttgttt cagattctga ctgacttcca acaatgtcta tcttaggtaa 53640
atgatttgaa gctacacttc ttgcactgct tttcgctgct ttctttctca aatatgctgc 53700
ttttaactgg tagttatttt ccaatgctaa ttcaacccat gtctcttttg aacttggtgt 53760
tggcaggtca ataagcaaac catctcccaa ttcatttaag ctgaatattt ctctaccaat 53820
cagagcattt aaagactctc ttgcagaata aagtgatcct tctgttctaa ttcttgaggc 53880
tttacttaga tcaaatgcca attgagcctc ttgaactcca gttatggctg ataacccaac 53940
atcgaatctt tgttttgctt gatcaagttg ttttttaata gctttttctt cagatattgc 54000
tgcatttaga ttatcaatag ctctaagtac gccaaaataa agctcagcag ttcttactaa 54060
aagattttgc tgctcaaatg caaagtctgc ttcagcagca tctgtaagag atttagattg 54120
cctatattga aaccatgtat ctagtctaaa gagcggctga gtaaccctgg cagatgtaga 54180
aaaagagtta tattgctgct gcagttcttt gttttgatag tattcgttcc agttagttga 54240
tccactcaag gtaatactcg ggagaagcgc agctcttcct tgaaccttaa gctctttatc 54300

-continued

```
tgctaaatat gaatattccg ctgctttata tgtagggtca ttctcaagcg cttcattata  54360
gatatccaaa agactttcag atgaaatatt aaatgagata aaaagtgcta aaaatgattt  54420
tgtgtaaatt ttcataactt attttaacct attaataatg tttgcagtgc aaacatttat  54480
tttttttaat tttattgaat ttattttata tttcttagag tagaatatct ctaacaagtt  54540
caataatttt ttataataaa aaggctttaa aaattggcta aaaattcata tgacgctcag  54600
gcaattgaag tcttatctgg actagatcct gtcaaaaaaa gacctgggat gtatacggat  54660
acatctaacc caaatcattt aattcaagaa gttcttgata attcggttga tgaagctctt  54720
tcaggttatt gttcaaacat aaaagtatct gttctaaaag atggctttat taaggtctct  54780
gatgatggaa ggggtatgcc aattgatgag cacccggaac ataaagtttc aggtgttgag  54840
ctcatccttt gtaaacttca tgctggagcg aaattctctg gagatgatta taatttctct  54900
ggtggccttc atggtgttgg agtttctgtt gtaaatgccc tatctgatga attagaggtt  54960
agagtaaaaa gagattctaa agaataccaa atcactttta ataatggaga taagtcttct  55020
gaattaaagc caattgggga agtggggctc agaaattctg ggacatcaat taaattcaaa  55080
ccaaatccta catattttga aactatagag attcagataa aacagcttaa gcatttatta  55140
aaggccaaag cagttctctg tcctggatta acgatagagt tcgttaatga aaaaaagact  55200
gatgataaac aaaagtggta ttttgaagat gggctcaaaa gctatttgat tgattcttcc  55260
gagggagcag acttggtttt gctagattca attgtatgct ctaaaaaatc tcaagctcaa  55320
gagcttgaat ttgcaatcaa ttggtcatta agacccccaa aaaataaact cgatgaaacc  55380
tatgtgaatc tcataccaac tgctcagggt ggctcacatt taaatggctt taaggctggg  55440
cttttagatt cattaaaaga attttgtgaa tacagaaatc tattgcctaa aggtttaaaa  55500
attaatgcag atgatgttct taataatgca atttttataa tttcatctaa gcttcagaat  55560
cctcaatttg cagggcaaac caaggaaaga ctagattcaa aagatcacat gtcgttcgtc  55620
tcaagtacca caaaagacat tttaagtatt tggcttaaca ctcatacaga agagggcgaa  55680
agaatagcag aacttgcaat tatgtctgct cagacgagag caaaagtttc caatatagtt  55740
gaaagaaaga aaacttttag aggcccagcc ttacctggaa aactttcgga ctgtaatagt  55800
caggacttaa atgaaacaga gctttttttta gttgaggggg actcagccgg agggtccgca  55860
aaacaagcaa gagaaagatc tttccaggca atcatgcctt tgagagggaa gattttaaat  55920
acttgggact tagaaagtgc agaaataata aaatctcagg agataaaaaa cctatcaact  55980
gcaattgggg ttctgccagg aaataatgac ctttcatcac taagatacgg aaaaatttgt  56040
attcttgcag atgctgattc agatggtctg catattgcaa ctttactttg tgcattgttt  56100
ctaaggcatt ataaatcttt agttcaagag ggaaggatat atatttcaat gcctcctcta  56160
tatagaatcg attctggtaa agatgttcta tatgcacttg atgataaaca gcgagatgaa  56220
atagttactg aatttaaaaa gaagaagggc aagcctaaag taaacattca aaggtttaaa  56280
ggacttggtg aaatgaatcc acctcaacta agagagactg tgatggaccc tgctactcgt  56340
cagcttgttc agctttctat cagctcaagc gataatgcaa attctatgat ggacttactt  56400
ttgtccaaaa agaacgcacc agcaagaaaa gaatggcttg aaaagaaagg gtctctagca  56460
aaaatataaa tatgaaagaa caaataacct caattagcct caagcaatat gctgaagagt  56520
cttatcttaa ctatgcaatg tatgtcattt tagatagagc tttgcctaat attggagatg  56580
gccttaagcc tgttcaaaga agaatactct atgcaatgtc agagcttggg cttgatgctg  56640
gctcaaagta caaaaaatca gcaagaactg ttggagatgt tataggaaaa tttcatcccc  56700
```

-continued atggagacgg cgctgcatat gaagctatgg ttttaatggc tcaaaatttc tcattcaaat 56760
acccttttgt agatggtcaa ggtaactggg gttctcagga tgatccaaaa tcttttgctg 56820
caatgaggta tacagaatct aagttaacta aatttgcaaa tcttttaatc tctgaattga 56880
agtctggaac agtcgattgg cagcctaatt ttgatggctc tcttttagag ccagtaattt 56940
ttccagccaa actcccatct attttattga atggcacttc tggaattgct gtaggaatgg 57000
caacagatat tccatctcat aatattaatg aaattattga tgccacagta catcttattg 57060
ataatccaaa atcacagttg gttgatttac tcaagataat taatggtcct gatttctcaa 57120
ataattcgcc aataattgct agcaaagatg agctgaatga aatttattcg actggaaaag 57180
gcggcttcaa agctcaagcc caatgggcgc aggataagaa tcaaatcatt atcaacgcat 57240
taccttatca agcatctggg tctaaaattt tagagcaaat agctgatcaa atgcttaaga 57300
aaaaaattcc aatggtggtt gatcttactg atgaaggaga ccacaaggag ccagtaaggc 57360
ttgtcataac tttaaaatcg aacagagtaa atgctgaaga tgtaatgaat cacctttttg 57420
catcaactga tttacaaaaa aattatagag taaatatgaa tttgatttca ttgaaaggtg 57480
gaccaaaagt tttctcccta gttgatttat tgaaagaatg gctagtcttt agaaaagaaa 57540
ctgtaataag aaaactagaa catagactcg accaggtaaa cgataggctg catatccttg 57600
aggggttatt aattgtttat ttagatttag ataaagtaat aaagattatt agagaatcag 57660
atgagccaaa aaaagatatt attacagctt ttaaactttc tgatatccag gcaaatgcaa 57720
tccttgagat taggttaagg caactagcca agctagaaca aatcaagtta gaacaagaaa 57780
gagatacttt ggtagcagaa caaacagata ttgaaaaaat actaagctct aagacaagac 57840
ttaaaacatt aattaaaaat gagcttattg aaataaaaga tgagtttgga gaagtaagam 57900
aatctccaat aagagaagca acagaagcca aagttttttc tgaagaagaa actcttgtca 57960
ctgagcctat tacagtagtc ttgtctgcag ctggctggat cagaagtgca aaaggccatg 58020
agatagaccc cagctcactt tcctatagag gagaagatgt acttcaagat tatggaagag 58080
gaaagagcaa tcaagtttca gtttttcttg actcaaatgg gaaggcttac tcacttgcaa 58140
gtcactctct tccatctgct agaggaatgg gtgatcctat tacaggaagg gtatctgcag 58200
attctggagt aaagttcatt tcttcattga ttgggaatga tgaagataaa ttcatgatta 58260
tgaatactgc tggatatggc tatatttcag agtttaaaaa tatggtttct aataagaaat 58320
caggaaaagc atttatgaaa atccctcatg aagcagacct tcttaaagcc attaaagtaa 58380
gagacgatca tttgtatata gcagcagttt caaatattgg cagactttta atttttaaga 58440
ttgatgaatt gccaactctt ggaaagggca aagggaataa aataataaat ataccaaccg 58500
ctaaatttat agcaaaagaa gagttaatga cccatgcgca acttgtttct gaggctagct 58560
ctttaaggat tgaaagcgga aagagattcc tcactttaaa actcaaagat ctagaaaact 58620
atatttctac aagagcaaaa aggggaaata tgcttccaca aggatatagg aaggtagata 58680
aaatgattga agaggttgag ttagaagtta aagaagactg attatagatt tctcaaaaat 58740
ttttaatccc tcatcaacta gctcattttc tattattagg cttggagaaa acctaacagt 58800
agatgcattc gccttaagaa tcattaaccc attatgatgg gattttttta ttaaatcatc 58860
tatttgaatt ttgctatcct tgcttacttc cactccgacc cataaaccag cagaagttat 58920
tttttcaaaa catttgtgct tctcatttat tttattcaac aaattgataa atctaacttc 58980
tttctttaaa accttattta aaaatgattt tttagaaatg gtatctataa cttcattacc 59040

-continued

```
tatggcacat gcaattgggc ctcctccaaa agtcgtgcca tgagaccctg ccgacatatg  59100
ttttgaaact ttatctgaag taagaatgcc tcctagtggg aagccattag atataccttt  59160
agcaaaacaa agaatatcag gagtaatgtt aaattgctca taagcaaaga gtgttccagt  59220
cctgccaatc ccggattgaa cttcatcaat tatgacaagt gccttatgtt tttttgcaag  59280
tttctttatt tttgctataa atttttttatc tgcttttgtt attccagatt gccattgaac  59340
cagttctaat ataaccgctg cagtcttatc tgaaaaaacc ttttctagat tagtaatgtc  59400
attatatgga tgattttta tccctctagg cagaggcgca aaaccgtctg taagatgctt  59460
agctttagct aaagctatac caagcatagt tcttccatga aatgacgttg aaaatgaaat  59520
gacctcattt ttatttttat taactgttga tgagcaaaat tttcttgcta tcttaactgc  59580
agcctcaatt gattctgccc ctgaattgca aaaaaatact ttatctgcaa aagaattctt  59640
gcataacttt cttgccaaag taactgaggg ctcatttatg tagagatttg ataaatgcca  59700
aagctcctca gattgctttt taagaatttt tattagatct ttatttgaat gaccaaggtt  59760
agtgacggca atgcctgctg tgaaatcaat atatttctta ttatttaggt cccatacatg  59820
cgatccactc gcttttttta caacaaaatc tgcaggagcg taaaaaggca ccatataatt  59880
agtatattct ttaattatct ctttcataaa tatattgtat cgtggtttca gttcaaaaat  59940
taaatgacca aaaatttcta gtatctttaa aaccaaacag ctcactcatt ggctttaata  60000
gaataatatt tatatctagt atatctattg tatgcggtgg catagcattg atatttttct  60060
tttttggagc aacgctcatt ttgccttttg ctggtttaga gcttggtatt ctattcactg  60120
cattctattt aagttttaaa tggagtgata aaaaagaaaa aatatttatt tctcaagatc  60180
ttgtaactat agaaaaaggc tctaattatg ctgaatataa atgggaagag ttcaggtcat  60240
ttacctcttt ccaggtttca aaagacagaa gagatcttct taagctaagc tttaggtcta  60300
aaggcgagga tgttgaggtt ggcagctttc taaatgaaga tgataaaaat gtattaatag  60360
aagagctaac tcagatcata gatacattaa atcacgattc cttctcaaag ccagagcttt  60420
aatttctttt taacttcttt tagctttaat tcttttattt cagggatgcc atttctaaaa  60480
tttggaaatg attctccctg tattaatggc ataagatatg caattgcttt tggggtaacg  60540
tccattccat ttttagctat aaaagatttt ggtaattttt tttctaaatt agctattttt  60600
gccagtggag ctggttcaat tttccaccta tattttttag ctttacctct aactattatg  60660
ggcataacac cattcatgcc ttctactgca tactgaactg ccttggcccc aacagccata  60720
gcttgctcta ggtctgtttt ggaggcaata tgtcgtgcac ttctttgtag atagtcagaa  60780
acagcccaat gatttttttag ttttaattta tcagtaatta agttggcaat gtaaggcgca  60840
actccaccaa gttgagcatg accaaatgca tctattgttg ctgattcaga aagaaatctg  60900
ttcttattat ttttcaaccc ttcggatacc acaacaacac agtagccatt ttttttaaca  60960
acacttttaa cttctgctag aaattttttt tgattgaagg ttatttcagg taataaaatt  61020
atatgaggtg catctccttt ttcttttctt gcaagagaag atgcagccgc catccagcca  61080
gcatgcctgc ccataacttc taatataaaa acttttgttg atgttgctgc cattgaccga  61140
acatctaatg aggcttctag agttgatgtt gctatatatt tagccgccga cccaaatcca  61200
ggacaacagt ctgttaatac caaatcgtta tcaacagttt ttgggatggc tatacagtta  61260
attggataat ttaatttttt acttatctgc gaaactttaa atgcagtatc agctgaatca  61320
ttaccgccat tgtaaaaaaa atatcctata ttgtgcgctt taaaaacatc aataagcctt  61380
ttgtactctc tttcgcttga ctcaagatct tttaacttaa acctacatga cccaaaagcc  61440
```

-continued

```
ccaccaggcc tatatttcaa tgactctaat gcagatattg attcttttga tgtatctatt  61500
agttcctcat tcagcgcgcc caatattcca ttcttgcctg cataaatttt accgatgtct  61560
ttatgcttct tggcctctaa aatcagagcg ccagctgtag catttataac tgcggtaacg  61620
ccgccggatt gagcataaaa cgcatttttt ttcatttttt ctccatcaaa tgtactgaaa  61680
taaaaatatg taaagtatta taactaatat gcgaatacat atcttaggga tctgtggrac  61740
ctttatgggc ggccttgcta agatacttaa agagtcaggg catgaaatat ctggatcaga  61800
tattcaattt tatcctccca tgtcagacta tcttgatagc tttgatattg aaatgatcaa  61860
gggctatgac ataaaaagca tgccagatgc tgacttgtat gtgattggta atgcactttc  61920
tagaggaaat gaatccgttg agcatatttt gtccaattct cttccgttta agtcaggccc  61980
tgaaatgctt ggagaaattt taaaaaataa aaaggtttta gctatatctg gaacacatgg  62040
taaaacaacg acttcatata tgttgactca tattatgtta gatcagggta gggatgtcgg  62100
ttttctagtt ggtggaatat caaataatat atctggctct gcatgtcttg ggtcagatgg  62160
aacttttgtg attgaggcag atgaatatga ttctgcattt tttgataaaa gatcaaaatt  62220
tattcactat tcaccaagca ctatagtcat caataatatc gaatttgatc atgctgatat  62280
ttttaataat ttagatgaca ttaaaagaca attccatcat ctaattaaaa taattccatc  62340
aaatggaaat gttgtttatt ttgctgatga taaaaatata agagatctta tcgatatggg  62400
aatttggtca aatcagatag caatcaataa taatgctcat tcaattgagg cagtttattc  62460
tgataagact ctaaaatatg aagaaagtat ttattcatta aatgagttac ctttaatagg  62520
agaacataat tttaaaaact acatttcggc tattttggcg gcaaagacag atggaattca  62580
aattcaggat tctatcaaat cattagctag ctttgatggc gtaaaaagaa gattagaata  62640
taaaggaagt tttgatggca tagaaattta tgatgatttt gctcatcatc caaccgcaat  62700
agaattttct tctaatgccc tcgtaacaca aaatccatca aaaaaaatac ttggtctcat  62760
tgagctaggc tcaaacacta tgtctggggg ttctcatggc ttgtctttgg ttgaatctgc  62820
aaaatcttta actcatgtta tctggctaga tcgcaataat gttttgtcag agaatgctag  62880
cattgaatct actaacacta ctgaagattt tatttctgca gcgatatctg ctttctcaga  62940
ttatgatatt gttattttga tgaccaataa agacagccaa aaaatattaa aacccattgt  63000
agatcacttt gaaaaataat aatttaccag tttttccttt aggaatagtc gccctcccag  63060
gtagcatcca atctcttcaa atttttgagc ctaggtatat acagatggtt aaaacatgtc  63120
tatccaagaa ccatggattt gtaattgttt ttaatgccaa taatgagtct caaggcgatt  63180
tcactttttc taagaaggga agttttgttg aaattataga ctttaataat ttgccaaatg  63240
gccttcttgg gataactgta aaatctataa ataaggtgat aatcagtaat atatgtcaat  63300
tagaagatgg actgcatatt gctgatatta aggcacagat agatccagag gtagatgatc  63360
aagctgtttt ggcagaatat cctgagatat ctagcattct ttctcagctt gtaaagcatc  63420
ctaagattag tgacctgccc atccaggttg actttggctc tgctgattca gttgcatacc  63480
acttagcagg ccttatacct ctaagctcaa atgagaaaca aaaactatta gaagcattcg  63540
atgcagcaca gcggatgaga attctttcag actatattga aagaatatct actacataaa  63600
ttatttattt taatattatt ggcggcttat tagattttgc tctaagccaa ttgatggact  63660
taaaaaccgt agggatttct acaaaccttt tttcaatata gtatttgcct ggatagttac  63720
taagcattag cccaataata atagtgaaca aacctggcca ggtaacacca gcatcatgat  63780
```

-continued

```
tcccccaata ataagggaat aacctaaaat atttttaatc agtaaaacta aataccacaa  63840
caacgggtta ttggtcttaa atttcgagac atctttcttt ataaaatagt cacttggaat  63900
taatccagca agccacctca tactaacgag actaaataaa aaaataaata aagatattga  63960
gctcagccaa agtataagaa ctttataaga ttcaaaaaaa attatgatgg catttagggt  64020
attaaattcc ataattaccc accttttat ttaataatga tttagtatag caatgtctaa  64080
aaataaattt aaacattaaa taaatataca ataattttgc caaaaaaagc cttaaatgat  64140
atttgcactg aaaccctcag tgataataaa gccgaaaatg ttctatcact tgatatcaaa  64200
ggtatttctt cttttgctga caacatcatt attgcaactg caaattcgaa taggcatgca  64260
aagtctttat ccgaaaagtt agttgaggag ataaaagcta ataaaattag tatcatgggt  64320
gtagagggca agacagaatc aggttggata ttagtagact gtggtgaggt tgtagtaaat  64380
attatgaaga atgacataag agagttttat gatttagaag gtctttgggg tgaaaacacc  64440
ctcatcgatt cttcgaaata aatgctatta aatatcataa gtgttggaaa ctcaccttca  64500
tcttgggagt taacaggaat agaatattac acaaagcaaa tccctaaaga agtaagtcta  64560
aattttatta acgtaaaagg gcagcaacac ccaaaaagat ctacagaaga ggtcttaaaa  64620
cttgaatcta agttaatctc gtccaaaata gattctaatg gatatattgt ttgctgggac  64680
tcaagtggcg agtcgttgaa taattttgaa tttagtaaat tttttgaaaa atccatgctg  64740
gaaaatatga agctttactt tgtaattggt ggttcatttg gcatacctcg agatattctt  64800
gataaatcta ataagataat ctcgatctca agtctcaccc tacctcacag gcttttcaag  64860
attgttctta tagagcaaat ctataggtca ttttcaattc tcaaaaatct tccctaccac  64920
aaatgattga tctgaatgag aggtttgttg aaaaaagaag ctttttcaat agattgttgc  64980
ttatatattt tttctttggg gccctgtttt tattcttgct tttcaagacc tattctttac  65040
aggtttctag ctattctgac tatgaactag cagcactaaa gaataaaaca aaagaagtgc  65100
tagttcagcc tgttcgagga gtcatctatg acaggaatgg aaatattcta gttaataatg  65160
tccctacata tgacctaata atccaaccat caaaaattaa aaacttagat gatttcatta  65220
ttaatatttc taaaataata gagctatcag attcagaaat tgaaaacatt attaaaaatt  65280
ttaaaaggag tgcaacttat aatagagagc taacaattaa aaaagatctc tcgaaagaag  65340
aaatagcaaa atttgaagta agaagctacc aatttcagaa tgcatttata gatgttaggt  65400
atagtagaga aaataaatat ccttacttat tttcacacgc actcggttat gtaggtggtg  65460
taagtaatga taaggtttta tcaattttaa aaaatcaaga tttgaagcaa tctgaaacaa  65520
cttttaagta ttcaggtggt tttattgctg gaaaaacagg attggaaaat atttatgatt  65580
cagctttaag agggtccttt ggaaaaaagt tatttgaagt tgatgcaagg ggaaggcttt  65640
taaaagagct aagttttgaa aaacctatta atggaaaaag cctttttact catttagatt  65700
taaattcaca aaaaaaagcc tttgaacaaa tgaataatag aaggggtgct gttgttgcct  65760
tagagcttaa atctggttct atagttacct acctaagcac tccaagcttt aatgtaaatg  65820
gtctttctaa tggcatgtcg tcggtagagt tcgaaaaact gattaatgat gtagacaagc  65880
catttttga tagggccggt caaggtcggt actctccagc ttctacaata aagccagcaa  65940
tagcattgtt tggtattaaa gaaaaaatag tagactggaa ctttacactt aaagatcctg  66000
gatttttgt attaccagag gatcagagga tttatagggg atggaagaaa ggaggtcatg  66060
gaacaattga tatgaagggt gcaatcatag aaagttctaa tactttttc ttttctcttg  66120
cttataaggc tgatattaat aatttaatca gccatctttc tgagtttggt tttggcagga  66180
```

-continued

```
atgtttgtaa agattgtttt aatccagatt ctggattatt gcctacgcct gaatggaaaa  66240
tgaataatct taattttggc tggtttaaag gagataccgt taatttaggt gttggtcagg  66300
gctatatgag tgccactcca gttcaattag catattactc tgcatttctg gcaaaaaaag  66360
gaaatcttca agagctatca tttgtcgaga gtgacagcct aagcaatact gcttttataa  66420
ataatttaag catagataac tcagactggg atcaaattca ctcaagcatg attggagtta  66480
ttgaagatcc gagaggcact gctaaaagat taaaaccttt aaaatcatat gttgttgctg  66540
caaaatctgg aacggttgag cttgtcagca cacaaacaaa ggaagattac aaactagtaa  66600
ggcaaaatat tggtaacaga gaccatgcaa tcattgtggc ttttggtcca atgcctgatc  66660
cagagtatgc agtaagtgtt gttattgaaa atggtgaaag cggcggttct gttgcaggtc  66720
ctgttgctat tgctgtttta aatgagctta tcaataaatg aagaaaaaat tagactttaa  66780
aaactttagc atttattttg atcaatattt atttattgcg ataaccctgt tgtcggtcat  66840
gggtttattt tttttataca gcgcatcaca agaagatatc agcactgttg ctaagcaagc  66900
tgtattcgtt ggttttggtt tgctgttaat gtttgtagtt agccaacctg accctgattt  66960
ttataataca ttttctgggt tattttttgg ggggggastt gtattgattt ttctaactat  67020
gatttttggt aaagaaataa atggagccaa aagatggctt gatttaggat tttttaccct  67080
gcaatcctct gagattatta aaatatcatt gccaattttt ttatcatcat atttatataa  67140
taagccactt ccaataagca ctaggcatac ttttattaca ttgatattaa taggttttat  67200
atttgcactt gtagctagac aacctgactt gggaaccagt ttagtagtat ttatgtcagg  67260
gggttatgta ttatttttag caggattaag ccgccgttta ttggatctgc aatagcctta  67320
tttttattat ccttacctbt tttatggaat aactttctag agccatttca acaacagaga  67380
gttttaactt atttgaaccc agacgcagac ccttatggta ctgcatggaa tataactcaa  67440
tcaaaaatag caattggatc aggcggaatt aatggaaaag gttatcagga gggctcccaa  67500
gcccatcttg atdttttacc agagacagaa acagatttta tttttgctgt tattgctgaa  67560
gagtttggtt ttattggagt ctgtattttg ttatcagtat ttdtctttat atkactcaga  67620
tgtttatatt tagcatttaa tgcaagagat agattttgca ggttaactat aggaggccta  67680
agtttagttt ttgcctctac attatttatt aatttagcaa tggttgttgg tgtagttcct  67740
gtagttggta tgcctcttcc atttatcagc aaaggcggct catctttgct atcctkttat  67800
atagcttttg ggattataat ttctatggca acacataaaa aattaatgca aagatgaaaa  67860
aaattatatt tataacttta atattcacta tttcaattac tgcggattat tcgaatcatg  67920
aagatagcca aatggtaata aatgaactcg tcacaaaaca cggttttgag gaatcttatg  67980
ttactgcaat cttaaaaaat gcaaaaaagc gtgatgagat gcttaaatct gttgctaatc  68040
ctgctgaaaa aacaaaaaca tgggatgaat atagggctat ctttataaaa acaaaaagag  68100
tttcagaagg caaaaaattt ataaaaaaaa atattaatgc tttagagagg gctgagaaag  68160
aatttggagt tcctaaagaa ataattactg ctattttagg cgtagaaact aattatggca  68220
gcaataaagg tggatacaga gttttagata gtcttactac tttaggtttt gatgacccgc  68280
gaagatctaa ttttttaga agagaactta tagagttctt ccttttaaca agagaaaata  68340
atttagatat caaaacaaca aaaggctcat atgcgggagc catgggatat gcacaattta  68400
tttcgtcaag ctaccgagcc tatgctgtag attttgatga agatggttac gttgatttat  68460
ttaattctgt tgatgatgca attgggagta ttgcaaatta tctttatgtt catggatgga  68520
```

-continued agagagaagg aaagatcgta acaaaaactt atccaaacaa tgttagaaaa ttttataaac 68580
ctcatgagtc tctaacaagg ttcatacctt taatctttaa tgaagatgga aaagatcttt 68640
tttttattgg tgatgataac tttagggcta ttgctaagta taatattagc gatgtctatg 68700
caatggcggt ttattactta tcagaagagt taaaaaaatg aaaaaattat tattcacatt 68760
actatcaact tcaatattta ttcaagcaca gagttttgtt ccagattctc ctgagttaga 68820
tctgaagagc tatatcctaa ttgagccaaa caccaatact gttattgcag aatttaattc 68880
agatttggaa atagaaccag ctagcatgac taaaattatg actagctatg ttgtggctga 68940
tcagattgca aatggtttaa tatctcttga tgacgaagta ctaattagtg aaaaagcatg 69000
gagaatgcaa gggtctaaga cctttataga agctggaaaa aaagttacgg tatctgatct 69060
tttaaaaggt attatgattc agtcaggcaa tgatgcctct gttgcaattg cagaatatgc 69120
aggcggcact gaaagaggct tcgttgactt aatgaactct tatgctgcct ctttggagat 69180
gaataatacg atctttcaga attcaacagg gcttccagat gaaaatcatt tttcatcagc 69240
aaaagattta gccaatctga cagctaacta cattaataaa tttccagaag aatatgcttt 69300
atataagcag aagcaattta cttttaacaa tattaagcaa ttaaatagaa ataagctttt 69360
atggagagac gactcagcag atggtgttaa aactggtcat acagaagctg ctggatactg 69420
tttagttggc tcagcaaaaa ggggcggtat gaggcttatt acagttgttg caggaagtaa 69480
gtcagataat gatcgttttt tatcttccca aagattactt gagtatggat ttagattttt 69540
tacaacacag aagatgttaa gtgcagaaaa agaatatcag aatattacag tttggggtgg 69600
acaagaaaag atacttggcg tgggagttct agaggatata tctattactc ttcctagaac 69660
aagtttcaaa aatgttgaaa ctgtttataa agttaataac aatatccagg ctcctatcgt 69720
agttggtcaa aaagtcggga ctctagaaat aattagtaat gatgagattg ttctagttac 69780
ggatttggtt gctttaaaaa atattgaagc taaaggtttt tttggaagaa tatggtcaaa 69840
gttcgttctt tggatattta gcttatttgg tctaacagat gaaaacacca cttaaaggcg 69900
tttttaatgg ggcttttgat actgtagata acataaaaat atcacctttt tctcgagctt 69960
atactttttc tgatagcgta tatgaagtag ttcctttctt taattcaact gcaattgctt 70020
ttgatgatca tataaaaaga ttagaatttt ctgctagtca actagcgatg gccgtagatt 70080
taaaagaagt tatatttgaa attaattctt taataacatc atctgaattt agtaatggct 70140
atgtctatta tcaagttact cgaggcgttg atccattaag gtctcatatt catgagccaa 70200
atttaaaaat agaaaccttt ggctatgcaa aggcgcactt attccaatgg aaaccattaa 70260
gagtatcagt atgtgatgat attaggtggg ggaggtgtga tattaaatca acatcattgc 70320
ttggtaatgt tatgaacatg aatgcagcaa aactagataa ttgtgatgaa gttattatgc 70380
acaaagataa tttgttgacc gagggtggcg catctaatct tttttttgta aaaaatgatt 70440
caatctgcac cccagctcta aatggaaata tacttcccgg cataaccaga gcattactaa 70500
ttaatgaatt aaaaaattat agtatagagg tcatcgaaga taacttcagg ctagaagatt 70560
tatcaaatgc ttcttgcgcg tggctcacaa gcgcaacgaa agggctggcc cccatttctg 70620
aaattagtaa cctagaatct cacttggatt tataccatcc tcttttcaaa aagagtgaag 70680
aaatttttaa taagaagttc cttagttaga agtcagttta ataactatat tatcaagctc 70740
gtaccaaaaa tctttatcac taagaccttt atttgcaaga tcaagctcaa atacattttt 70800
ttggagctgt attaagtttt gtagtttatg atttttaata aaatgcatat attcagaagt 70860
tttatttttc caaaccccag atttaattag actatctaca ggatttttac tttgtctagc 70920

-continued attggctgca ctgttaataa ttttaccaac tatccaaact agaagaggtg cataatgatc 70980
ttccgctgat tttattgaat ggataatttt taaagcttgc ttggtattat ttgaaataat 71040
tttatcttca agctcaaatg gcataaattc tgcagactcc acagaaggtt ttctttcttg 71100
gccatcacca tctttataag tcagtcttag aagctttact tcattctgtt gggcaactaa 71160
gtttccagag ttcatttcag atatattttg cactaaagag ggcctatctt tttcagaaat 71220
aaaagatagt tgatgcttaa gccaaatctt ttcttcaaaa gatttaagtt ttccacaatc 71280
aatgatgagg gctatctcat ccatctgttt tacccactta gttgtgaaat taagcttttc 71340
attgcttgaa ttaataatta ttgcaatatt atccatatgg ttaatatttt caatttgaga 71400
tattttaatt atttggtcag gtatttttcc ttgatcatga ttaatctcaa ctattatttt 71460
tgagccaaat aaagatccag aagcattttc aataatagtc tgatctattt tatcaaaccc 71520
atctttatta ataattgttt tttctttgaa ccctttattt gataaatgtt tgagcaaaag 71580
atctttagag ttattttttta agacaacctc agatccaaaa ataaagaaga tattttgtga 71640
ctgatctaaa tatttttgag ttgtcattgc ctcacatttc aaaagcatgc acctcaaaaa 71700
ttatttgatc aattaattcc ttctgcattt cagactcaag agatttaatc atttgatctt 71760
gtgcaaatgg attaagttca ttcgatttat atctcttgta gctaacaagc tttttactta 71820
tttgtttatt tccaatcatt tttatatgta tttctaaatt aatttctcct tcaagagctc 71880
ttagagaaga gcctccatag atatcatatt tatttaaaat atagtcttgt attagaatct 71940
gattttgacg attctcagct tctttttctg tattgaagag gattgctaac ttttgctcaa 72000
aagaattagg gacactacta tcaaaccgaa aattaaatag atctttttta tctagatcta 72060
tatttagttg attaaattgg cagccagtta aagatatcaa caagcaagtg tataaaaaga 72120
aaggtcttag tttcataacc tcatagtatc tatctgaaga atatatatca aagattaatt 72180
ttaaataaca aaatttatta ttttttcttt aatataaata gttttttttaa tagccgagtt 72240 gtttattgtt gatgccacat tgtcgatagc cagtgctaaa gcttctatat ctttttgctc 72300
aaggtttttg tctatcatta ccttacctct cacctttcca tttacttgaa ctattaaatt 72360
aaattcagaa acttctaata actcctctct aagaacaggc caagaagatt caatttcttc 72420
ttgtgcaaag tcaaagtaaa aattattcca taaatgttgt gagatatgag gcgcaatagg 72480
attgagagtt ttaagaataa ttattattgc ttcattaaga caatattgat ttgagatcga 72540
cgcattacct tctttaaaag aatcaggtat aaagttaact agctccatta tcgaagcaat 72600
ggctgtatta aatgaatatc ttgtttcaaa gtcatttgta acctttttaa gagtattatg 72660
cgattttctt cggagctcta cttcttgttt cgaaggatcc ttgggctcct ctaagtcaat 72720
aaattttcta ttgctgacta agttccatat tttttcata aatcttgagg caccttctac 72780
agatgactct gaccattcta gactttgctc agggggagct gtaaacatca tgtaaagcct 72840
tacagtgtca gcgccatact tttctatata agattgagga tctacagtat ttccttttga 72900
tttggacatt ttagccccat ctttaagaac catgccttgt gtaagaagct ttttaaaagg 72960
ctcattgcct tcaactaaat ccatatctct aagcgcctta tgaaaaaatc ttgaatatag 73020
taagtgcagt atcgcatgct caatacctcc tatatataaa tcaacaggca gccaatattt 73080
tgaattttta tcaaacattt catctgcatt gtcagatgaa gtaaatcttg cgtaatacca 73140
tgatgagtcc ataaatgtat caaaagtatc tgtctctctt tttagtcgat cagaaatatt 73200
ataaaaatct tcattttgac ttaagggaat aggtgccgag ttcttttttta gctctggaag 73260

-continued

```
cactataggc atatcctttt catcaataac tcttggttca ccattttcat aaacaaccgg  73320
aatagggcaa ccccaatatc tttgtctgct cacaccccag tctcttaatc tgaactggat  73380
taactgctca ccaaggtttg cgtctgctaa atctttaata atttcaagag atgcctcatc  73440
agagtccatg ccatcatatt tatcagagtt tattaatttg cctttttgta caactggaag  73500
ttcattatta ttatcaaaac taataacttg aggaatctct agattatatt tagatgcaaa  73560
ttcgaaatct ctttgatcat gagcaggaac acccatcact actccagttc cataatcaag  73620
aagtacaaaa tttccaatcc atacgggtat cttcttcttt gtaattggat gaattacatg  73680
cattccacta ttaattccaa gtttttcagc tttagccata tcagcttcag cagctttcac  73740
ttctttgcat ttgtttagaa agtcttttat cgattcatta tttttgaca accctattga  73800
tatagagtga tttggtgata ttgctaaaaa agaaacacca aaaattgtat caggtcgtgt  73860
tgaaaatacc tttaaagaat catcggaatc ctcaatcatg tatttaattt ctgctccctg  73920
agatttccca atccaattcc tttgcattgt tttaacattt tcaggccaat ccacctcatc  73980
caaagatgtt aaaagttcct cagcgtagtc tgtaattttt ataaaccatt gatcaatttc  74040
ttttatttca acttgcgccc cagacctcca tccttttcca tctataactt gctcatttgc  74100
taaaactgtc tcatcaactg gatcccagtt cactaatgat tttttcctat aaaccaaacc  74160
tttatcataa aactttttaa atattaactg ctcccactta tagtattccg gttcacatgt  74220
tctaagctct tttgaccaat catacccaag gcccaaagat ataagttgct gtttcatatg  74280
ttcaatattt tgattcgtcc aatcttttgg gctaacttta ttagcaatcg ctgcgttttc  74340
agcaggaagc ccaaatgcat cccagcccat aggctgaaaa acattaaagt tattcattct  74400
tttatatcta gatatgacat caccgatcgt atagtttctt acatggccca tatgtaattt  74460
acctgatgga tatggaaaca ttgataggca ataaaatttt tctctaccat caggattagc  74520
tttaaatttg tcttctttta accattcatc ttgaatggtt ttctctattt gacttgggtt  74580
atattcagga ttcatttttt taggaactca ttttctaagt aattaatagt atgtttattt  74640
tctttaaagg tatcatcatg cagaatcctt tgatgaagag ggtgatttgt tttaatgccc  74700
tctataaaaa attcatctaa agcactcagc attctcttaa tagccgagct tctagaattt  74760
gcctgagtaa tgatttttgc tagaagtgaa tcatagttag ggggaactct atatcctcca  74820
taaatatgtg agtcatatct tatgccaaaa ccgccaggtg tatgcatttt tgtaattgtt  74880
cctggggatg gttgaaaatt atcaggatct tctgcattaa ttctgcattc tagtgagtgg  74940
ccatgaaaat taatatcatc ttgatttagc tcaattggca tttcaagagc aattcttagt  75000
tgtgctttta ctaaatcaaa gccagttatc atttctgtta ccggatgttc aacctgaatt  75060
cttgtattca tttctataaa atagaattga ttatcttcgt ataaaaattc aatagtgcca  75120
accccttcgt aatttatttc ttcacataaa ttgacacaag ctattagtgt tttattaaga  75180
gcttcttgat ttatattaag tgctggagct tcctcaatta ttttttgatg tctcctctgc  75240
atactgcaat cccttgtacc taaatgtatc gcctttcctt taccatcacc aactatttga  75300
acttcaatat gtctagggtt cccaataaat ttttctagat aaatggtttc attgccgaat  75360
ccatttttag cttcctgcat tgttatttct gcatgtccaa taagatcttc ctctctttca  75420
acaactctca ttcctcttcc accgccacca gccgttgcct taatcataat tggatagccg  75480
atatctctag caattttttt aaactcatca ttatcagatg gaatctcatc tttataacct  75540
ggaacgattt gaattccaga tttttcagcc agtgtttttg ctgttatttt gtcgcccatt  75600
ttttggattg tttctgaggt tggcccaata aatttaaatc cacttttttc acacatttct  75660
```

-continued

```
gcaaaattat gatcttctgc aaggaaccca tatccaggat atatagcatt agcacttgta  75720
agttctgcag ctgagagaat ggcaggtata tttaggtagc tttgagttgg agatgcaggc  75780
ccaatacaaa cagtttcatc agagaatctt aaatgtttta gatctttatc agcttctgag  75840
taaacagata ctgtcttgat accaagctct ttacaagctc ttatagctcg aagagcaatc  75900
tcaccacgat tggcaataag aactttataa ctcattttaa ttgacagtta taattttttg  75960
tccaaattca accggacttc catcttccac gtcaatactt gaaatcttgc catcaaattc  76020
tgatttaatt tcattcatca ttttcatggc ttcaactata cagagcacat cacctacttt  76080
tatattgtct cctactttta caaatggatc tttttcggga cttgggcttc tataaaaagt  76140
tcctactatt ggagaggtaa caacatcccc tatgacagtt tgcttagcct catccaattg  76200
atgagttgtt ggtgagatag ctggctcatt tttgacaatg attggttttg aaacaaattc  76260
ttgattagag ccgttatctc ttgaaattct tactgactca tctccttgac ttacttctat  76320
ttcttttaaa tcagactctt gaagcatttc tataagtttt tttattttcc taatatccat  76380
ttatttaccc ctgtatttta atatgccctt aagcatcgcc tcttcataac ccttagcacc  76440
aataccagtt atcacttctt cagctatatc agatagatat gagacatgtc taaattcctc  76500
tcttgtatat atgtctgaaa ggtgaacctc atagaatggt atgttgacac caagaaatgc  76560
atcccttata gctatgctcg tatgagtata tgcagcagga tttattatta caaagtctat  76620
tttttcttca atagtgctat gtattgattc tattatttca tgctccgcat tactttgaaa  76680
agatattaaa ttgcattgat tttgatttgc taagactaat aaatcttgtt gaatatcttc  76740
aagtgatttg ctgccatata cttccttttc tctagttccg agaagattga ggttggggcc  76800
atttataagc aatatattca tataatagat tttaacagaa atttacagat tttttaggat  76860
tttaaagata tttttataag agttgatttt tttgcatggg atagcaaaaa cccgcttcag  76920
agcatccctg atagtatatt aaaacctccg ataagttcaa tgaagaattt atttcaatgc  76980
ttataataaa ttcatctcta agaatctcag tctcgccaaa aaattcatcc ctatatagat  77040
ctttacttga ctcaagcgtc ttaaatggga gcactttatc tttaaatttg agctctatac  77100
tatccaagta catataataa ccatctctta tttgccaagt tatatatgct gcttgttttt  77160
caacattggt tgttaaagca aatacttcat tggcttctgg gaccctattt gagttttcaa  77220
aaagatttgc tgaattcaat tcacctgcaa tcacattgga tagtagtata attattaaac  77280
ttttgatcat gaagacttaa gaataaaccc ctaagtactt aaaataaaga ttttattaaa  77340
taacacggta gttaaaaatt tatgttccag actttcgcac taaaaatttt cttttatatg  77400
cctatttggc ttttaaaaat aattttttat agaaaaagaa cagtaataag agggcatcaa  77460
tttgatgctc aatctgctgc attattgtct ttgcttccaa agaaagattt atctgaatta  77520
ttagatggtg aaattgcaaa agctagaatt actcttgaag aagcaagaat tcaaaataaa  77580
gtttctttaa caccgtctat acaagtcaga aaagtagatc atattttacc aaagcatgat  77640
ttaattctca gagaatacaa gccgcatcaa gaggatttaa aaaaagttat tctctatttt  77700
catggaggag gttatgtcct taactcagtc aatacacatg atgatatggt ttcatatatg  77760
tcagataaaa taggagtaaa gttttattct ctagactata gactatcgcc tgagagcaaa  77820
tatcctgatt ctcttgatga tgctctagat gctttttctt ggctcatcgg ccagggatat  77880
ggaccaggtg atatttcagt ttgtggagac agcgcaggcg ctcatctagc tgcttctttg  77940
tgccattacc tagctgaaca aaataaagat ttgcctagta gccagctact aatatatcca  78000
```

-continued

```
atgtgtgatc cgtcctgttc atctgagtct tataatttat tatcttcagg atatcttcta  78060
actaaaaaaa ctatgatttg gttttgggat aagcttagaa cttccgaagt aaacaataac  78120
gattcggcct ttaatctctt aaaatttaat tttgaaaaaa ctttaccgcc aacaattatc  78180
gttacaggtg gctttgatcc tctatgcgat gatggagaaa aatatgcata tttattacat  78240
aaaggtaaac ataatgtgaa acaattacat tatccaacaa tgtttcatgg gtttgcatca  78300
atgactaaat tgaaagcagc gcagatagcc gttgaagatt ttttaaaaga atataagaaa  78360
atactatgag taaaatttta gaagtaagtg acttaagcat caatttttca acaagggatg  78420
gattgtttaa tgcagtggat aatataagtt ttgatataga aaaaaatcaa accttggcct  78480
tggttggtga gtcaggttct ggtaagtcgg taactgctat gtcaattctt cagctccttc  78540
aaaaaccaca agcatcatat tccaaagagt cttctattaa gtttaatggc gatgagataa  78600
taaatgccaa gtatgaaaag ttactttcct tgagaggaaa tattatatct atgatatttc  78660
aagagccgat gacctcacta aacccttatc acagagtagg taatcagata actgaatcaa  78720
tactacttca ctcaaaaagc tcaaaaaaag atgcaataga tgaagcaaaa aaattaatgg  78780
cacttgttga gattgatgat gttgaaagac ggttctatgc ataccctcat gagctttctg  78840
gagggcagcg acaaagagtt atgattgcta tggcccttgt taataaacct gagctattga  78900
ttgctgacga gccaacaacc gctcttgatg taactatcca agcccagata ttagatctca  78960
tgtctaagct taaaaatgaa ctaggcatgt caatactttt tattactcat gatctaggcc  79020
tcgttcaaga attttctgac aatgtttgtg ttatgaagaa tggcaagata gttgaacaag  79080
gaaatactgt tgaggtattt aacaacccct ctcacgaata tacaaaaaaa cttttagatg  79140
cagaacctca gcccaaatta gataaccctg taagtgatga gccaataatt gagatcaatg  79200
acttaaatgt ttactactca ataccttcaa ctaatttttt taaaaagaat acttttcatg  79260
ctgttaaaaa tacttccttt agtatttata aaaatactac aattggcctg gttggggaat  79320
ctggatctgg aaagtcaact ttgggtaagg ctatagcaaa cttagtttct tataagggga  79380
atattaaatt tgagggaaga gatatcaact caaattccca aaaagaaaat aaagaattga  79440
aaaaaaatgt ccaaattgtt tttcaagatc cttatgggtc attatcacca cgaatgacag  79500
tgggggagat agttggtgaa ggtttaggtg ttcactttaa gcttacaaaa aaagaaagag  79560
acgaaaggat agataaggtt ctgtcagatg tcggtatcga aatagtagct aagaataaat  79620
atccgcatga gttttctgga ggccaaaggc agagaattgc aattgctaga tctttaataa  79680
tgaatcctgc ttttatgatt cttgatgagc caacatcagc attagatagg tctattcaaa  79740
ttcaggtaat cgatttattg aaagagatac aaaatgaata tgggcttact tatcttttta  79800
taagtcatga tttaaaggtt attagatcga tgtcagactt tatttttgtt atgaaaaatg  79860
gagaaatcgt agagtcagga ccttctcaca aggtctttga aagcccagag caagactata  79920
ctaaaaaatt actatcagct gctttaaagt atgcatctga ataattaaat atatymcmtm  79980
tggcaaatag aaartattca aaagagctcg ttgacggtcc taatcaagct gcttctagat  80040
caatgcttag aggagtaggt ttcacatctg aggmtttcac aaaaccattt gttgggattg  80100
cttccacagg agcaaaagta accccatgca atatgcacat aaatgcactt tcagagatcg  80160
ttgagaaatc agttgatagt tcaggaggaa agggtgttct ttttaatact attactgttt  80220
ccgatggaat ttctatgggt acacaggta tgaaatattc tcttgtttct cgagaggtaa  80280
ttgcagattc aatagaaact gttgtgggat gtcttggtta tgatggagtt attgctgtcg  80340
gtggttgtga taaaaatatg cctggatgca ttattggaat ggcaagatta aatagaccat  80400
```

-continued

```
caatatttat atatggtggt tctatcaaac ctagtaaaga aaataccgac tatgttactg  80460
tttgtgagaa aactggagag tactcaaaag gcgatcttaa agaatctgaa ttaattcatg  80520
tagaaaaaat ttccgtaaaa gggcctggat cttgtggggg aatgtatacg gcaaatacta  80580
tggcttctgc gattgaagct ctaggcatga gtcttcctgg aagcagcagt caagatgcaa  80640
tttcacacga caaagaagat gattgtttta aggctggcga agcgataatg aatttattag  80700
aaaaagatat taagccttca gatattatga ctaagaatgc ttttgagaat gctataacaa  80760
tggtaattgc tctaggaggt tcaactaatg cagttctgca tttattggcc atggcgcatt  80820
caataggggt tgatttagag ctagatgact ttacaagaat aggaaaaaaa acacccgtta  80880
tggcagatct taagcccttt ggttctcatt atatgtctga actcaatgct aatggcggta  80940
ttcagccact aatgaaaact ttgcttgaga agggattact acacggcaat tgtcttaccg  81000
ttaccggtca gacgcttgct gaaaatcttt ctggaataaa accttacgag cctgatcaag  81060
agataattaa atcatttgat aatccaatta aatcaaatag ccatcttaga attctgtatg  81120
gcaacttagc gaaagatggt gcagttgcaa aaattacggg taaagaagga acttcctttg  81180
aaggaagtgc tcgtgtattt gattcagaag aagaaggggt taaagcaatc ctatctaaat  81240
ctataaaagc tggagatgtt gttgtaatta gatatgaagg gccaaaagga ggtccaggca  81300
tgagagaaat gctaaaacca acatctgcca taatgggtca aggtcttggc gatcaggtag  81360
cttttataac agacggtcgt ttttcaggag gcactcatgg atttgttgtt gggcacatta  81420
ctccagaggc tgcagatggc ggcttaattg caataattaa agatggcgac tctatattaa  81480
ttgatgcaga ttctgataag ttaattctta atatttctga ggatgaaatt tcaaatagac  81540
taagtagatg ggtaaaccca aaaacgcctc ccaaaaaagg agtcttagca aaatttgcaa  81600
aaagtgttaa atcagctagt cttggagcgg taacagatta aatatgtatt ttaaaagaaa  81660
atttccaaat agtagactaa gaagaatgcg tctcaattca aacctcagag acttgcttgc  81720
tgaagttagg ttgtctacaa atgatctaat tcagccatta tttataaaag aaggcttgag  81780
tggaaaagag gctattgaaa gcatgcccaa tattaataga tatggacaag attcaatttt  81840
ttcagaaata gaagagctac tagagcatga tataaatacg attgccctat ttccagttat  81900
taatgattcc aagaaaaaca gcactggaga tgaggctatc aatgcatcta atttgatgtg  81960
tgaaactatc agtaacataa agaaacgatt ccctgaaata atcttaatat ctgatgttgc  82020
tctagaccca tataccgatc atgggcatga cggtatttta aaaaatgatt atgttgataa  82080
tgatgagact ttagctgttt taaggaagca atcactaaca ttagctcagg ctgggacaga  82140
cataattgca ccatcagata tgatggatgg aagaataggc tctataagag aggcattgga  82200
cgaaatggat tataaaaata caatcctact atcatatgca gcaaaatata attcaaagtt  82260
ttatggtcca tttagagatg ctgttaattc agcttcaagt ctaggcaagt cttcaaaatc  82320
cagttatcaa atgtcaccaa aaaatataaa tgaagctcta catgaagttg ctatggatat  82380
taatgaaggt gcagacatag tcatggttaa gccaggtatg ccttatctag atataatttc  82440
aaaagtaaaa gaaaccttca aagtacctac ctttgcatac caggttagtg gtgaatatag  82500
catgcttaaa ctggcgattg ataaaggatg gcttgaaagc gatgttatgt tagaatcatt  82560
aataagtttt aaaagagcgg gagctgatgc aattctaacg tacgcagcta aagaaatttc  82620
caaggagata actaacaaat gagcaatgtg atagaaattc gtgatgaaga aagctttaat  82680
agcgacgtct taaattcaga aaaacctgta ttggttgatt tttgggctga gtggtgtgga  82740
```

-continued

```
ccttgtaaac agcttgcacc aactgttgaa acagttgcag cagaaaaatc agaaacatta  82800
aaggtttgca aaatggatgt tgattcaaat agagagattg ctgctaaata tggaataagg  82860
tcaatccctt cattaattat atttaaaaac ggagagcctg caggagttga agtaggtgct  82920
ctaaccaaac aacaattaga ggactttata agtacagtag tttaactttg caaagacttc  82980
tttgcatatt gcaagaaata ggattatcat ttcgacttct aaggctgaaa gccactcaaa  83040
acaaaaaccc accttttcaa tcataaaaac aacaactaga acggaaataa ctaaatgaac  83100
cttactgaaa ttaaaataaa accaataaat gaacttgtag atatagctac tgagcttggg  83160
cttgaggatg ttggaaggct gaaaaagcaa gagataatat ttagaatatt taagcataag  83220
gcttctgaag gtgttgatat ctatggtggc ggagttcttg agattttaaa tgatggtttt  83280
gggtttttgc gatccccaga aggctcttat tgcgctggcg aagatgatat ctatgtttca  83340
ccaagccaaa taagaaagtt tagcctcagg aagggagact cagttgctgg gaagataagg  83400
accccctaaag ataaagagcg ctattttgca ttaatccaag ttgatactat taatggtgaa  83460
gagccaagaa agactaaaaa caagattctt tttgaaaatt taactcctct ttttcccaat  83520
gaaagactaa tccttgaaca aggaacaggg tctaatgaag atctttcatc tcgaataatt  83580
gatttgattg ctccaatagg aaaaggtcag cgtggactta tcgtttctcc acccaaggct  83640
ggtaaaacct taatgcttca aagcatagct cattctatta aaagcaataa tccagaagta  83700
gagcttatag ttcttttgat tgatgaaaga cctgaagagg taacagagat gtcaagaact  83760
gtaaaaggag aggttgtagc tagtactttt gacgagccac ctactcgaca cgttcaagta  83820
gcaaatatgg ttattgaaaa agcaaaaaga cttgtagaac ataagaaaga tgtagttatc  83880
ttattagatt ctattactcg tcttggaaga gcatataact cagttcagcc tgcatcagga  83940
aagatattga gtggtggagt tgactccaat gctcttgaaa ggccaaaaag gttttttggt  84000
gctgctagaa atcttgaaga gggtggaagt ctcactattc ttgctactgc tctagttgaa  84060
acaggctcaa agatggatga agttatttat gaggaattca aaggtacggg taatatggag  84120
attcaccttg aaagaaaaat agccgaaaaa agaatatatc ctgctattaa tattagaaga  84180
tcgggaacaa gaagagaaga tttacttact gctgaagatg aattacaaag aatgtgggtc  84240
ttaaggaaaa ttttagacga tatggaagat gctcagtcaa ttcagttcct aatagataga  84300
ttgaaatctc ataaaacaaa cgatgagttc tttacttcaa tgaaaggggg taatggcaag  84360
aagactagat aaagtttttt gccatatcaa tcatcatctt atcagttggg ctttgcgata  84420
cgtgaatttc taattcttta aactcatttt gacatctatc ctttatattt tctgaagcaa  84480
caataaatat tttttttctt aaaactgcat cgtccagatt tgttattaag aatttaagag  84540
tactaaaatt atagattaaa aaaatttcat tattatctgt aacttttggt atttgctcca  84600
gcaaatagat tacttcatag caaactatct catctagact agccttaagt ttttgttgaa  84660
gaaaaccatt tgaattttcg ccgcaaaata aaagactctt tcctagaaaa tttttctcta  84720
ttaacttaag aattccttca gatgaatggc tttgtggaaa atgagatttt atgccacttt  84780
caagaagttt attggaagtt gcgggcccaa cagacaaaaa attgtgtgga agatcatcta  84840
aatcgaaaaa agattttaaa atatcaagtc cgtacgaagc agcagcttgg ctagtaaaaa  84900
ttaagtttga atatgaatga atatttttaa ttttatcgat agcgattttt gaagggtcga  84960
ttgaattaat tttagaaaga taaatatttt taagagctat ttcttgagct tcacataaag  85020
atattaggtt tcctgataaa tttttgggcc tcgtattaat tatcattttt taaaattaaa  85080
gatttcgctc cttccaaaat aaactcatca gcaaataaca taatatctat tgcaatatct  85140
```

-continued

```
tgaaaggaag atatcttttc tttataaatt ttttcgttgc cttcataaga taatattttc  85200
cctgatattt ttatttggcc atttttatct tcacataaaa tagctattgg agacaggcaa  85260
gtaccttcca tggcagcaac aaaagatcgc tctgcactgg caagaattaa ttctttaggg  85320
tcaccaatat tttctaaaag ctcaataata tctttttttat ctgacagaca ttcaattgct  85380
atatatccct gagatgcaga aggtaacatt tcttcaattg agaattcata tgaattttgt  85440
tttaaaccaa gcctttttat agcagcctta gcaactacca gcccatcaaa cagaccatca  85500
ttgagtttct ttattctagt agctatgttg cctcttactg gaatagtttt tatatcaggt  85560
cttaagttat taatttgtgc ttttcttctt ggaccagaag taccaatagt tgaatttcta  85620
gcaaattcag aaaatgattt cccatcctta gatagaagca ggtcttctgg agattcccta  85680
ctaaaaacac ttattatttt aaactttgga tcaagctttg ctggaacatc ttttaaacta  85740
tgcactgcaa tatctgcttc atcagcctct agagaggact caagtgtaga aatgaatagg  85800
ccctttccac caatttcatg aagaggttta tctgtttggt ctccttctga tgtcatagga  85860
acaagctcaa ccttaatatt attgatctta gctaataact catctgcaac aaattttgcc  85920
tgatacattg ctagttctga ttgccttgta gctattctta ttttcatttt gtttccaata  85980
aaagagcctt cacatcgcca acactctttt ctttcaagat agtgaattcc tcaggaattt  86040
ccaaggtagt aaatttacta tactcaaggt agattttaca agatggcttt atttcattct  86100
ttcgaattat agattttaga acttttaatt catattcttc gccaaaagga ggatcaagaa  86160
gaattaaatc aaaacgagat aagtcatttt ttttaatcca actaaatgca tccttaaaaa  86220
aaactttaga tttatccttg atgccaagaa gttgaatatt ttttgctaac acagaatagt  86280
tttttttatt aagttcaacg aacacaactt tttttgactg tctggatatt gcttcaatac  86340
caagcgcacc cgttccggca aacaaatcaa gacatattaa attttcaatc tcaaattgaa  86400
gccaattaaa aattatttct tttaatttat ttgaagttgg tcttaaggaa tccttaaatt  86460
cgaaaggtat ttttttacct tttaaataac ctccagtgat tctgatattg tttttcattt  86520
tttttgcaaa atgggtatgc ctatttatta aataaatata attamaaata catttaaact  86580
aagttataat tcatccatgm gtcctacaag ataattttag aaaagcaatg aggagctata  86640
tttactctgt cagtgtgatg tcaaatgttg acgagaataa aaagtttagt gctataacag  86700
tttcttcagt tacctctgtt tctttagatc ctcctagttt gctcgtttgt atcaataaat  86760
cagctggaat tcacaactca ataaaagaag ggtcctcttt ttgcataaac cttttaaata  86820
aaaatcaaga agatatttct aatctatgca gttcatttaa gaccgaaggt gatagattta  86880
atagtggtga ctgggattta agcggcactc cgtttttaaa aagtgcccag gctaatattt  86940
tttgtactgt tgatcaatta atttcatacc acacacatac tattgtgatt ggtcatgtca  87000
caaactctct tagcgatgag aaaattaata cactgacata tgttgatggt agctatgaat  87060
aaattttcaa aaaatgtatt ttttatttta ataatactca actctttttt tcttgcctct  87120
aacatttttg ctagccagga agagtgtgaa gaaaagccaa gtgtttttat tatctctcct  87180
caagacggtt ttatctcaga atctaataat gtaaaagtct tatttggatc aaaaaaatatt  87240
gaaataaatc cagctggcaa aggtgagatt gcaaaaaaata aatgttttgc aagcgggcat  87300
caccatcttt tagttaatat cgaagcattg ccagagagct ttattccttt tgacaagggt  87360
tatttacatt ttggaggagg tcaaactgaa acaattcttg atcttgatcc tggaacctat  87420
tctctccaac taattcttgg atcttatgtg cataattcaa aaatgcaggt aaataacttt  87480
```

-continued

```
aaaggtcaag gacccttttt atcagaaaaa ataacaatta cagttaatta gagattagac  87540
cagttataac tttatctaga tgttcatcta agttattagc aattatattt gcactagaaa  87600
taggaccaga attatcgtca taatcatcac caactacatt cacctttctt attatcccaa  87660
caagaccatg caacatagac caaagagtta tacatttaaa ggcaatcact tcctcaggct  87720
cgtctgctag attagcaaaa ctttttctca tattatcgta tgttccattt gcagatttaa  87780
gaagatctgg gtaatcggca aagttaccaa cagctgttcc aaacatcaaa tcatatgtat  87840
gtgcattttt taaaccaaac cctatatatt tgcttgcatt agtaacaagt tttttctttg  87900
taattttttt tggattctca aaaaaaacaa gctcattaag ttttttaaag ccaacggttg  87960
caacagcggc atatacacat tcttttgttt caaaatgcct ataaggagca gtttgagaaa  88020
caccactttc ctttgcaagg gatctaatac ttagtttagt gtaaccatct ctatcacaaa  88080
gcctgcatgc gcattctata agttcttcct ttaagtttcc gtgatgatag ttattcataa  88140
tttaatttta atgttgacac tgctaacata tatcatgtta ttatgtatac accgcataca  88200
ttaagttgat tacatattaa agtcaaatac agatatatga acataacaaa aataaataac  88260
accgtcatag ctcttttatt aggcaatgcg tttctatcaa atcttgaggc tttagaagtt  88320
cttgaggtta aaatgcttga tgaatatgct gtaactagag aatttcctgg aaagctcatt  88380
ccatcagacc agtctaagct agcatttgaa atacctggaa agataaactc tattaatgtt  88440
gatatcggag atgaggtcat cttaggggat gaacttgcct cattggatga tagagaagct  88500
ttagcacaat taaatcaatc aaaggctaaa tttgatttag ctgaacaagt actagcaaga  88560
tatataaatc tcagagcaga tggcatattt tctattcaag atcttgataa ggctgaatct  88620
gatcaaatag tagctaagtc gcagtatgat ttttatagag ttaaatttga gcaaactaag  88680
ttactagctc cttttaatgg agttattcaa aatagatttc tagatacagg atcagtaatc  88740
aatgcaggtg tccaagtttt agaaatttta ggctctagca atgttgaagc aagaatttct  88800
attccaatga actatatgaa caaggttaag attggagatg agtatgaatt tgatatcaga  88860
ggaatatcta caaaagctac gttagagaga ctggctccca tgtcaaccgg aggctccaat  88920
aataggttag caatttttag atttgatacc ttttttaatc caggatcaat agtaaagctc  88980
aaactaagca tcactgagaa agcaaaaggt acatgggttc caattaagtc actgtcccag  89040
tccgaacaag gtatttgggc catatatacc attaacgagc aacaagtagt tgttagagat  89100
cttgttgatg ttatttattt tgaagacgaa tatgcttttg tcagcggaac acttaataat  89160
ggtgatttag taattttagg cggagctcaa aaaattattg aaggaaaaat aataaaataa  89220
aatgaatgtt attaattttc taatagaaaa gcctaggata ttatttctaa ctttagcatt  89280
tatattactt tctggaattt cttctgggct ttcagttcca attcaagaaa accctgaact  89340
ggctgagaga tggggaggtg ttcgtatttt tcttcccggg gcatccccag aaagaattga  89400
aacagagata gtaaatgatc tagaaatcaa acttagagaa gttgaagaaa tcgatgagct  89460
tgaatcaatt attactcaag gtttttcaac aattgtagtt gaattaaatc aaagtgtacc  89520
tcctatactt attgaagaga cttggtccaa ggttcaagac aagctcaatc aaatagttat  89580
tcctcaaggt gcagaaatat ttcttgatag aagcagtggt ccgcctatca ctgttcagta  89640
tgctgtaacc tggaacggca gtggagatgc tccactaata atgatgtcca gactagcaag  89700
ccagctaaaa agaaaattaa gctcaatagg ctcatctcat caaactgcaa tttttggtga  89760
aacagatgaa gaaattttaa ttgaactaga ttcatcaaag ctatcttcgc ttggattatc  89820
atttcaagat atcgcaagtg ctattcaagc cctagatgca aaaaaaccta ttggtgtatc  89880
```

-continued

```
ctcaaacaac aattctgagc ttttatatag actcaaagat aatatacaga gcattcaaaa  89940
actctcagaa atacctatca aggttattaa taaatcagag atcatacagc tagatgatgt  90000
ggcatttatt tcaaaaatcc cggtttctcc tattgaagac atattcttgt ttaatggaaa  90060
tgtagttatt tctgttgctg gaaccggatc attttctcaa agagtccatg attatgtaga  90120
acgcgcaaca attgttgtag atgagatgag agaaactctg ccgactgaga tcactataga  90180
tttagtttat gacgaatctg cttacacaac taaaaaattt aatgagcttg taaaaagttt  90240
ttcattagca atatttttg ttttagcttt aagtcttttt tttcttggaa ttagatcagc  90300
aataattgtt actcttatcc tgccattttc tatttgcctg gttatgattg gttgtaggtt  90360
tataggctta cccttgcata tgacatctat cactggaatt attattgcac taggattgct  90420
tatagataat gggattattg ttgttgaaga ttataagaat agaagagcat ctggattaaa  90480
tatcaatgat tcaatttcac aaggactaaa aaacttatgg gctccattag ctgctgcaac  90540
agcaacaacc gtcttctctt ttcttcctat tgttactgga gaagggtcga gtattgaatt  90600
cgtaggcggc atggcaatga cagtcattat gtctataaca tcttcattag ttttggcgtt  90660
attaatggtt ccagttctga tgagttatat ggaaaaaatt ccgttcttta aggatgtgga  90720
tattagcaag gaagggtata gaaatgaaaa aatccttaat aaatataggg cctttttaaa  90780
ctgggcgttc ttagttccta gaagagcaat catgatatcg cttgcattgc ctgttctagg  90840
attctttctt tttaattctt tacctaaaga tttctttcct gctcaagata gagatatgtt  90900
tagagttaat atagaactgc cttctaacgc ctcatcactt actacaatgc agagagttaa  90960
ggaaattaga gaagatattc tagatagtga tttaatttca atagaaaaag attattcgtt  91020
tatcggcaga atgatgccta gagttttgat gaatgttgtt ggtggagaag aaaaacaagg  91080
atccaataat attgcgcagt ctgtattttt tgctactgat tattatgaaa tgattgaaaa  91140
ccttccagat ttatcaagaa gactggttaa aaataaccct gacattatag ttaatattga  91200
tagtttctcg tctggccccc cggttttttc agatgttagt tatgtaattt ttggagatga  91260
tccagattta ctaaaatcac ttggtgagga gctagagcta attattaaca attctcctga  91320
tgtgagtctt acgaaatctg caacttcaaa ctcaataacc aatgttgagt ttgaacttaa  91380
cagctcaaat atttcactgt ctggtcaaaa tgccaattat cttgtaaatg aaatgtttac  91440
tgcaaacaat ggaatatttg ttggcactat gttggattca aacaaagaaa taccagtcag  91500
gctgaaaggg ctgtctaata aaaacaatat tacgggaaat actagtttta taacaatgcc  91560
ctctcaaggt ggttttgagt attttgatag tttcggaaaa agctcactaa caaacaaatc  91620
gtcaacaatt actaggcttg atggccaaag aacaaatgat gttgagggct ggatttggac  91680
aggtacgctc ccgtctgcta ctgaaaaatc tattaaaaaa gatgttaaag attttgaatt  91740
aagattgcca ataggctatt cattaaaaca acttggcgag gctgaaagca ggggccaatc  91800
tcaagcctca ttatactctt cagcttttat gtatttcatt cttataatag taggcttggt  91860
tatggcgctt aattctttca gagaggctgg tctaattttg tctgttgcat tcttatcaat  91920
tggactatcc tttcttggtt tatttatagg ccagcaaaat tatggattta ttggaactat  91980
aagtgcaata gggttaattg gcttatcaat aaatgattca attattgtct tatctcacat  92040
aaaagaagag gctgagaaga aatcactaac caaagctgag cttgttgaag ttgttatcag  92100
gtctacacgt catataatca ctacctcttt gacaacactt ggtggttttc ttccacttat  92160
ttttgcaagt gtattcttca aaccgcttgc ttgggcaatg agcattggag tattaggcgc  92220
```

-continued gactattaca gccttattat atattcctgc aatgtttatg ataatgagaa aggttaagta 92280
ctagaacaac tttccgagca ataatttctt cctagctttt ttacaataag tgattcatga 92340
gtataggtct cgcaagaatc acatttaatc atagagttat caatcttttt tttatgaggt 92400
cctgatatga gagatctgaa aaagaatacc gcagttatta tcaatataaa tatgaccaat 92460
ggaatcaaaa gtaatatcga ttttaataag aacatttttt agtcactaga tgctggctta 92520
ctatttctta taaaattcca agaccagcca gacttatctt cagatttttt tgattgctca 92580
tcttggtagt taatagaaat tattttttta gtatcttcaa gcaattcaat atatcccaaa 92640
gattcatatg aagcctctaa gatcttaaga gctctataat tttcactaga gttaggaata 92700
ttttcaatta cataatttgc tcttcttatt gctgctatat gcgcatcaac actaacgtaa 92760
taatcagctg ccgcaagctc atttcttgca atcatatttc ttaaatagat atttctttgt 92820
ttagcatatg tagaatattg gctatcagga aatcttgtta agaattcagt tagttctgaa 92880
aatgattcct tagctcctga gatatctcta tttgatagat cagtatctgt cattcttaca 92940
ataaagctat tatctctcgt atagctagaa aggcctttca taaaatatgc ataatcaata 93000
tttggatgcc taggatgaag tcttataaat ttttctgctg cagcatgcgc agcctcagtt 93060
tcagcattca taaattgagc ataaataagc tctacttgcg cctgttcagc atatttgcca 93120
aaaggatatc ttgattcaat tgcttctaat gaatcaatag caccaaaata attttttcca 93180
gccatccttc tttgggcttg atcgtaataa attttttcag gctgttctat ttctgggcca 93240
tcagaattac aactaaccaa taacagagtt acaattggca atactataaa tagttttaaa 93300
attagtttat ctttcattat ttgcacattc tacctgcatt atcgtaattt aagcttgaaa 93360
acatctattt agattaattt ttttataata agttcatatg attgttaaaa atgttccaaa 93420
tgatctatct tcaatgaggc tagacaaagc tacagcagaa atgtttacag attattccag 93480
aactcagata aaaaaatgga tagaagaagg cagagttctt ataaatggag aggtatccca 93540
gccaagagat aaagtttatg agaatgatca gattgaatta agccctaaag aagaacaaaa 93600
agtatcatgg gaagctcaag atatagattt tgaaattcac tttgaaaatg aagattttat 93660
tataattaat aaacctgctg gtttaataat gcatccaggt tctggttgct atgatggaac 93720
tctcgcaaat gggctcattt ataaatttcc agaattgatc aatattccaa ggtcgggaat 93780
tgttcatcga ttagacaaag atacttctgg cattctgctc gtagcaagaa atgagtcttt 93840
taggaacttt tttattaatg aaatgcagga gaggagagtt gtaaaaaaat atacgtctat 93900
tgttattggt tctacactag gaagcttttc tatagaagag ccaattggaa gagataaaaa 93960
taatagaacc aaaatggcaa ttcgagaaga tggcaaagat gctttaacat ttgtaaagct 94020
taaagaaaat attggaaact actctgtgtt ggatataaga atagagacag gaagaactca 94080
tcagattagg gtccatctat catcaaaaaa actaccaata attggagata aaacctatga 94140
cccaagcagg tctattgcaa gagataccccc tgaagagcta attaatatta tccgaggttt 94200
tccaaggcag gcattacatg caacacacct ctcattcaat gaccaaaaaa caaataatat 94260
tttttctttt gatattccca ctccaaatga tatggaggaa ctacttctag aattaagaaa 94320
attgatctaa tagtaactaa aaacttgttt tttgattaat aaaataatat aaaccttatt 94380
cctaagagtt ttttggtaag aaattgaaat tatctggcgc agacatgcta atgcaagcac 94440
ttcatgatga aggtgttgag ctaatctttg gctacccagg tggagccgcg cttcatatct 94500
atgatgcaat ttttagacaa gataaaatag atcatatttt agtaaggcat gagcaaggtg 94560
caacccatgc agcagatgga tattcaaggg cgacaggtaa gccaggagtt gtcttagtca 94620

-continued

```
cttctggacc tggtgcaaca aatgctatta caggaatcgc gactgcattt atggattcca  94680
taccaatggt agttatttca gggcaggttg ctagccattt aataggtact gatgcttttc  94740
aagaaactga tatgattggt gtttcaagac caattgttaa gcatagctat acagttttta  94800
atgctgaaga aatacctaag ataattaaag aagcttttta tgtcgcaact tcaggcagac  94860
ctggacctgt tgttatagat atcccaaaag acatgacagc tccggataat ctttttgatt  94920
actcgtatcc tgaagaagcc aagataagat catacaatcc tccgattgag ccagaaaaaa  94980
atcaaataga tagagcagtc gaagctatat tgatatcaaa aaaaccagtt atatatgctg  95040
gtggtggggc aattgctagt aatgccgaaa aagaattact tgaacttaat gaaattattg  95100
atgctcctgt tacaaatact ttaatgggat tgggtattta ccctgctagt catcatagat  95160
ttcttgggat gttagggatg catggaacat atcaggcaaa tatggcaatg cataatgcag  95220
acttaataat tgctattggc gccagatttg atgacaggat taccaataaa ccatcaaagt  95280
ttgcacctaa tgccaaagtg gttcatctag atgttgatca ctcatctgta tcaaaaatta  95340
tagaagcaaa tgtagctgtt tttgggcaag taaaaaattc cttaaaatta ataaaagaaa  95400
ctcttgaaaa aaaattagac tcttacgatt ctttcgctct tcagccttgg cacgatcaga  95460
taaaagaatg gaaatcacta catggtttaa attatgagct ttataaagat gaatctgatg  95520
atcatcccat tttaccccag gctgtagtcc agcatgtcca tgagattaca aatggggaag  95580
catatgtgac ttccgatgtt ggtcagcatc aaatgtttgc tgctcaatat tatcattttg  95640
ataagcctag aagatggatc aattctggtg gtctaggaac tatgggtttt ggtttgccag  95700
cagcaatggg tgtaaaactc gcttttccaa aagatgaggt tgtttgcatt actggtgagg  95760
gtagtatcca aatgtgcatc caagaattgt ctacatgtct tcaatataat ctcccaataa  95820
aaataattaa tatcaataac gaagctcttg gtatggttaa acaatggcag gatatgaatt  95880
atggaggaag gcactctgaa agtacctatc aaaactcgtt accggatttt ataaaactgg  95940
ctgaatcata tggtcatata ggaattaaaa ttacaaaaaa ttctgattta agtgaaggct  96000
taaaaaaagc ttttgaaatg aaagataaac ttgtctttgt tgatatttat gtagatcctt  96060
cagagcatgt ttatccaatg caggttgcaa atggcagcct agaaaatatg tggctatcaa  96120
aggatgaaca aacatgatta aaagaaaact aattttaatt atggaaaata aaccaggagc  96180
tctagtaaga gtagttggac tgtttcatca aagaggctac aacattgaaa cccttcatgt  96240
agatactgtt aaagactttt ctacttacaa atcgatattg aaaaaaaact tgaaaccaaa  96300
tttgaggata atcaaatatc tagactgacc atagaaacaa tggtttcaga tgaccttatg  96360
aggcagattt tgagacagct caataaatta atagatgtta tagctgtaag caatgaagag  96420
acaacctatt taaaaggagt attattagat gaaaatttat tatgacgaag atgcaaacat  96480
agaaattatt aaagggatga atgtctcaat aattggctat ggatctcaag ggaatgctca  96540
tgcaaataat cttcatgaat ctggtgtaag tgttactgta ggtttaagag aagggtcttc  96600
ttcatgggca aaggcagaag aagcaggctt aaaagttcaa acagttgctg attcggtaat  96660
ccaagcagat ttggttatga ttttggcacc agatgaattc caaaaaaata tatatgaaac  96720
cgaaatcaag ccaaacttaa aaccagtgc aattcttgca tttgcacatg gctttaatat  96780
tcattttgaa aaaatagttc ctgaagcaac taacagcgta attatgattg caccaaaagg  96840
tccaggccat actgttagaa gtacttatac caatggtgga ggcgttccat ctctcatagc  96900
tatatatgaa gatgctttaa gtgatgaaga ttattcagca aaagatgtag ctctatctta  96960
```

-continued tgcaaaagca aatggcggca cgagggctgg tgttcttgaa acatctttta aagaagaaac 97020
agaaacagat ttatttggcg aacaagcagt tttatgtggc gggcttaccg ctttaattaa 97080
agctgggttt gaaactctag ttgaggcagg ctacagtgaa gagatggcat attttgaatg 97140
ccttcatgaa acaaaactaa tcacagactt aattcaagaa ggtggcattg ctaatatgca 97200
ttactcaata tcaaatactg ctgagtatgg tgattatgtg agtggaccca aagtaattac 97260
tagcgatacc aaaaaagcaa tgaaaggaat actagaaaat atacagtcag gaaaattcgc 97320
agatgacttc ttgaatgact gtcgacaaag caatgatggc actggcggac ctgttatgaa 97380
aagcaataga gaagctacaa aaattcatcc aatagagtcg gtaggggctg agctaaggtc 97440
taaaatgaag ttcctaaatt cacaaaaatt ggtggataaa gaaattaatt aaaattaatt 97500
aaaaaaaagg tatcttcttc ggaataactt cgttaagata cgcgtccgca caaagaggcg 97560
gttgttcttt aaaaatattt ggttactcgt gtgggtgttc aaaatacgag aaaaaataat 97620
ttagattttt tataaaaatc aacaaaacat gatattaatt gaagagtttg atcatggctc 97680
agattgaacg ctggcggtag gcttaacaca tgcaagtcgt gcgagaaagt atcttcggat 97740
atgagtagag cggcggacgg gtgagtaacg cgtaggaatc tacctagtag aaggggatag 97800
cccgggggaaa cccggattaa taccgtatac ctccttcggg agaaagaagg cctctctttg 97860
aagctttcgc tactagatga gcctgcgtaa gattagcttg ttggtgaggt aaaggctcac 97920
caaggcgacg atctttagct ggtctgagag gacgatcagc cacattggga ctgagacacg 97980
gcccagactc ctacgggagg cagcagtggg gaatattgga caatgggcgc aagcctgatc 98040
cagccatacc gcgtgtgtga agaaggcctt cgggttgtaa agcactttaa gcagggagaa 98100
aaagttataa gttaatacct tataaccctg atgttacctg cagaataagc accggctaat 98160
tccgtgccag cagccgcggt aatacggaag gtgcaagcgt taatcggaat tactgggcgt 98220
aaagcgcgcg taggtggttt gttaagttgg atgtgaaagc cctgggctca acctaggaac 98280
tgcatccaaa actaactcac tagagtacga tagagggagg tagaattcat agtgtagcgg 98340
tggaatgcgt agatattatg aagaatacca gtggcgaagg cggcctcctg gatctgtact 98400
gacactgagg tgcgaaagcg tgggtagcga acaggattag ataccctggt agtccacgcc 98460
gtaaacgatg acaactagct gttgggagac tatgtctttc agtggcgcag ctaacgcttt 98520
aagttgtccg cctggggagt acggccgcaa ggctaaaact caaatgaatt gacggggacc 98580
cgcacaagcg gtggagcatg tggtttaatt cgatgcaacg cgaaaaacct tacctactct 98640
tgacatactt ggaggctctt gtaatgagag tgtgcctttt ggaaccaaga tacaggtgct 98700
gcatggctgt cgtcagctcg tgtcgtgaga tgttccgtta agtcggataa cgagcgcaac 98760
ccttaccctt atttgccagc gattcggtcg ggaactataa ggggactgcc ggtgataaac 98820
cggaggaagg tgaggacgac gtcaagtcat catggccctt acgagtaggg ctacacacgt 98880
gctacaatgg gagatacaga cggacgctaa gccgcgaggt ggtgctaatc ctaaaaagtc 98940
tttcgtagtc cggattggag tctgcaactc gactccatga agtcggaatc gctagtaatc 99000
gcggatcagc atgccgcggt gaatacgttc tcgggtcttg tacacaccgc ccgtcacacc 99060
atggaagtgg attgcaccag aagtagatag tctaacctta gggagggcgt ttaccacggt 99120
gtgcttcatg actggggtga agtcgtaaca aggtagccgt aggggaacct gtggctggat 99180
cacctcctta acgataaatc gcgttttaaa cgcccacacg agtaatcaaa tattaaaaaa 99240
aagaacattt agatatgtaa aatcattggt atgtaatttt ctagtgtata catttatgta 99300
tacataagat cactgcaatt aaaaagtaac atatgcattt atgtgtatgt taaaaaagta 99360

-continued attaatatat tttattaagt tactctcaaa aatgaagata aaacttcaaa aaaaatatgt 99420
aaccttttt aaggttatat gatcaagtaa aggaagagca caaggcggat gccttggcag 99480
cataaggcga tgaaggacgt aataacctgc gataagcctc ggggagctgg taaataagct 99540
tcgatccgag gatttccgaa tgggaaaacc caatacacat aagtgtatta tcttatactg 99600
aatacatagg tataagaggc aaacctaggg aactgaaaca tctaagtacc tagaggaaaa 99660
gaaatcaaca gagattccgg tagtagcggc gagcgaaacc ggaccagccc ttaagcttat 99720
tttagtccag caaaatattc tggaaagttt agccatagta ggtgatagcc ctgtatgcga 99780
aagactaatt taagtgaaat cgagtaggtc gggacacgag aaatcttgac tgaacatggg 99840
gggaccatcc tccaaggcta aatactctat gctgaccgat agtgaaccag taccgtgagg 99900
gaaaggcgaa aagaaccccg gcgaggggag tgaaatagaa cctgaaacct tgtgcttaca 99960
agcagtcgga gcagacttgt tctgtgacgg cgtacctttt gtataatggg tcaacgactt 100020
aatttcagta gcaagcttaa ccatttaggg taggcgtagg gaaaccgagt cttaataggg 100080
cgctcagttg ctggaattag acccgaaacc gggtgatcta tccatggcca gtgtgaaggt 100140
cgagtaacat cgactggagg cgcgaaccca cttatgttga aaaatgaggg gatgagctgt 100200
ggataggagt gaaaggctaa tcaaacccgg agatagctgg ttctcttcga aaactattta 100260
ggtagtgcct cgtgtattac tgtagggggt agagcactgt ttcggctagg gggtcatccc 100320
gacttaccaa accgatgcaa actccgaata cctacaagta tgagcacggg agacagactg 100380
cgggtgctaa cgtccgtagt cgagagggaa acaacccaga ctgtcagcta aggtcccaaa 100440
ttatgattaa gtgggaaaca atgtgggaag gcacaaacag ctaggaggtt ggcttagaag 100500
cagccatcct ttaaagaaag cgtaatagct cactagtcga gtcggcctgc gtggaagata 100560
taacggggct aaatcataaa ccgaagctac agatcttaaa tttatttaag atggtagaag 100620
agcgttctgt aagcggttga aggtaagctg agaggcgaac tggacgtatc agaagtgcga 100680
atgttgacat gagtaacgat caaagaggtg aaaaacctct tcgccgaaaa accaagggtt 100740
cctgtccaac gctaatcgag gcagggtgag gcggccccta aggcgagggc gaaagccgta 100800
gtcgatggga aacaggttaa tattcctgta ctttttataa ctgcgatggg gtgacggaga 100860
aggttagact agcacggcga cggttgtccg tgttcaaggt tgtaggctgg tgttctaggt 100920
aaatccggaa cgctaaggct gagaactgat aacgaccact ctacgagtgg gaagtagtcg 100980
ataccatgct tccaggaaaa acctctaagc ttcaggttat aagaaaccgt accctaaacc 101040
gacacaggtg gttaggtcga gtagaccaag gtgtttgaga gaactatggt gaaggaacta 101100
ggcaaaatag caccgtaact tcgggagaag gtgcgccgcg tttggtgatg agacttgctc 101160
tctaagctga acgtggtcga agataccagg tggctgcgac tgtttactaa aaacatagca 101220
ctctgcaaac tcgtaagagg aagtataggg tgtgacgcct gcccggtgcc ggaaggttaa 101280
ttgatggggt tagcttatgc gaagctcttg atcgaagccc cggtaaacgg cggccgtaac 101340
tataacggtc ctaaggtagc gaaattcctt gtcgggtaag ttccgacctg cacgaatggc 101400
gtaacgatgg ccacactgtc tccaccatag actcagtgaa attgaaatcg ctgttaagat 101460
gcagtgtacc cgcagctaga cggaaagacc ccgtgcacct ttactatagg ttcgcactgg 101520
actttgacct tacttgtgta ggataggtgg gagactttga agcagagacg ccagtctttg 101580
tggagtcatc cttgaaatac cacccttgta agattgaagt tctaacctag gtccattatc 101640
tggatcaggg acagtgcgtg ctgggtagtt tgactggggc ggtctcctcc taaagagtaa 101700

-continued

```
cggaggagta cgaaggtatc cttatcacgg tcggacatcg tgaggtaagt ataaaggcag 101760
aaggatgctt gactgcgaga tcgacggatc gagcaggtag gaaactaggt cttagtgatc 101820
cggtggttct gaatggaagg gccatcgctc aacggataaa aggtacgccg gggataacag 101880
gctgataccg cccaagagtt catatcgacg gcggtgtttg gcacctcgat gtcggctcat 101940
cacatcctgg ggctggagca ggtcccaagg gtatggctgt tcgccattta aagtggtacg 102000
cgagctgggt ttagaacgtc gtgagacagt tcggtcccta tctgctgtgg gcgtttggag 102060
atttgaggga agctgattct agtacgagag gaccgaattg gacgaacctc tggtgttccg 102120
gttgtcacgc cagtggcatt gccgggtagc tatgttcgga aaggataacc gctgaaagca 102180
tataagcggg aagcctctcc caagattaaa tctcccagag actttatgtc tcctaaagag 102240
tcgtcataga ctatgacgtt gataggcaag atgtgtaagc gctgcgaggc gttgagctaa 102300
cttgtactaa taactcgtga ggcttgatca tgtaacctta agcaaggttc ataatttgag 102360
taaaacattg tagtgagaat taaaaaataa aaagttacat accagtttgc ctgatgacaa 102420
tagcaacttg gaaccacctg atcccatctc gaactcagaa gtgaaacgag ttaacgccaa 102480
tggtagtgca gggtctccct gtgtgagagt aggaaatcgt caggcttttt tctttaaggc 102540
ttccagttta ctggaagcct ttttttttat ctcaagtata atacccagat gattattgga 102600
ttaacaggag gcattggttc tggcaaatct gccgctgcag acttctttat tgatttaggt 102660
atatcagtct tagatgcaga tcaagttgct aaagaagctt tatctacaaa ttctcctgga 102720
tatactgatt ttatttctca atttggtgaa gtgtatttaa ataataatcg tgaggttgat 102780
aggctgaaat tgcgcgaact tattttttca aatccttcaa aaaaaaagga tcttgagaat 102840
attattcatc ccatagttcg gtctgctatt agtaatttta ttattacatc aacatcacca 102900
tattctattg ttatggtgcc actcattttt gaaacaaatt catataaaaa ttacgataag 102960
attattactg ttgactgtga tttagaactt cagatagtaa gggcctcaag tagagatgct 103020
caaaataaat cgcagattaa gaatattatt aataagcaag cctctagaga ggagaggcta 103080
agtatttctg atgacgtact tatcaataac agcaccctat ctgatctaaa aaaacaagtt 103140
aatgttttac atactaaata tatggagtta ttaaatgagt agttgcccta gatgtgaaaa 103200
acctgtcaaa ctttctactg acaatattta tagacctttc tgctctgaga aatgcaaact 103260
tatagatttt ggtgattggg ctaatgaaga taataaaatt tcaagaccaa ttcaatctga 103320
agatttttac gaagattaaa tttaagaaag tctccattca ccactttcaa tcatcggttt 103380
ggcttttttta tacttcattt cttgcgtatc ttgaccgtta gtaattttta caagatcatt 103440
tctgcctaac ttaggttcgt ttcttgtcac agtacttgtt tttactatag gagtggcttg 103500
tttttcattt tgaaagatat cagaattaat ttcctctttt tccaatttta attcttgaga 103560
actattttgt ttgtttatgc tctctagctc agattctgtc gatatttgta atgagaaaag 103620
tattcttata gtttcaacat ctatttccga aagcatagat tcaaacattg aatatgcctc 103680
tcttttgaat tcattttttg gatttttttg agcataagcc cttagaccaa cactatttct 103740
taaatgatct atttctgata aatgctcttt ccaatggaca tcaagtactt gcagcataac 103800
ctgcttctca agaagcaatc tattttcacc aagatcacta aactttttttg aatatttatt 103860
ttttgcttgc agaacaattt cttcggcaat tgtatttggt acaagttttt tattactatt 103920
aattttattg gctatatctg tttctagtcc atagctctct tttaaataat catcgagctg 103980
cctacttttc cattgagact ctattgattc ttcaggtaca tataaattag atattccttt 104040
gaattgctgc tcgatgagtg actcaatggt actgctaata tcttcctctt ctagtaattg 104100
```

-continued attccttaaa gaatatatag cttgtctttg atcatttgat acatcgtcgt actctaaaag 104160
atttttcctt gcatcaaagt ttctgctctc aattcttttt tgcgcatttt ctattcctct 104220
tgaaagcatt ttagcttcaa tatgatcatc tcccatgccc agcctttcaa aagtagccct 104280
tcttccatcc gaaataaaaa gtctcaagag atcgtcttct aaagataaga agaattttga 104340
ataacctgga tcaccttgtc tgcctgatct cccccttaac tgattatcta ttcttcttga 104400
ttcatgcctt tctgttccaa gtatatgaag cccaccagat tctataactt ttttattatt 104460
ttctttccac tctatatcgc tttggtcttc tttttttccg ccaagaacta tatccgtccc 104520
ccttcctgcc atattcgtag caatagttac cattccaggt ttacctgcat tggcaattat 104580
ctctgcttct ttttcgtgat gcttggcatt taaaatttga tgaggtattt ttttgttatt 104640
taaatatgct gatacttctt ctgaagattc aaccgaaact gttccaacaa gaatgggaga 104700
agattttttt cttaattgtt caatttcttc aattagagct ttatatttcg attctgttgt 104760
aagaaatact aagtcattaa gatcagctct agccatagga acatttgttg ggatgatgat 104820
gacatttagg ccatagattt gactaaactc tactgcttca gtatctgctg ttcctgtcat 104880
cccagaaagt tttttaaata atctaaaaaa gttttggaat gtggtggatg ctagtgtttg 104940
agactctctt tggatagcaa cattttcttt gcattccagt gcctggtgaa caccttcact 105000
cattcttctt ccgggcattg ttctacctgt atgctcatca atcaaaagaa cctcaccgtt 105060
cctaaccaaa taatccacat tctttttaaa taagaagctt gctctaagtg ttgcttgaac 105120
aaatttcata atttttaaat tagaaacaga gtaagcccat ctgaggctcc aagccgattc 105180
cagc 105184

<210> SEQ ID NO 2
<211> LENGTH: 29
<212> TYPE: DNA
<213> ORGANISM: pcr primer
<220> FEATURE:
<221> NAME/KEY: misc_feature
<222> LOCATION: (1)..(29)
<223> OTHER INFORMATION: Oligonucleotide primer for amplifying the proteorhodopsin gene. Forward primer

<400> SEQUENCE: 2
accatgggta aattattact gatattagg 29

<210> SEQ ID NO 3
<211> LENGTH: 24
<212> TYPE: DNA
<213> ORGANISM: pcr primer
<220> FEATURE:
<221> NAME/KEY: misc_feature
<222> LOCATION: (1)..(24)
<223> OTHER INFORMATION: Oligonucleotide primer for amplifying the proteorhodopsion gene.
Reverse primer

<400> SEQUENCE: 3
agcattagaa gattctttaa cagc 24

<210> SEQ ID NO 4
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Light-driven proton pump that is active when -continued expressed in E. coli, with retinal. An additional three
nucleotides are incorporated to native sequence (31A08) via pcr
primer (DNA residues 4-6, ggt), adding a new restriction site for
cloning/expression

<400> SEQUENCE: 4 atg ggt aaa tta tta ctg ata tta ggt agt gtt att gca ctt cct aca 48
Met Gly Lys Leu Leu Leu Ile Leu Gly Ser Val Ile Ala Leu Pro Thr
1 5 10 15 ttt gct gca ggt ggt ggt gac ctt gat gct agt gat tac act ggt gtt 96
Phe Ala Ala Gly Gly Gly Asp Leu Asp Ala Ser Asp Tyr Thr Gly Val
20 25 30 tct ttt tgg tta gtt act gct gct tta tta gca tct act gta ttt ttc 144
Ser Phe Trp Leu Val Thr Ala Ala Leu Leu Ala Ser Thr Val Phe Phe
35 40 45 ttt gtt gaa aga gat aga gtt tct gca aaa tgg aaa aca tca tta act 192
Phe Val Glu Arg Asp Arg Val Ser Ala Lys Trp Lys Thr Ser Leu Thr
50 55 60 gta tct ggt ctt gtt act ggt att gct ttc tgg cat tac atg tac atg 240
Val Ser Gly Leu Val Thr Gly Ile Ala Phe Trp His Tyr Met Tyr Met
65 70 75 80 aga ggg gta tgg att gaa act ggt gat tcg cca act gta ttt aga tac 288
Arg Gly Val Trp Ile Glu Thr Gly Asp Ser Pro Thr Val Phe Arg Tyr
85 90 95 att gat tgg tta cta aca gtt cct cta tta ata tgt gaa ttc tac tta 336
Ile Asp Trp Leu Leu Thr Val Pro Leu Leu Ile Cys Glu Phe Tyr Leu
100 105 110 att ctt gct gct gca act aat gtt gct gga tca tta ttt aag aaa tta 384
Ile Leu Ala Ala Ala Thr Asn Val Ala Gly Ser Leu Phe Lys Lys Leu
115 120 125 cta gtt ggt tct ctt gtt atg ctt gtg ttt ggt tac atg ggt gaa gca 432
Leu Val Gly Ser Leu Val Met Leu Val Phe Gly Tyr Met Gly Glu Ala
130 135 140 gga atc atg gct gca tgg cct gca ttc att att ggg tgt tta gct tgg 480
Gly Ile Met Ala Ala Trp Pro Ala Phe Ile Ile Gly Cys Leu Ala Trp
145 150 155 160 gta tac atg att tat gaa tta tgg gct gga gaa gga aaa tct gca tgt 528
Val Tyr Met Ile Tyr Glu Leu Trp Ala Gly Glu Gly Lys Ser Ala Cys
165 170 175 aat act gca agt cct gct gtg caa tca gct tac aac aca atg atg tat 576
Asn Thr Ala Ser Pro Ala Val Gln Ser Ala Tyr Asn Thr Met Met Tyr
180 185 190 att atc atc ttt ggt tgg gcg att tat cct gta ggt tat ttc aca ggt 624
Ile Ile Ile Phe Gly Trp Ala Ile Tyr Pro Val Gly Tyr Phe Thr Gly
195 200 205 tac ctg atg ggt gac ggt gga tca gct ctt aac tta aac ctt atc tat 672
Tyr Leu Met Gly Asp Gly Gly Ser Ala Leu Asn Leu Asn Leu Ile Tyr
210 215 220 aac ctt gct gac ttt gtt aac aag att cta ttt ggt tta att ata tgg 720
Asn Leu Ala Asp Phe Val Asn Lys Ile Leu Phe Gly Leu Ile Ile Trp
225 230 235 240 aat gtt gct gtt aaa gaa tct tct aat gct 750
Asn Val Ala Val Lys Glu Ser Ser Asn Ala
245 250

<210> SEQ ID NO 5
<211> LENGTH: 250
<212> TYPE: PRT
<213> ORGANISM: Naturally occurring gamma proteobacterium

<400> SEQUENCE: 5

-continued

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 6
<211> LENGTH: 747
<212> TYPE: DNA
<213> ORGANISM: Naturally occurring gamma proteobacterium
<220> FEATURE:
<221> NAME/KEY: CDS
<222> LOCATION: (1)..(747)
<223> OTHER INFORMATION: Native proteorhodpsion DNA sequence from BAC
      clone 31A08
<300> PUBLICATION INFORMATION:
<301> AUTHORS: Beja,O., Aravind,L., Koonin,E.V., Suzuki,M.T.,
      Hadd,A., Nguyen,L.P., Jovanovich,S.B., Gates,C.M., Feldman,R.A.,
      Spudich,J.L., Spudich,E.N. and DeLong,E.F.
<302> TITLE: Bacterial rhodopsin: evidence for a new type of phototrophy
      in the sea
<303> JOURNAL: Science
<304> VOLUME: 289
<305> ISSUE: 5486
<306> PAGES: 1902-1906
<307> DATE: 2000-09-15
<308> DATABASE ACCESSION NUMBER: AAG10475
<309> DATABASE ENTRY DATE: 2000-06-15
<313> RELEVANT RESIDUES: (1)..(747)

<400> SEQUENCE: 6

```
atg aaa tta tta ctg ata tta ggt agt gtt att gca ctt cct aca ttt       48
Met Lys Leu Leu Leu Ile Leu Gly Ser Val Ile Ala Leu Pro Thr Phe
1               5                   10                  15
```

-continued

```
gct gca ggt ggt ggt gac ctt gat gct agt gat tac act ggt gtt tct         96
Ala Ala Gly Gly Gly Asp Leu Asp Ala Ser Asp Tyr Thr Gly Val Ser
            20                  25                  30

ttt tgg tta gtt act gct gct tta tta gca tct act gta ttt ttc ttt        144
Phe Trp Leu Val Thr Ala Ala Leu Leu Ala Ser Thr Val Phe Phe Phe
        35                  40                  45

gtt gaa aga gat aga gtt tct gca aaa tgg aaa aca tca tta act gta        192
Val Glu Arg Asp Arg Val Ser Ala Lys Trp Lys Thr Ser Leu Thr Val
    50                  55                  60

tct ggt ctt gtt act ggt att gct ttc tgg cat tac atg tac atg aga        240
Ser Gly Leu Val Thr Gly Ile Ala Phe Trp His Tyr Met Tyr Met Arg
65                  70                  75                  80

ggg gta tgg att gaa act ggt gat tcg cca act gta ttt aga tac att        288
Gly Val Trp Ile Glu Thr Gly Asp Ser Pro Thr Val Phe Arg Tyr Ile
                85                  90                  95

gat tgg tta cta aca gtt cct cta tta ata tgt gaa ttc tac tta att        336
Asp Trp Leu Leu Thr Val Pro Leu Leu Ile Cys Glu Phe Tyr Leu Ile
            100                 105                 110

ctt gct gct gca act aat gtt gct gga tca tta ttt aag aaa tta cta        384
Leu Ala Ala Ala Thr Asn Val Ala Gly Ser Leu Phe Lys Lys Leu Leu
        115                 120                 125

gtt ggt tct ctt gtt atg ctt gtg ttt ggt tac atg ggt gaa gca gga        432
Val Gly Ser Leu Val Met Leu Val Phe Gly Tyr Met Gly Glu Ala Gly
    130                 135                 140

atc atg gct gca tgg cct gca ttc att att ggg tgt tta gct tgg gta        480
Ile Met Ala Ala Trp Pro Ala Phe Ile Ile Gly Cys Leu Ala Trp Val
145                 150                 155                 160

tac atg att tat gaa tta tgg gct gga gaa gga aaa tct gca tgt aat        528
Tyr Met Ile Tyr Glu Leu Trp Ala Gly Glu Gly Lys Ser Ala Cys Asn
                165                 170                 175

act gca agt cct gct gtg caa tca gct tac aac aca atg atg tat att        576
Thr Ala Ser Pro Ala Val Gln Ser Ala Tyr Asn Thr Met Met Tyr Ile
            180                 185                 190

atc atc ttt ggt tgg gcg att tat cct gta ggt tat ttc aca ggt tac        624
Ile Ile Phe Gly Trp Ala Ile Tyr Pro Val Gly Tyr Phe Thr Gly Tyr
        195                 200                 205

ctg atg ggt gac ggt gga tca gct ctt aac tta aac ctt atc tat aac        672
Leu Met Gly Asp Gly Gly Ser Ala Leu Asn Leu Asn Leu Ile Tyr Asn
    210                 215                 220

ctt gct gac ttt gtt aac aag att cta ttt ggt tta att ata tgg aat        720
Leu Ala Asp Phe Val Asn Lys Ile Leu Phe Gly Leu Ile Ile Trp Asn
225                 230                 235                 240

gtt gct gtt aaa gaa tct tct aat gct                                    747
Val Ala Val Lys Glu Ser Ser Asn Ala
                245


<210> SEQ ID NO 7
<211> LENGTH: 249
<212> TYPE: PRT
<213> ORGANISM: Naturally occurring gamma proteobacterium

<400> SEQUENCE: 7

Met Lys Leu Leu Leu Ile Leu Gly Ser Val Ile Ala Leu Pro Thr Phe
1               5                   10                  15

Ala Ala Gly Gly Gly Asp Leu Asp Ala Ser Asp Tyr Thr Gly Val Ser
            20                  25                  30

Phe Trp Leu Val Thr Ala Ala Leu Leu Ala Ser Thr Val Phe Phe Phe
        35                  40                  45

Val Glu Arg Asp Arg Val Ser Ala Lys Trp Lys Thr Ser Leu Thr Val
    50                  55                  60
```

-continued

```
Ser Gly Leu Val Thr Gly Ile Ala Phe Trp His Tyr Met Tyr Met Arg
65                  70                  75                  80

Gly Val Trp Ile Glu Thr Gly Asp Ser Pro Thr Val Phe Arg Tyr Ile
                85                  90                  95

Asp Trp Leu Leu Thr Val Pro Leu Leu Ile Cys Glu Phe Tyr Leu Ile
            100                 105                 110

Leu Ala Ala Ala Thr Asn Val Ala Gly Ser Leu Phe Lys Lys Leu Leu
        115                 120                 125

Val Gly Ser Leu Val Met Leu Val Phe Gly Tyr Met Gly Glu Ala Gly
    130                 135                 140

Ile Met Ala Ala Trp Pro Ala Phe Ile Ile Gly Cys Leu Ala Trp Val
145                 150                 155                 160

Tyr Met Ile Tyr Glu Leu Trp Ala Gly Glu Gly Lys Ser Ala Cys Asn
                165                 170                 175

Thr Ala Ser Pro Ala Val Gln Ser Ala Tyr Asn Thr Met Met Tyr Ile
            180                 185                 190

Ile Ile Phe Gly Trp Ala Ile Tyr Pro Val Gly Tyr Phe Thr Gly Tyr
        195                 200                 205

Leu Met Gly Asp Gly Gly Ser Ala Leu Asn Leu Asn Leu Ile Tyr Asn
    210                 215                 220

Leu Ala Asp Phe Val Asn Lys Ile Leu Phe Gly Leu Ile Ile Trp Asn
225                 230                 235                 240

Val Ala Val Lys Glu Ser Ser Asn Ala
                245


<210> SEQ ID NO 8
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: proteorhodopsin variant from clone EBAC40

<400> SEQUENCE: 8

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tcg ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gag act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta      336
Ile Asp Trp Leu Leu Thr Val Pro Leu Leu Ile Cys Glu Phe Tyr Leu
            100                 105                 110

att ctt gct gct gca aca aat gtt gct gct ggc ctg ttt aag aaa tta      384
Ile Leu Ala Ala Ala Thr Asn Val Ala Ala Gly Leu Phe Lys Lys Leu
```

-continued

```
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt      528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220

gac ctt gct gac ttt gtt aac aag att cta ttt ggt tta att ata tgg      720
Asp Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 9
<211> LENGTH: 250
<212> TYPE: PRT
<213> ORGANISM: Naturally occurring gamma proteobacterium

<400> SEQUENCE: 9

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Ala Gly Leu Phe Lys Lys Leu
        115                 120                 125

Leu Val Gly Ser Leu Val Met Leu Val Phe Gly Tyr Met Gly Glu Ala
    130                 135                 140

Gly Ile Met Asn Ala Trp Gly Ala Phe Val Ile Gly Cys Leu Ala Trp
145                 150                 155                 160

Val Tyr Met Ile Tyr Glu Leu Trp Ala Gly Glu Gly Lys Ala Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
```

-continued

```
        195                 200                 205

Tyr Leu Met Gly Asp Gly Gly Ser Ala Leu Asn Leu Asn Leu Ile Tyr
    210                 215                 220

Asp Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 10
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: proteorhodpsin variant from clone EBAC41

<400> SEQUENCE: 10

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gct act gct gct tta tta gca tct act gta ttt ttc      144
Ser Phe Trp Leu Ala Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta      336
Ile Asp Trp Leu Leu Thr Val Pro Leu Leu Ile Cys Glu Phe Tyr Leu
            100                 105                 110

att ctt gct gct gct act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

att atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ctg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220
```

-continued

```
aac ctt gct gat ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 11
<211> LENGTH: 250
<212> TYPE: PRT
<213> ORGANISM: Naturally occurring gamma proteobacterium

<400> SEQUENCE: 11

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Ala Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 12
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from clone EBAC64

<400> SEQUENCE: 12

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15
```

-continued

```
tttgct gca ggt ggc ggt gac ctt gat gct agt gat tac act ggt gtt        96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc       144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg       240
Val Ser Gly Leu Val Thr Gly Ile Ala Phe Trp His Tyr Met Tyr Met
65                  70                  75                  80

aga gga gta tgg att gaa act ggt gat tcg cct act gta ttt aga tac       288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta       336
Ile Asp Trp Leu Leu Thr Val Pro Leu Leu Ile Cys Glu Phe Tyr Leu
            100                 105                 110

att ctt gct gct gca act aat gtt gcc ggc tca tta ttt aag aaa ctt       384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca       432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg       480
Gly Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt       528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct       576
Asn Thr Ala Ser Pro Ser Val Gln Ser Ala Tyr Asn Thr Met Met Ala
            180                 185                 190

atc ata gtc ttc ggt tgg gca att tat cct ata ggt tat ttc aca ggt       624
Ile Ile Val Phe Gly Trp Ala Ile Tyr Pro Ile Gly Tyr Phe Thr Gly
        195                 200                 205

tac cta atg ggt gac ggt gga tca gct ctt aac tta aac ctt att tat       672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg       720
Asn Leu Ala Asp Phe Val Asn Lys Ile Leu Phe Gly Leu Ile Ile Trp
225                 230                 235                 240

aat gtt gct gtt aaa gaa tct tct aat gct                               750
Asn Val Ala Val Lys Glu Ser Ser Asn Ala
                245                 250


<210> SEQ ID NO 13
<211> LENGTH: 250
<212> TYPE: PRT
<213> ORGANISM: Naturally occurring gamma proteobacterium

<400> SEQUENCE: 13

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
```

-continued

```
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Tyr Ala Gly Glu Gly Lys Ser Ala Cys
                165                 170                 175

Asn Thr Ala Ser Pro Ser Val Gln Ser Ala Tyr Asn Thr Met Met Ala
            180                 185                 190

Ile Ile Val Phe Gly Trp Ala Ile Tyr Pro Ile Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 14
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone HOT01m:
      GenBank# AF349978

<400> SEQUENCE: 14

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tcg ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gag acc ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta      336
Ile Asp Trp Leu Leu Thr Val Pro Leu Leu Ile Cys Glu Phe Tyr Leu
            100                 105                 110
```

-continued

```
att ctt gct gct gca aca aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt      528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 15
<211> LENGTH: 250
<212> TYPE: PRT
<213> ORGANISM: Naturally occurring gamma proteobacterium

<400> SEQUENCE: 15

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Ala Gly Leu Phe Lys Lys Leu
        115                 120                 125

Leu Val Gly Ser Leu Val Met Leu Val Phe Gly Tyr Met Gly Glu Ala
    130                 135                 140

Gly Ile Met Asn Ala Trp Gly Ala Phe Val Ile Gly Cys Leu Ala Trp
145                 150                 155                 160

Val Tyr Met Ile Tyr Glu Leu Trp Ala Gly Glu Gly Lys Ala Ala Cys
                165                 170                 175

Asn Thr Ala Ser Pro Ala Val Gln Ser Ala Tyr Asn Thr Met Met Tyr
            180                 185                 190
```

-continued

```
Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 16
<211> LENGTH: 753
<212> TYPE: DNA
<213> ORGANISM: Naturally occurring gamma prtoeobacterium
<220> FEATURE:
<221> NAME/KEY: CDS
<222> LOCATION: (1)..(753)
<223> OTHER INFORMATION: Proteorhodopsin variant from pcr clone HOT75m1:
      GenBank#AF349979

<400> SEQUENCE: 16

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt gct      192
Phe Val Glu Arg Asp Gln Val Ser Ala Lys Trp Lys Thr Ser Leu Ala
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
```

-continued

```
Tyr Leu Met Gly Gly Glu Gly Val Tyr Ala Ser Asn Leu Asn Leu Ile
    210                 215                 220

tat aac ctt gcc gac ctt gtt aac aag att cta ttt ggt ttg atc att      720
Tyr Asn Leu Ala Asp Leu Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 17
<211> LENGTH: 251
<212> TYPE: PRT
<213> ORGANISM: Naturally occurring gamma prtoeobacterium

<400> SEQUENCE: 17

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Ala
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Leu Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 18
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone HOT75m3;
      GenBank#AF349980

<400> SEQUENCE: 18
```

-continued

```
atg ggt aaa tta tta ctg ata tta ggt agt gct att gca ctt cca tca        48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt        96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gta ttc ttt       144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act       192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg       240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat       288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta       336
Ile Asp Trp Leu Leu Thr Val Pro Leu Gln Met Val Glu Phe Tyr Leu
            100                 105                 110

att ctt gct gct tgt aca agt gtt gct gct tca tta ttt aag aag ctt       384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct       432
Leu Ala Gly Ser Leu Val Met Leu Gly Ala Gly Phe Ala Gly Glu Ala
    130                 135                 140

ggt tta gct cct gta tta cct gct ttc att att ggt atg gct gga tgg       480
Gly Leu Ala Pro Val Leu Pro Ala Phe Ile Ile Gly Met Ala Gly Trp
145                 150                 155                 160

tta tac atg att tat gag cta cat atg ggt gaa ggt aag gct gct gta       528
Leu Tyr Met Ile Tyr Glu Leu His Met Gly Glu Gly Lys Ala Ala Val
                165                 170                 175

agt act gca agt cct gct gtt aac tct gca tac aac gca atg atg aag       576
Ser Thr Ala Ser Pro Ala Val Asn Ser Ala Tyr Asn Ala Met Met Lys
            180                 185                 190

att att gtt att gga tgg gca att tat cct gct gga tat gct gct ggt       624
Ile Ile Val Ile Gly Trp Ala Ile Tyr Pro Ala Gly Tyr Ala Ala Gly
        195                 200                 205

tac cta atg agt ggt gac ggt gta tac gct tca aac tta aac ctt ata       672
Tyr Leu Met Ser Gly Asp Gly Val Tyr Ala Ser Asn Leu Asn Leu Ile
    210                 215                 220

tat aac ctt gct gac ttt gtt aac aag att cta ttt ggt ttg atc att       720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                           753
Trp Asn Val Ala Val Lys Glu Ser Ser Asn Ala
                245                 250


<210> SEQ ID NO 19
<211> LENGTH: 251
<212> TYPE: PRT
<213> ORGANISM: Naturally occurring gamma proteobacterium

<400> SEQUENCE: 19

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30
```

-continued

```
Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu His Met Gly Glu Gly Lys Ala Ala Val
                165                 170                 175

Ser Thr Ala Ser Pro Ala Val Asn Ser Ala Tyr Asn Ala Met Met Lys
            180                 185                 190

Ile Ile Val Ile Gly Trp Ala Ile Tyr Pro Ala Gly Tyr Ala Ala Gly
        195                 200                 205

Tyr Leu Met Ser Gly Asp Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 20
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone HOT75m4;
      GenBank #AF349981

<400> SEQUENCE: 20

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95
```

-continued

```
att gat tgg tta tta act gtt cca tta caa gtg gtt gag ttc tat cta      336
Ile Asp Trp Leu Leu Thr Val Pro Leu Gln Val Val Glu Phe Tyr Leu
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 21
<211> LENGTH: 251
<212> TYPE: PRT
<213> ORGANISM: Naturally occurring gamma proteobacterium

<400> SEQUENCE: 21

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Val Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
```

-continued

```
                165                 170                 175

Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 22
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone HOT75m8
      : GenBank#AF349982

<400> SEQUENCE: 22

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca aat gtt gct gct tca tta ttt aag aag ctt      384
Ile Leu Ala Ala Cys Thr Asn Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga ttg gct cct gta tgg cct gct ttc att att ggt atg gct gga tgg      480
Gly Leu Ala Pro Val Trp Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg gtg      576
Ser Thr Ala Ser Pro Ala Val Asn Ser Ala Tyr Asn Ala Met Met Val
            180                 185                 190

att att gtt gtt gga tgg gca att tat cct gct gga tat gct gct ggt      624
```

-continued

```
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220

tat aac ctt gcc gac ctt gtt aac aag att cta ttt ggt ttg atc att      720
Tyr Asn Leu Ala Asp Leu Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 23
<211> LENGTH: 251
<212> TYPE: PRT
<213> ORGANISM: Naturally occurring gamma proteobacterium

<400> SEQUENCE: 23

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Asn Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Trp Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Val
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Leu Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 24
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
```

-continued

```
<223> OTHER INFORMATION: Proteorhodopsin variant from pcr clone MB0m1
     : GenBank#AF349983

<400> SEQUENCE: 24

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gag act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta      336
Ile Asp Trp Leu Leu Thr Val Pro Leu Leu Ile Cys Glu Phe Tyr Leu
            100                 105                 110

att ctt gct gct gca aca aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg cct gca ttc att att ggg tgt tta gct tgg      480
Gly Ile Met Asn Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt gga tca gct ctt aac tta aac ctt att tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 25
<211> LENGTH: 250
<212> TYPE: PRT
<213> ORGANISM: Naturally occurring gamma proteobacterium

<400> SEQUENCE: 25

Met Gly Lys Leu Leu Leu Ile Leu Gly Ser Val Ile Ala Leu Pro Thr
1               5                   10                  15
```

```
Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Ala Gly Leu Phe Lys Lys Leu
        115                 120                 125

Leu Val Gly Ser Leu Val Met Leu Val Phe Gly Tyr Met Gly Glu Ala
    130                 135                 140

Gly Ile Met Asn Ala Trp Pro Ala Phe Ile Ile Gly Cys Leu Ala Trp
145                 150                 155                 160

Val Tyr Met Ile Tyr Glu Leu Tyr Ala Gly Glu Gly Lys Ser Ala Cys
                165                 170                 175

Asn Thr Ala Ser Pro Ser Val Gln Ser Ala Tyr Asn Thr Met Met Ala
            180                 185                 190

Ile Ile Val Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

```
<210> SEQ ID NO 26
<211> LENGTH: 750
<212> TYPE: DNA
<213> ORGANISM: Naturally ocurring gamma proteobacterium
<220> FEATURE:
<221> NAME/KEY: CDS
<222> LOCATION: (1)..(750)
<223> OTHER INFORMATION: Proteorhodopsin variant from pcr clone MB0m2

<400> SEQUENCE: 26

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac      288
```

-continued

```
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta      336
Ile Asp Trp Leu Leu Thr Val Pro Leu Leu Ile Cys Glu Phe Tyr Leu
            100                 105                 110

att ctt gct gct gct act aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gag ctt tgg ctt gga gaa gga aaa gct gcg tgt      528
Val Tyr Met Ile Tyr Glu Leu Trp Leu Gly Glu Gly Lys Ala Ala Cys
                165                 170                 175

aat aca gca agt cct gct gtt cag tca gct tac aac aca atg atg atg      576
Asn Thr Ala Ser Pro Ala Val Gln Ser Ala Tyr Asn Thr Met Met Met
            180                 185                 190

atc atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gca ctt aac tta aac ctt atc tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 27
<211> LENGTH: 250
<212> TYPE: PRT
<213> ORGANISM: Naturally ocurring gamma proteobacterium

<400> SEQUENCE: 27

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Ala Gly Leu Phe Lys Lys Leu
        115                 120                 125

Leu Val Gly Ser Leu Val Met Leu Val Phe Gly Tyr Met Gly Glu Ala
    130                 135                 140

Gly Ile Met Asn Ala Trp Gly Ala Phe Val Ile Gly Cys Leu Ala Trp
```

-continued

```
145                 150                 155                 160

Val Tyr Met Ile Tyr Glu Leu Trp Leu Gly Glu Gly Lys Ala Ala Cys
                165                 170                 175

Asn Thr Ala Ser Pro Ala Val Gln Ser Ala Tyr Asn Thr Met Met Met
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 28
<211> LENGTH: 750
<212> TYPE: DNA
<213> ORGANISM: Naturally occuring gamma proteobacterium
<220> FEATURE:
<221> NAME/KEY: CDS
<222> LOCATION: (1)..(750)
<223> OTHER INFORMATION: Proteorhodopsin variant from pcr clone MB20m2;
      GenBank #AF349985

<400> SEQUENCE: 28

atg ggt aaa tta tta ctg ata tta ggt agt gtt att gca ctt cct aca        48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt        96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc       144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act       192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg       240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac       288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta       336
Ile Asp Trp Leu Leu Thr Val Pro Leu Leu Ile Cys Glu Phe Tyr Leu
            100                 105                 110

att ctt gct gct gca act aat gtt gct gct ggc ctg ttt aag aaa tta       384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca       432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg       480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt       528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat       576
Asn Thr Ala Ser Pro Ala Val Gln Ser Ala Tyr Asn Thr Met Met Tyr
```

-continued

```
            180                 185                 190

ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

<210> SEQ ID NO 29
<211> LENGTH: 250
<212> TYPE: PRT
<213> ORGANISM: Naturally occuring gamma proteobacterium

<400> SEQUENCE: 29

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Ala Gly Leu Phe Lys Lys Leu
        115                 120                 125

Leu Val Gly Ser Leu Val Met Leu Val Phe Gly Tyr Met Gly Glu Ala
    130                 135                 140

Gly Ile Met Asn Ala Trp Gly Ala Phe Val Ile Gly Cys Leu Ala Trp
145                 150                 155                 160

Val Tyr Met Ile Tyr Glu Leu Trp Ala Gly Glu Gly Lys Ala Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 30
<211> LENGTH: 750
<212> TYPE: DNA
<213> ORGANISM: Naturally occurring gamma proteobacterium -continued

```
<220> FEATURE:
<221> NAME/KEY: CDS
<222> LOCATION: (1)..(750)
<223> OTHER INFORMATION: Proteorhodopsin variant from pcr clone MB20m5
      ; GenBank#AF349986

<400> SEQUENCE: 30

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta      336
Ile Asp Trp Leu Leu Thr Val Pro Leu Leu Ile Cys Glu Phe Tyr Leu
            100                 105                 110

att ctt gct gct gct act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

caa att atg gct gca tgg cct gca ttc att att ggg tgt tta gct tgg      480
Gln Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt ggg tca gct ctt aac tta aac ctt att tat      672
Tyr Leu Met Gly Asp Gly Gly Ser Ala Leu Asn Leu Asn Leu Ile Tyr
    210                 215                 220

aac ctt gct gac ttt gtt aac aag att cta ctt ggt tta att ata tgg      720
Asn Leu Ala Asp Phe Val Asn Lys Ile Leu Leu Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 31
<211> LENGTH: 250
<212> TYPE: PRT
<213> ORGANISM: Naturally occurring gamma proteobacterium

<400> SEQUENCE: 31
```

-continued

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gln Ile Met Ala Ala Trp Pro Ala Phe Ile Ile Gly Cys Leu Ala Trp
145                 150                 155                 160

Val Tyr Met Ile Tyr Glu Leu Tyr Ala Gly Glu Gly Lys Ser Ala Cys
                165                 170                 175

Asn Thr Ala Ser Pro Ser Val Gln Ser Ala Tyr Asn Thr Met Met Ala
            180                 185                 190

Ile Ile Val Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Leu Gly Leu Ile Ile Trp
225                 230                 235                 240

Asn Val Ala Val Lys Glu Ser Ser Asn Ala
                245                 250


<210> SEQ ID NO 32
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB20m12;
      GenBank #AF349987

<400> SEQUENCE: 32

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
```

-continued

```
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta      336
Ile Asp Trp Leu Leu Thr Val Pro Leu Leu Ile Cys Glu Phe Tyr Leu
            100                 105                 110

att ctt gct gct gca gct aat gtt gct gga tca tta ttt aag aaa tta      384
Ile Leu Ala Ala Ala Ala Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa tta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gcc tac aac aca atg atg tat      576
Asn Thr Ala Ser Pro Ala Val Gln Ser Ala Tyr Asn Thr Met Met Tyr
            180                 185                 190

att atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ttg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 33
<211> LENGTH: 250
<212> TYPE: PRT
<213> ORGANISM: Naturally occurring gamma proteobacterium

<400> SEQUENCE: 33

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Ala Asn Val Ala Gly Ser Leu Phe Lys Lys Leu
        115                 120                 125
```

-continued

```
Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 34
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB40m1;
GenBank #AF349988

<400> SEQUENCE: 34

```
atg ggt aaa tta tta ctg ata ata ggt agt gtt att gca ctt cct aca       48
Met Gly Lys Leu Leu Leu Ile Ile Gly Ser Val Ile Ala Leu Pro Thr
1               5                   10                  15

ttt gct gca ggt ggc ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta      336
Ile Asp Trp Leu Leu Thr Val Pro Leu Leu Ile Cys Glu Phe Tyr Leu
            100                 105                 110

att ctt gct gct gca act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tat atg att tat gaa cta tat gct gga gaa gga aaa tct gca tgt      528
Val Tyr Met Ile Tyr Glu Leu Tyr Ala Gly Glu Gly Lys Ser Ala Cys
```

-continued

```
                165                 170                 175

aat aca gca agt cct gct gtg caa tca gct tac aac aca atg atg tat       576
Asn Thr Ala Ser Pro Ala Val Gln Ser Ala Tyr Asn Thr Met Met Tyr
            180                 185                 190

att atc gtc ttt ggt tgg gcg att tat cct gta ggt tat ttc aca ggt       624
Ile Ile Val Phe Gly Trp Ala Ile Tyr Pro Val Gly Tyr Phe Thr Gly
        195                 200                 205

tac ctg atg ggt gac ggt gga tca gct ctt aac tta aac ctt atc tat       672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg       720
Asn Leu Ala Asp Phe Val Asn Lys Ile Leu Phe Gly Leu Ile Ile Trp
225                 230                 235                 240

aat gtt gct gtt aaa gaa tct tct aat gct                               750
Asn Val Ala Val Lys Glu Ser Ser Asn Ala
                245                 250


<210> SEQ ID NO 35
<211> LENGTH: 250
<212> TYPE: PRT
<213> ORGANISM: Naturally occurring gamma proteobacterium

<400> SEQUENCE: 35

Met Gly Lys Leu Leu Leu Ile Ile Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Tyr Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Val Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

-continued

```
<210> SEQ ID NO 36
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB40m5;p
      GenBank #AF349989

<400> SEQUENCE: 36

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tcg ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gag act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta ttg ata tgt gaa ttc tac tta      336
Ile Asp Trp Leu Leu Thr Val Pro Leu Leu Ile Cys Glu Phe Tyr Leu
            100                 105                 110

att ctt gct gct gca aca aat gtt gct gct ggc ctg ttt aag aaa tta      384
Ile Leu Ala Ala Ala Thr Asn Val Ala Ala Gly Leu Phe Lys Lys Leu
        115                 120                 125

ttg gtt ggt tct ctt gtt atg ctt gtg ttt ggt tac atg ggt gag gca      432
Leu Val Gly Ser Leu Val Met Leu Val Phe Gly Tyr Met Gly Glu Ala
    130                 135                 140

gga att atg aac gct tgg ggt gca ttc gtt att ggg tgt tta gct tgg      480
Gly Ile Met Asn Ala Trp Gly Ala Phe Val Ile Gly Cys Leu Ala Trp
145                 150                 155                 160

gta tac atg att tat gaa cta tgg gct gga gaa ggc aag gct gca tgt      528
Val Tyr Met Ile Tyr Glu Leu Trp Ala Gly Glu Gly Lys Ala Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

ata atc atc ttt ggt tgg gca att tat cct gta ggt tat ttc aca ggt      624
Ile Ile Ile Phe Gly Trp Ala Ile Tyr Pro Val Gly Tyr Phe Thr Gly
        195                 200                 205

tac cta atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220

aac ctt gct gac ttt gtt aac aag aat cta ttt ggt tta att ata tgg      720
Asn Leu Ala Asp Phe Val Asn Lys Asn Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 37
<211> LENGTH: 250
```

-continued

<212> TYPE: PRT
<213> ORGANISM: Naturally occurring gamma proteobacterium

<400> SEQUENCE: 37

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Ala Gly Leu Phe Lys Lys Leu
        115                 120                 125

Leu Val Gly Ser Leu Val Met Leu Val Phe Gly Tyr Met Gly Glu Ala
    130                 135                 140

Gly Ile Met Asn Ala Trp Gly Ala Phe Val Ile Gly Cys Leu Ala Trp
145                 150                 155                 160

Val Tyr Met Ile Tyr Glu Leu Trp Ala Gly Glu Gly Lys Ala Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Asn Leu Phe Gly Leu Ile Ile Trp
225                 230                 235                 240

Asn Val Ala Val Lys Glu Ser Ser Asn Ala
                245                 250
```

<210> SEQ ID NO 38
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB40m12;
GenBank # AF34999

<400> SEQUENCE: 38

```
atg ggt aaa tta tta cgg ata tta ggt agt gtt att gca ctt cct aca       48
Met Gly Lys Leu Leu Arg Ile Leu Gly Ser Val Ile Ala Leu Pro Thr
1               5                   10                  15

ttt gct gca ggt ggc ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
```

-continued

```
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tat atg      240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta      336
Ile Asp Trp Leu Leu Thr Val Pro Leu Leu Ile Cys Glu Phe Tyr Leu
            100                 105                 110

att ctt gct gct gca act aat gtt gct gga tca tta ttt aag aaa tta      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

atc atc atc gtt ggt tgg gcg att tat cct gta ggt tat ttc aca ggt      624
Ile Ile Ile Val Gly Trp Ala Ile Tyr Pro Val Gly Tyr Phe Thr Gly
        195                 200                 205

tac ctg atg ggt gac ggt gga tca gct ctt aac tta aac ctt atc tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 39
<211> LENGTH: 250
<212> TYPE: PRT
<213> ORGANISM: Naturally occurring gamma proteobacterium

<400> SEQUENCE: 39

Met Gly Lys Leu Leu Arg Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110
```

-continued

```
Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 40
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB100m5;
      GenBank #AF349991

<400> SEQUENCE: 40

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt aca gct gct cta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta      336
Ile Asp Trp Leu Leu Thr Val Pro Leu Leu Ile Cys Glu Phe Tyr Leu
            100                 105                 110

att ctt gct gct gca act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg      480
Gly Ile Met Ala Ala Trp Pro Ala Phe Ile Ile Gly Cys Leu Ala Trp
```

-continued

```
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt gga tca gct ctt aac tta aac ctt att tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 41
<211> LENGTH: 250
<212> TYPE: PRT
<213> ORGANISM: Naturally occurring gamma proteobacterium

<400> SEQUENCE: 41

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Tyr Ala Gly Glu Gly Lys Ser Ala Cys
                165                 170                 175

Asn Thr Ala Ser Pro Ser Val Gln Ser Ala Tyr Asn Thr Met Met Ala
            180                 185                 190

Ile Ile Val Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240
```

-continued

```
Asn Val Ala Val Lys Glu Ser Ser Asn Ala
                245                 250


<210> SEQ ID NO 42
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB100m7;
      GenBank #AF349992

<400> SEQUENCE: 42

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tac atg      240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct cta tta ata tgt gaa ttc tac tta      336
Ile Asp Trp Leu Leu Thr Val Pro Leu Leu Ile Cys Glu Phe Tyr Leu
            100                 105                 110

att ctt gct gct gct act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga att atg gca gct tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tat gct gga gaa gga aaa tct gca tgt      528
Val Tyr Met Ile Tyr Glu Leu Tyr Ala Gly Glu Gly Lys Ser Ala Cys
                165                 170                 175

aat act gca agt cct tcg gtt caa tca gct tac aac aca atg atg gct      576
Asn Thr Ala Ser Pro Ser Val Gln Ser Ala Tyr Asn Thr Met Met Ala
            180                 185                 190

atc ata gtc ttc ggt tgg gca att tat cct gta ggt tat ttc aca ggt      624
Ile Ile Val Phe Gly Trp Ala Ile Tyr Pro Val Gly Tyr Phe Thr Gly
        195                 200                 205

tac cta atg ggt gac ggt gga tca gct ctt aac tta aac ctt att tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gct gct gtt aaa gaa tct tct aat gct                              750
Asn Ala Ala Val Lys Glu Ser Ser Asn Ala
                245                 250
```

<210> SEQ ID NO 43
<211> LENGTH: 250
<212> TYPE: PRT
<213> ORGANISM: Naturally occurring gamma proteobacterium

<400> SEQUENCE: 43

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Tyr Ala Gly Glu Gly Lys Ser Ala Cys
                165                 170                 175

Asn Thr Ala Ser Pro Ser Val Gln Ser Ala Tyr Asn Thr Met Met Ala
            180                 185                 190

Ile Ile Val Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Ala Ala Val Lys Glu Ser Ser Asn Ala
                245                 250
```

<210> SEQ ID NO 44
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB100m9;
GenBank #AF349993

<400> SEQUENCE: 44

```
atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggt ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt act gct gct tta tta gca tct act gta ttt ttc      144
```

-continued

```
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tat atg      240
Val Ser Gly Leu Val Thr Gly Ile Ala Phe Trp His Tyr Met Tyr Met
65                  70                  75                  80

aga ggg gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

ata gat tgg tta cta aca gtt cct tta tta ata tgt gaa ttc tac tta      336
Ile Asp Trp Leu Leu Thr Val Pro Leu Leu Ile Cys Glu Phe Tyr Leu
            100                 105                 110

att ctt gcc gct gca act aat gtt gct gga tca tta ttt aag aaa tta      384
Ile Leu Ala Ala Ala Thr Asn Val Ala Gly Ser Leu Phe Lys Lys Leu
        115                 120                 125

ctt gtt ggt tct ctt gtt atg ctt gtg ttt ggt tac atg ggt gaa gca      432
Leu Val Gly Ser Leu Val Met Leu Val Phe Gly Tyr Met Gly Glu Ala
    130                 135                 140

gga atc atg gct gca tgg cct gca ttc att att ggg tgt tta gct tgg      480
Gly Ile Met Ala Ala Trp Pro Ala Phe Ile Ile Gly Cys Leu Ala Trp
145                 150                 155                 160

gta tac atg att tat gaa cta tgg gct gga gaa gga aaa tct gca tgt      528
Val Tyr Met Ile Tyr Glu Leu Trp Ala Gly Glu Gly Lys Ser Ala Cys
                165                 170                 175

aat act gca agt cct gct gtg caa tca gct tac aac aca atg atg tat      576
Asn Thr Ala Ser Pro Ala Val Gln Ser Ala Tyr Asn Thr Met Met Tyr
            180                 185                 190

atc atc atc ttt ggt tgg gcg att tat cct gta ggt tat ttc aca ggt      624
Ile Ile Ile Phe Gly Trp Ala Ile Tyr Pro Val Gly Tyr Phe Thr Gly
        195                 200                 205

tac ctt atg ggt gac ggt gga tca gca ctt aac tta aac ctt att tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250
```

```
<210> SEQ ID NO 45
<211> LENGTH: 250
<212> TYPE: PRT
<213> ORGANISM: Naturally occurring gamma proteobacterium

<400> SEQUENCE: 45

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
```

-continued

```
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 46
<211> LENGTH: 750
<212> TYPE: DNA
<213> ORGANISM: Naturally occurring gamma proteobacterium
<220> FEATURE:
<221> NAME/KEY: CDS
<222> LOCATION: (1)..(750)
<223> OTHER INFORMATION: Proteorhodopsin variant from pcr clone MB100m10
     ; GenBank #AF34999

<400> SEQUENCE: 46

atg ggt aaa tta tta ctg ata tta ggt agt gtt att gca ctt cct aca       48
Met Gly Lys Leu Leu Leu Ile Leu Gly Ser Val Ile Ala Leu Pro Thr
1               5                   10                  15

ttt gct gca ggt ggc ggt gac ctt gat gct agt gat tac act ggt gtt       96
Phe Ala Ala Gly Gly Gly Asp Leu Asp Ala Ser Asp Tyr Thr Gly Val
            20                  25                  30

tct ttt tgg tta gtt aca gct gct cta tta gcg tct act gta ttt ttc      144
Ser Phe Trp Leu Val Thr Ala Ala Leu Leu Ala Ser Thr Val Phe Phe
        35                  40                  45

ttt gtt gaa aga gat aga gtt tct gca aaa tgg aaa aca tca tta act      192
Phe Val Glu Arg Asp Arg Val Ser Ala Lys Trp Lys Thr Ser Leu Thr
    50                  55                  60

gta tct ggt ctt gtt act ggt att gct ttc tgg cat tac atg tat atg      240
Val Ser Gly Leu Val Thr Gly Ile Ala Phe Trp His Tyr Met Tyr Met
65                  70                  75                  80

aga gga gta tgg att gaa act ggt gat tcg cca act gta ttt aga tac      288
Arg Gly Val Trp Ile Glu Thr Gly Asp Ser Pro Thr Val Phe Arg Tyr
                85                  90                  95

att gat tgg tta cta aca gtt cct tta tta ata tgt gaa ttc tac tta      336
Ile Asp Trp Leu Leu Thr Val Pro Leu Leu Ile Cys Glu Phe Tyr Leu
            100                 105                 110

att ctt gct gct gca act aat gtt gcc ggc tca tta ttt aag aaa ctt      384
Ile Leu Ala Ala Ala Thr Asn Val Ala Gly Ser Leu Phe Lys Lys Leu
        115                 120                 125

cta gtt ggt tct ctt gtt atg ctt gtg ttt ggt tac atg ggt gaa gca      432
Leu Val Gly Ser Leu Val Met Leu Val Phe Gly Tyr Met Gly Glu Ala
```

-continued

```
    130                 135                 140

gga ata atg gcg gct tgg cct gca ttc atc gtt gga tgt tta gca tgg      480
Gly Ile Met Ala Ala Trp Pro Ala Phe Ile Val Gly Cys Leu Ala Trp
145                 150                 155                 160

gta tat atg att tat gaa cta tgg gct ggt gaa gga aaa tct gca tgt      528
Val Tyr Met Ile Tyr Glu Leu Trp Ala Gly Glu Gly Lys Ser Ala Cys
                165                 170                 175

aat act gca agt cct gct gta cag tca gct tac aac aca atg atg tat      576
Asn Thr Ala Ser Pro Ala Val Gln Ser Ala Tyr Asn Thr Met Met Tyr
            180                 185                 190

atc atc atc gtt ggt tgg gca att tat cct gta ggt tat ttc aca ggt      624
Ile Ile Ile Val Gly Trp Ala Ile Tyr Pro Val Gly Tyr Phe Thr Gly
        195                 200                 205

tac cta atg ggt gac ggt gga tca gct ctt aat cta aac ctt att tat      672
Tyr Leu Met Gly Asp Gly Gly Ser Ala Leu Asn Leu Asn Leu Ile Tyr
    210                 215                 220

aac ctt gct gac ttt gtt aac aag att cta ttt ggt tta att ata tgg      720
Asn Leu Ala Asp Phe Val Asn Lys Ile Leu Phe Gly Leu Ile Ile Trp
225                 230                 235                 240

aat gtt gct gtt aaa gaa tct tct aat gct                              750
Asn Val Ala Val Lys Glu Ser Ser Asn Ala
                245                 250


<210> SEQ ID NO 47
<211> LENGTH: 250
<212> TYPE: PRT
<213> ORGANISM: Naturally occurring gamma proteobacterium

<400> SEQUENCE: 47

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Val Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220
```

-continued

```
Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 48
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PALB1;
      GenBank #AF349995

<400> SEQUENCE: 48

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gta ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg      240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat      288
Arg Gly Val Trp Ile Asp Thr Gly Asp Thr Pro Thr Val Phe Arg Tyr
                85                  90                  95

att gat tgg cta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

ggt tta gct cct gta tta cct gct ttc att ctt ggt atg gct ggt tgg      480
Gly Leu Ala Pro Val Leu Pro Ala Phe Ile Leu Gly Met Ala Gly Trp
145                 150                 155                 160

tta tac atg att tat gag cta cat atg ggt gaa ggt aag gct gct gta      528
Leu Tyr Met Ile Tyr Glu Leu His Met Gly Glu Gly Lys Ala Ala Val
                165                 170                 175

agt act gca agt cct gct gtt aac tct gct tac aat gca atg atg aag      576
Ser Thr Ala Ser Pro Ala Val Asn Ser Ala Tyr Asn Ala Met Met Lys
            180                 185                 190

att att gtt att gga tgg gca att tat cct gct gga tat gct gct ggt      624
Ile Ile Val Ile Gly Trp Ala Ile Tyr Pro Ala Gly Tyr Ala Ala Gly
        195                 200                 205

tac cta atg agt ggt gac ggt gta tac gct tca aac tta aac ctt ata      672
Tyr Leu Met Ser Gly Asp Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240
```

-continued

```
tgg aat gtt gct gtt aaa gaa tct tct aat gct                      753
Trp Asn Val Ala Val Lys Glu Ser Ser Asn Ala
                245                 250


<210> SEQ ID NO 49
<211> LENGTH: 251
<212> TYPE: PRT
<213> ORGANISM: Naturally occurring gamma proteobacterium

<400> SEQUENCE: 49

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Leu Gly Met Ala Gly Trp
145                 150                 155                 160

Leu Tyr Met Ile Tyr Glu Leu His Met Gly Glu Gly Lys Ala Ala Val
                165                 170                 175

Ser Thr Ala Ser Pro Ala Val Asn Ser Ala Tyr Asn Ala Met Met Lys
            180                 185                 190

Ile Ile Val Ile Gly Trp Ala Ile Tyr Pro Ala Gly Tyr Ala Ala Gly
        195                 200                 205

Tyr Leu Met Ser Gly Asp Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 50
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PALB2;
      GenBank #AF349996

<400> SEQUENCE: 50

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
```

-continued

```
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct gag tgg aaa act tca ctt act      192
Phe Val Glu Arg Asp Gln Val Ser Ala Glu Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gat act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 51
<211> LENGTH: 251
<212> TYPE: PRT
<213> ORGANISM: Naturally occurring gamma proteobacterium

<400> SEQUENCE: 51

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Glu Trp Lys Thr Ser Leu Thr
    50                  55                  60
```

-continued

```
Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 52
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PALB5
      ; GenBank#AF349997

<400> SEQUENCE: 52

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gcc ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca aat gtt gct gct tca tta ttt aag aag ctt      384
Ile Leu Ala Ala Cys Thr Asn Val Ala Ala Ser Leu Phe Lys Lys Leu
```

-continued

```
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tgg cct gct ttc att att ggt atg gct gga tgg      480
Gly Leu Ala Pro Val Trp Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac cta aac ctt ata      672
Tyr Leu Met Gly Gly Glu Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 53
<211> LENGTH: 251
<212> TYPE: PRT
<213> ORGANISM: Naturally occurring gamma proteobacterium

<400> SEQUENCE: 53

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Asn Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Trp Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
```

-continued

```
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 54
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PalB7;
      GenBank #AF349999

<400> SEQUENCE: 54

atg ggt aaa tta tta ctg ata tta ggt agt gct att gcg ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt acg gct ggt atg tta gcg gca act gta ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg      240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gcc gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca ttg gta atg tta ggt gct gga tct gca ggc gaa gct      432
Leu Ala Gly Ser Leu Val Met Leu Gly Ala Gly Ser Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctc ata      672
Tyr Leu Met Gly Gly Glu Gly Val Tyr Ala Ser Asn Leu Asn Leu Ile
    210                 215                 220
```

-continued

```
tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 55
<211> LENGTH: 251
<212> TYPE: PRT
<213> ORGANISM: Naturally occurring gamma proteobacterium

<400> SEQUENCE: 55

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Ser Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 56
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PalB6;
     GenBank # AF349998

<400> SEQUENCE: 56

atg ggt aaa tta tta ctg ata tta ggt agt gct att gca ctt cca tca       48
```

-continued

```
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca aat gtt gct gct tca tta ttt aag aag ctt      384
Ile Leu Ala Ala Cys Thr Asn Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tgg cct gct ttc att att ggt atg gct gga tgg      480
Gly Leu Ala Pro Val Trp Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg gtg      576
Ser Thr Ala Ser Pro Ala Val Asn Ser Ala Tyr Asn Ala Met Met Val
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac cta aac ctt ata      672
Tyr Leu Met Gly Gly Glu Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 57
<211> LENGTH: 251
<212> TYPE: PRT
<213> ORGANISM: Naturally occurring gamma proteobacterium

<400> SEQUENCE: 57

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45
```

-continued

```
Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Asn Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Trp Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Val
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 58
<211> LENGTH: 753
<212> TYPE: DNA
<213> ORGANISM: Naturally occurring gamma proteobacteria
<220> FEATURE:
<221> NAME/KEY: CDS
<222> LOCATION: (1)..(753)
<223> OTHER INFORMATION: Proteorhodopsin variant from pcr clone PalB8;
      GenBank #AF350000

<400> SEQUENCE: 58

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
```

-continued

```
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggt aag gct gct gta      528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg      576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205

tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220

tat aac ctt gct gac ctt gtt aac aag att cta ttt ggt ttg atc att      720
Tyr Asn Leu Ala Asp Leu Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 59
<211> LENGTH: 251
<212> TYPE: PRT
<213> ORGANISM: Naturally occurring gamma proteobacteria

<400> SEQUENCE: 59

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175
```

-continued

```
Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Leu Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 60
<211> LENGTH: 753
<212> TYPE: DNA
<213> ORGANISM: Naturally occurring gamma proteobacteria
<220> FEATURE:
<221> NAME/KEY: CDS
<222> LOCATION: (1)..(753)
<223> OTHER INFORMATION: Proteorhodopsin variant from pcr clone PalE1
      ;GenBank# AF350001

<400> SEQUENCE: 60

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gac act ggt gat acc cca aca gta ttc aga tat      288
Arg Gly Val Trp Ile Asp Thr Gly Asp Thr Pro Thr Val Phe Arg Tyr
                85                  90                  95

att gat tgg tta tta act gtt cca tta caa gtg gtt gag ttc tat cta      336
Ile Asp Trp Leu Leu Thr Val Pro Leu Gln Val Val Glu Phe Tyr Leu
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta tat atg ggt gaa ggc aag gct gct gta      528
Leu Tyr Met Ile Tyr Glu Leu Tyr Met Gly Glu Gly Lys Ala Ala Val
                165                 170                 175

agt act gca agt cct gct gtt aac cct gca tac aac gca atg atg atg      576
Ser Thr Ala Ser Pro Ala Val Asn Pro Ala Tyr Asn Ala Met Met Met
            180                 185                 190

att att gtt gtt gga tgg gca att tat cct gct gga tat gct gct ggt      624
Ile Ile Val Val Gly Trp Ala Ile Tyr Pro Ala Gly Tyr Ala Ala Gly
        195                 200                 205
```

-continued

```
tac cta atg ggt ggc gaa ggt gta tac gct tca aac tta aac ctt ata      672
Tyr Leu Met Gly Gly Glu Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250


<210> SEQ ID NO 61
<211> LENGTH: 251
<212> TYPE: PRT
<213> ORGANISM: Naturally occurring gamma proteobacteria

<400> SEQUENCE: 61

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Val Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Pro Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 62
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PalE6
     ; GenBank#AF350002
```

-continued

<400> SEQUENCE: 62

```
atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gta ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tac atg      240
Val Ser Gly Leu Ile Thr Gly Ile Ala Phe Trp His Tyr Leu Tyr Met
65                  70                  75                  80

aga ggt gtt tgg ata gat act ggt gat aca cca aca gta ttt aga tat      288
Arg Gly Val Trp Ile Asp Thr Gly Asp Thr Pro Thr Val Phe Arg Tyr
                85                  90                  95

att gat tgg tta tta act gtt cca tta caa atg gtt gag ttc tat cta      336
Ile Asp Trp Leu Leu Thr Val Pro Leu Gln Met Val Glu Phe Tyr Leu
            100                 105                 110

att ctt gct gct tgt aca agt gtt gct gct tca tta ttt aag aag ctt      384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct      432
Leu Ala Gly Ser Leu Val Met Leu Gly Ala Gly Phe Ala Gly Glu Ala
    130                 135                 140

ggt tta gct cct gta tta cct gct ttc att att ggt atg gct gga tgg      480
Gly Leu Ala Pro Val Leu Pro Ala Phe Ile Ile Gly Met Ala Gly Trp
145                 150                 155                 160

tta tac atg att tat gag cta cat atg ggt gaa ggt aag gct gct gta      528
Leu Tyr Met Ile Tyr Glu Leu His Met Gly Glu Gly Lys Ala Ala Val
                165                 170                 175

agt act gca agt cct gct gtt aac tct gca tac aac gca atg atg aag      576
Ser Thr Ala Ser Pro Ala Val Asn Ser Ala Tyr Asn Ala Met Met Lys
            180                 185                 190

att att gtt att gga tgg gca att tat cct gct gga tat gct gct ggt      624
Ile Ile Val Ile Gly Trp Ala Ile Tyr Pro Ala Gly Tyr Ala Ala Gly
        195                 200                 205

tac cta atg agt ggt gac ggt gta tac gct tca aac tta aac ctt ata      672
Tyr Leu Met Ser Gly Asp Gly Val Tyr Ala Ser Asn Leu Asn Leu Ile
    210                 215                 220

tat aac ctt gct gac ttt gtt aac aag att cta ttt ggt ttg atc att      720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                          753
Trp Asn Val Ala Val Lys Glu Ser Ser Asn Ala
                245                 250
```

<210> SEQ ID NO 63
<211> LENGTH: 251
<212> TYPE: PRT
<213> ORGANISM: Naturally occurring gamma proteobacterium

<400> SEQUENCE: 63

```
Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
```

-continued

```
        20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160

Leu Tyr Met Ile Tyr Glu Leu His Met Gly Glu Gly Lys Ala Ala Val
                165                 170                 175

Ser Thr Ala Ser Pro Ala Val Asn Ser Ala Tyr Asn Ala Met Met Lys
            180                 185                 190

Ile Ile Val Ile Gly Trp Ala Ile Tyr Pro Ala Gly Tyr Ala Ala Gly
        195                 200                 205

Tyr Leu Met Ser Gly Asp Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 64
<211> LENGTH: 753
<212> TYPE: DNA
<213> ORGANISM: Naturally occurring gamma proteobacterium
<220> FEATURE:
<221> NAME/KEY: CDS
<222> LOCATION: (1)..(753)
<223> OTHER INFORMATION: Proteorhodopsin variant from pcr clone PalE7;
      GenBank# AF350003

<400> SEQUENCE: 64

atg ggt aaa tta tta ctg ata tta ggt agt gct att gca ctt cca tca       48
Met Gly Lys Leu Leu Leu Ile Leu Gly Ser Ala Ile Ala Leu Pro Ser
1               5                   10                  15

ttt gct gct gct ggt ggc gat cta gat ata agt gat act gtt ggt gtt       96
Phe Ala Ala Ala Gly Gly Asp Leu Asp Ile Ser Asp Thr Val Gly Val
            20                  25                  30

tca ttc tgg ctg gtt aca gct ggt atg tta gcg gca act gtg ttc ttt      144
Ser Phe Trp Leu Val Thr Ala Gly Met Leu Ala Ala Thr Val Phe Phe
        35                  40                  45

ttt gta gaa aga gac caa gtc agc gct aag tgg aaa act tca ctt act      192
Phe Val Glu Arg Asp Gln Val Ser Ala Lys Trp Lys Thr Ser Leu Thr
    50                  55                  60

gta tct ggt tta att act ggt ata gct ttt tgg cat tat ctc tat atg      240
Val Ser Gly Leu Ile Thr Gly Ile Ala Phe Trp His Tyr Leu Tyr Met
65                  70                  75                  80

aga ggt gtt tgg ata gat act ggt gat acc cca aca gta ttc aga tat      288
Arg Gly Val Trp Ile Asp Thr Gly Asp Thr Pro Thr Val Phe Arg Tyr
```

-continued

```
                 85                  90                  95

att gat tgg tta tta act gtt cca tta caa atg gtt gag ttc tat cta       336
Ile Asp Trp Leu Leu Thr Val Pro Leu Gln Met Val Glu Phe Tyr Leu
            100                 105                 110

att ctt gct gct tgt aca agt gtt gct gct tca tta ttt aag aag ctt       384
Ile Leu Ala Ala Cys Thr Ser Val Ala Ala Ser Leu Phe Lys Lys Leu
        115                 120                 125

cta gct ggt tca tta gta atg tta ggt gct gga ttt gca ggc gaa gct       432
Leu Ala Gly Ser Leu Val Met Leu Gly Ala Gly Phe Ala Gly Glu Ala
    130                 135                 140

gga tta gct cct gta tta cct gct ttc att att ggt atg gct gga tgg       480
Gly Leu Ala Pro Val Leu Pro Ala Phe Ile Ile Gly Met Ala Gly Trp
145                 150                 155                 160

cta tac atg att tat gag cta tat atg ggt gaa ggt aag gct gct gta       528
Leu Tyr Met Ile Tyr Glu Leu Tyr Met Gly Glu Gly Lys Ala Ala Val
                165                 170                 175

agt act gca agt cct gct gtt aac tct gca tac aac gca atg atg atg       576
Ser Thr Ala Ser Pro Ala Val Asn Ser Ala Tyr Asn Ala Met Met Met
            180                 185                 190

att att gtt gtt gga tgg gca att tat cct gct gga tat gct gct ggt       624
Ile Ile Val Val Gly Trp Ala Ile Tyr Pro Ala Gly Tyr Ala Ala Gly
        195                 200                 205

tac cta atg ggt ggc gaa ggc gta tac gct tca aac tta aac ctt ata       672
Tyr Leu Met Gly Gly Glu Gly Val Tyr Ala Ser Asn Leu Asn Leu Ile
    210                 215                 220

tat aac ctt gct gac ttt gtt aac aag att cta ttt ggt ttg atc att       720
Tyr Asn Leu Ala Asp Phe Val Asn Lys Ile Leu Phe Gly Leu Ile Ile
225                 230                 235                 240

tgg aat gtt gct gtt aaa gaa tct tct aat gct                           753
Trp Asn Val Ala Val Lys Glu Ser Ser Asn Ala
                245                 250


<210> SEQ ID NO 65
<211> LENGTH: 251
<212> TYPE: PRT
<213> ORGANISM: Naturally occurring gamma proteobacterium

<400> SEQUENCE: 65

Met Gly Lys Leu Leu Leu Ile Leu Gly Ser Ala Ile Ala Leu Pro Ser
1               5                   10                  15

Phe Ala Ala Ala Gly Gly Asp Leu Asp Ile Ser Asp Thr Val Gly Val
            20                  25                  30

Ser Phe Trp Leu Val Thr Ala Gly Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Asp Thr Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Ser Val Ala Ala Ser Leu Phe Lys Lys Leu
        115                 120                 125

Leu Ala Gly Ser Leu Val Met Leu Gly Ala Gly Phe Ala Gly Glu Ala
    130                 135                 140

Gly Leu Ala Pro Val Leu Pro Ala Phe Ile Ile Gly Met Ala Gly Trp
145                 150                 155                 160
```

-continued

```
Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Val Gly Trp Ala Ile Tyr Pro Ala Gly Tyr Ala Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250
```